(12) United States Patent
Hartner et al.

(10) Patent No.: US 9,012,175 B2
(45) Date of Patent: Apr. 21, 2015

(54) MUTANT AOX1 PROMOTERS

(75) Inventors: Franz Hartner, Graz (AT); Anton Glieder, Gleisdorf (AT)

(73) Assignees: Technische Universitat Graz, Graz (AT); VTU Holding GmbH, Grambach (AT)

( * ) Notice: Subject to any disclaimer, the term of this patent is extended or adjusted under 35 U.S.C. 154(b) by 1598 days.

(21) Appl. No.: 11/817,005

(22) PCT Filed: Feb. 23, 2006

(86) PCT No.: PCT/AT2006/000079
§ 371 (c)(1),
(2), (4) Date: Aug. 23, 2007

(87) PCT Pub. No.: WO2006/089329
PCT Pub. Date: Aug. 31, 2006

(65) Prior Publication Data
US 2008/0153126 A1     Jun. 26, 2008

(30) Foreign Application Priority Data

Feb. 23, 2005   (AT) .................................. A 304/2005

(51) Int. Cl.
*C07H 21/04*     (2006.01)
*C12N 15/00*     (2006.01)
*C12N 15/81*     (2006.01)

(52) U.S. Cl.
CPC ....... *C12N 15/815* (2013.01); *C12Y 101/03013* (2013.01)

(58) Field of Classification Search
None
See application file for complete search history.

(56) References Cited

U.S. PATENT DOCUMENTS 5,641,661 A     6/1997  Kumagai et al.

FOREIGN PATENT DOCUMENTS

| EP | 0 506 040 A1 | 3/1992 |
|----|--------------|--------|
| EP | 0 510 693 A2 | 4/1992 |
| EP | 0 606 917 A2 | 1/1997 |
| EP | 0 931 837 A1 | 1/1998 |
| EP | 1 431 387 A1 | 12/2003 |
| WO | 00/56903 A2  | 9/2000 |
| WO | 02/081650 A2 | 10/2002 |

OTHER PUBLICATIONS

International Search Report and Written Opinion for PCT/AT2006/000079.
Dai, et al., "Isolation and Characterization of PAOX2 mutant in *Pichia pastoris*," ACTA Genetica Sinica (2000), 27:641-646 (Chinese translation).
Kern, et al., "Extending Life by Alternative Respiration," Journal of Biotechnology (2005), 118:S50 (abstract).
Rosenfeld, et al., "Use of *Pichia pastoris* for Expression of Recombinant Proteins," Methods in Enzymology (1999), p. 154-169.

*Primary Examiner* — Celine Qian
(74) *Attorney, Agent, or Firm* — Nevrivy Patent Law Group P.L.L.C.

(57) ABSTRACT

A mutant *Pichia pastoris* alcohol oxidase 1 (AOX1) promoter of the wild type *Pichia pastoris* AOX1 promoter (SEQ ID No. 1) comprising at least one mutation selected from the group consisting of: a) a transcription factor binding site (TFBS), b) nucleotides 170 to 235 (−784 to −719), nucleotides 170 to 191 (−784 to −763), nucleotides 192 to 213 (−762 to −741), nucleotides 192 to 210 (−762 to −744), nucleotides 207 to 209 (−747 to −745), nucleotides 214 to 235 (−740 to −719), nucleotides 304 to 350 (−650 to −604), nucleotides 364 to 393 (−590 to −561), nucleotides 434 to 508 (−520 to −446), nucleotides 509 to 551 (−445 to −403), nucleotides 552 to 560 (−402 to −394), nucleotides 585 to 617 (−369 to −337), nucleotides 621 to 660 (−333 to −294), nucleotides 625 to 683 (−329 to −271), nucleotides 736 to 741 (−218 to −213), nucleotides 737 to 738 (−217 to −216), nucleotides 726 to 755 (−228 to −199), nucleotides 784 to 800 (−170 to −154) or nucleotides 823 to 861 (−131 to −93) of Seq ID No. 1, and combinations thereof.

29 Claims, 8 Drawing Sheets

SEQUENCE LISTING

<160> NUMBER OF SEQ ID NOS: 137

<210> SEQ ID NO 1
<211> LENGTH: 953
<212> TYPE: DNA
<213> ORGANISM: Pichia pastoris

<400> SEQUENCE: 1

```
ggtaccagat ctaacatcca aagacgaaag gttgaatgaa accttttgc catccgacat      60
ccacaggtcc attctcacac ataagtgcca aacgcaacag gagggatac actagcagca    120
gaccgttgca aacgcaggac ctccactcct cttctcctca cacccactt tgccatcga    180
aaaaccagcc cagttattgg gcttgattgg agctcgctca ttccaattcc ttctattagg    240
ctactaacac catgacttta ttagcctgtc tatcctggcc ccctggcga ggttcatgtt     300
tgtttatttc cgaatgcaac aagctccgca ttacacccga catcactcc agatgagggc    360
tttctgagtg tggggtcaaa tagtttcatg ttccccaaat ggcccaaaac tgacagttta    420
aacgctgtct tggaacctaa tatgacaaaa gcgtgatctc atccaagatg aactaagttt    480
ggttcgttga atgctaacg gccagttggt caaaaagaaa cttccaaaag tcggcatacc    540
gtttgtcttg tttggtattg attgacgaat gctcaaaaat aatctcatta atgcttagcg    600
cagtctctct atcgcttctg aaccccggtg cacctgtgcc gaaacgcaaa tggggaaaca    660
cccgcttttt ggatgattat gcattgtctc cacattgtat gcttccaaga ttctggtggg    720
aatactgctg atagcctaac gttcatgatc aaaatttaac tgttctaacc cctacttgac    780
agcaatatat aaacagaagg aagctgccct gtcttaaacc tttttttta tcatcattat    840
```

```
tagcttactt tcataattgc gactggttcc aattgacaag cttttgattt taacgacttt    900
taacgacaac ttgagaagat caaaaaacaa ctaattattg aaagaattca acc           953

<210> SEQ ID NO 2
<211> LENGTH: 32
<212> TYPE: DNA
<213> ORGANISM: Artificial
<220> FEATURE:
<223> OTHER INFORMATION: PRIMER

<400> SEQUENCE: 2
aaggtaccag atctaacatc caaagacgaa ag                                   32

<210> SEQ ID NO 3
<211> LENGTH: 42
<212> TYPE: DNA
<213> ORGANISM: Artificial
<220> FEATURE:
<223> OTHER INFORMATION: PRIMER

<400> SEQUENCE: 3
ctagccatgg ttgaattctt tcgaataatt agttgttttt tg                        42

<210> SEQ ID NO 4
<211> LENGTH: 30
<212> TYPE: DNA
<213> ORGANISM: Artificial
<220> FEATURE:
<223> OTHER INFORMATION: PRIMER

<400> SEQUENCE: 4
gaaagaattc aaccatggct agcaaaggag                                      30

<210> SEQ ID NO 5
<211> LENGTH: 34
<212> TYPE: DNA
<213> ORGANISM: Artificial
<220> FEATURE:
<223> OTHER INFORMATION: PRIMER

<400> SEQUENCE: 5
gatgatggtc tagaacgtgt cagtcctgct cctc                                 34

<210> SEQ ID NO 6
<211> LENGTH: 34
<212> TYPE: DNA
<213> ORGANISM: Artificial
<220> FEATURE:
<223> OTHER INFORMATION: PRIMER

<400> SEQUENCE: 6
gacacgttct agaccatcat catcatcatc attg                                 34

<210> SEQ ID NO 7
<211> LENGTH: 26
<212> TYPE: DNA
<213> ORGANISM: Artificial
<220> FEATURE:
<223> OTHER INFORMATION: PRIMER

<400> SEQUENCE: 7
atagcggccg cacaaacgaa ggtctc                                          26

<210> SEQ ID NO 8
```

```
<211> LENGTH: 40
<212> TYPE: DNA
<213> ORGANISM: Artificial
<220> FEATURE:
<223> OTHER INFORMATION: PRIMER

<400> SEQUENCE: 8
caacacccac tttaggctac taacaccatg actttattag                           40

<210> SEQ ID NO 9
<211> LENGTH: 34
<212> TYPE: DNA
<213> ORGANISM: Artificial
<220> FEATURE:
<223> OTHER INFORMATION: PRIMER

<400> SEQUENCE: 9
gttagtagcc taaagtgggt gttgaggaga agag                                 34

<210> SEQ ID NO 10
<211> LENGTH: 32
<212> TYPE: DNA
<213> ORGANISM: Artificial
<220> FEATURE:
<223> OTHER INFORMATION: PRIMER

<400> SEQUENCE: 10
gttcatgttt gtagatgagg gctttctgag tg                                   32

<210> SEQ ID NO 11
<211> LENGTH: 30
<212> TYPE: DNA
<213> ORGANISM: Artificial
<220> FEATURE:
<223> OTHER INFORMATION: PRIMER

<400> SEQUENCE: 11
gccctcatct acaaacatga acctcgccag                                      30

<210> SEQ ID NO 12
<211> LENGTH: 28
<212> TYPE: DNA
<213> ORGANISM: Artificial
<220> FEATURE:
<223> OTHER INFORMATION: PRIMER

<400> SEQUENCE: 12
gagggctttc ccaaatggcc caaaactg                                        28

<210> SEQ ID NO 13
<211> LENGTH: 28
<212> TYPE: DNA
<213> ORGANISM: Artificial
<220> FEATURE:
<223> OTHER INFORMATION: PRIMER

<400> SEQUENCE: 13
ccatttggga aagccctcat ctggagtg                                        28

<210> SEQ ID NO 14
<211> LENGTH: 31
<212> TYPE: DNA
<213> ORGANISM: Artificial
<220> FEATURE:
<223> OTHER INFORMATION: PRIMER

<400> SEQUENCE: 14
```

-continued cggccagttg ttggtattga ttgacgaatg c							31

<210> SEQ ID NO 15
<211> LENGTH: 29
<212> TYPE: DNA
<213> ORGANISM: Artificial
<220> FEATURE:
<223> OTHER INFORMATION: PRIMER

<400> SEQUENCE: 15
caataccaac aactggccgt tagcatttc							29

<210> SEQ ID NO 16
<211> LENGTH: 33
<212> TYPE: DNA
<213> ORGANISM: Artificial
<220> FEATURE:
<223> OTHER INFORMATION: PRIMER

<400> SEQUENCE: 16
gcttctgaac cttgtctcca cattgtatgc ttc							33

<210> SEQ ID NO 17
<211> LENGTH: 32
<212> TYPE: DNA
<213> ORGANISM: Artificial
<220> FEATURE:
<223> OTHER INFORMATION: PRIMER

<400> SEQUENCE: 17
gtggagacaa ggttcagaag cgatagagag ac							32

<210> SEQ ID NO 18
<211> LENGTH: 29
<212> TYPE: DNA
<213> ORGANISM: Artificial
<220> FEATURE:
<223> OTHER INFORMATION: PRIMER

<400> SEQUENCE: 18
gtctccacac tgctgatagc ctaacgttc							29

<210> SEQ ID NO 19
<211> LENGTH: 35
<212> TYPE: DNA
<213> ORGANISM: Artificial
<220> FEATURE:
<223> OTHER INFORMATION: PRIMER

<400> SEQUENCE: 19
ggctatcagc agtgtggaga caatgcataa tcatc							35

<210> SEQ ID NO 20
<211> LENGTH: 30
<212> TYPE: DNA
<213> ORGANISM: Artificial
<220> FEATURE:
<223> OTHER INFORMATION: PRIMER

<400> SEQUENCE: 20
ggaatactgc tctaacccct acttgacagc							30

<210> SEQ ID NO 21
<211> LENGTH: 32
<212> TYPE: DNA

```
<213> ORGANISM: Artificial
<220> FEATURE:
<223> OTHER INFORMATION: PRIMER

<400> SEQUENCE: 21 gtagggggtta gagcagtatt cccaccagaa tc                                    32

<210> SEQ ID NO 22
<211> LENGTH: 29
<212> TYPE: DNA
<213> ORGANISM: Artificial
<220> FEATURE:
<223> OTHER INFORMATION: PRIMER

<400> SEQUENCE: 22
cttgacagca agctgccctg tcttaaacc                                         29

<210> SEQ ID NO 23
<211> LENGTH: 28
<212> TYPE: DNA
<213> ORGANISM: Artificial
<220> FEATURE:
<223> OTHER INFORMATION: PRIMER

<400> SEQUENCE: 23
gggcagcttg ctgtcaagta ggggttag                                          28

<210> SEQ ID NO 24
<211> LENGTH: 34
<212> TYPE: DNA
<213> ORGANISM: Artificial
<220> FEATURE:
<223> OTHER INFORMATION: PRIMER

<400> SEQUENCE: 24
ctgtcttaaa ccttactggt tccaattgac aagc                                   34

<210> SEQ ID NO 25
<211> LENGTH: 29
<212> TYPE: DNA
<213> ORGANISM: Artificial
<220> FEATURE:
<223> OTHER INFORMATION: PRIMER

<400> SEQUENCE: 25
ggaaccagta aggtttaaga cagggcagc                                         29

<210> SEQ ID NO 26
<211> LENGTH: 44
<212> TYPE: DNA
<213> ORGANISM: Artificial
<220> FEATURE:
<223> OTHER INFORMATION: PRIMER

<400> SEQUENCE: 26
gatacactag cagcagaccg ttgcaaacgc aggacctcca ctcc                        44

<210> SEQ ID NO 27
<211> LENGTH: 47
<212> TYPE: DNA
<213> ORGANISM: Artificial
<220> FEATURE:
<223> OTHER INFORMATION: PRIMER

<400> SEQUENCE: 27
gtgaaggtga tgctacatac ggaaagctta cccttaaatt tatttgc                     47
```

<210> SEQ ID NO 28
<211> LENGTH: 41
<212> TYPE: DNA
<213> ORGANISM: Artificial
<220> FEATURE:
<223> OTHER INFORMATION: PRIMER

<400> SEQUENCE: 28
cgtggccgag gagcaggact gacacgttct agaccatcat c           41

<210> SEQ ID NO 29
<211> LENGTH: 22
<212> TYPE: DNA
<213> ORGANISM: Artificial
<220> FEATURE:
<223> OTHER INFORMATION: PRIMER

<400> SEQUENCE: 29
tccaaagacg aaaggttgaa tg                                22

<210> SEQ ID NO 30
<211> LENGTH: 23
<212> TYPE: DNA
<213> ORGANISM: Artificial
<220> FEATURE:
<223> OTHER INFORMATION: PRIMER

<400> SEQUENCE: 30
ccgtatgtag catcaccttc acc                               23

<210> SEQ ID NO 31
<211> LENGTH: 15
<212> TYPE: DNA
<213> ORGANISM: Artificial
<220> FEATURE:
<223> OTHER INFORMATION: Transcription factor binding site of AOX1

<400> SEQUENCE: 31
ctgtggatgt cggat                                        15

<210> SEQ ID NO 32
<211> LENGTH: 21
<212> TYPE: DNA
<213> ORGANISM: Artificial
<220> FEATURE:
<223> OTHER INFORMATION: Transcription factor binding site of AOX1

<400> SEQUENCE: 32
agaagaggag tggaggtcct g                                 21

<210> SEQ ID NO 33
<211> LENGTH: 13
<212> TYPE: DNA
<213> ORGANISM: Artificial
<220> FEATURE:
<223> OTHER INFORMATION: Transcription factor binding site of AOX1

<400> SEQUENCE: 33
caagcccaat aac                                          13

<210> SEQ ID NO 34
<211> LENGTH: 13
<212> TYPE: DNA
<213> ORGANISM: Artificial
<220> FEATURE:

```
<223> OTHER INFORMATION: Transcription factor binding site of AOX1

<400> SEQUENCE: 34
gagctccaat caa                                                        13

<210> SEQ ID NO 35
<211> LENGTH: 15
<212> TYPE: DNA
<213> ORGANISM: Artificial
<220> FEATURE:
<223> OTHER INFORMATION: Transcription factor binding site of AOX1

<400> SEQUENCE: 35
ctcgctcatt ccaat                                                      15

<210> SEQ ID NO 36
<211> LENGTH: 9
<212> TYPE: DNA
<213> ORGANISM: Artificial
<220> FEATURE:
<223> OTHER INFORMATION: Transcription factor binding site of AOX1

<400> SEQUENCE: 36 ccaggggggg                                                             9

<210> SEQ ID NO 37
<211> LENGTH: 15
<212> TYPE: DNA
<213> ORGANISM: Artificial
<220> FEATURE:
<223> OTHER INFORMATION: Transcription factor binding site of AOX1

<400> SEQUENCE: 37
tacacccgaa catca                                                      15

<210> SEQ ID NO 38
<211> LENGTH: 7
<212> TYPE: DNA
<213> ORGANISM: Artificial
<220> FEATURE:
<223> OTHER INFORMATION: Transcription factor binding site of AOX1

<400> SEQUENCE: 38 tggggtc                                                                7

<210> SEQ ID NO 39
<211> LENGTH: 20
<212> TYPE: DNA
<213> ORGANISM: Artificial
<220> FEATURE:
<223> OTHER INFORMATION: Transcription factor binding site of AOX1

<400> SEQUENCE: 39
agaaacttcc aaaagtcggc                                                 20

<210> SEQ ID NO 40
<211> LENGTH: 13
<212> TYPE: DNA
<213> ORGANISM: Artificial
<220> FEATURE:
<223> OTHER INFORMATION: Transcription factor binding site of AOX1

<400> SEQUENCE: 40
atcatccaaa aag                                                        13
```

```
<210> SEQ ID NO 41
<211> LENGTH: 11
<212> TYPE: DNA
<213> ORGANISM: Artificial
<220> FEATURE:
<223> OTHER INFORMATION: Transcription factor binding site of AOX1

<400> SEQUENCE: 41
tgcattgtct c                                                            11

<210> SEQ ID NO 42
<211> LENGTH: 15
<212> TYPE: DNA
<213> ORGANISM: Artificial
<220> FEATURE:
<223> OTHER INFORMATION: Transcription factor binding site of AOX1

<400> SEQUENCE: 42
atgcttccaa gattc                                                        15

<210> SEQ ID NO 43
<211> LENGTH: 21
<212> TYPE: DNA
<213> ORGANISM: Artificial
<220> FEATURE:
<223> OTHER INFORMATION: Transcription factor binding site of AOX1

<400> SEQUENCE: 43
acagttaaat tttgatcatg a                                                 21

<210> SEQ ID NO 44
<211> LENGTH: 66
<212> TYPE: DNA
<213> ORGANISM: Artificial
<220> FEATURE:
<223> OTHER INFORMATION: Nucleic acid fragment deleted from the AOX1
      promoter

<400> SEQUENCE: 44
tttgccatcg aaaaaccagc ccagttattg ggcttgattg gagctcgctc attccaattc        60
cttcta                                                                  66

<210> SEQ ID NO 45
<211> LENGTH: 47
<212> TYPE: DNA
<213> ORGANISM: Artificial
<220> FEATURE:
<223> OTHER INFORMATION: Nucleic acid fragment deleted from the AOX1
      promoter

<400> SEQUENCE: 45
ttatttccga atgcaacaag ctccgcatta cacccgaaca tcactcc                     47

<210> SEQ ID NO 46
<211> LENGTH: 30
<212> TYPE: DNA
<213> ORGANISM: Artificial
<220> FEATURE:
<223> OTHER INFORMATION: Nucleic acid fragment deleted from the AOX1
      promoter

<400> SEQUENCE: 46
ctgagtgtgg ggtcaaatag tttcatgttc                                        30

<210> SEQ ID NO 47
<211> LENGTH: 43
```

```
<212> TYPE: DNA
<213> ORGANISM: Artificial
<220> FEATURE:
<223> OTHER INFORMATION: Nucleic acid fragment deleted from the AOX1
      promoter

<400> SEQUENCE: 47
gtcaaaaaga aacttccaaa agtcggcata ccgtttgtct tgt                43

<210> SEQ ID NO 48
<211> LENGTH: 59
<212> TYPE: DNA
<213> ORGANISM: Artificial
<220> FEATURE:
<223> OTHER INFORMATION: Nucleic acid fragment deleted from the AOX1
      promoter

<400> SEQUENCE: 48
ccggtgcacc tgtgccgaaa cgcaaatggg gaaacacccg cttttggat gattatgca    59

<210> SEQ ID NO 49
<211> LENGTH: 30
<212> TYPE: DNA
<213> ORGANISM: Artificial
<220> FEATURE:
<223> OTHER INFORMATION: Nucleic acid fragment deleted from the AOX1
      promoter

<400> SEQUENCE: 49
attgtatgct tccaagattc tggtgggaat                               30

<210> SEQ ID NO 50
<211> LENGTH: 35
<212> TYPE: DNA
<213> ORGANISM: Artificial
<220> FEATURE:
<223> OTHER INFORMATION: Nucleic acid fragment deleted from the AOX1
      promoter

<400> SEQUENCE: 50
tgatagccta acgttcatga tcaaaattta actgt                         35

<210> SEQ ID NO 51
<211> LENGTH: 17
<212> TYPE: DNA
<213> ORGANISM: Artificial
<220> FEATURE:
<223> OTHER INFORMATION: Nucleic acid fragment deleted from the AOX1
      promoter

<400> SEQUENCE: 51
aatatataaa cagaagg                                             17

<210> SEQ ID NO 52
<211> LENGTH: 39
<212> TYPE: DNA
<213> ORGANISM: Artificial
<220> FEATURE:
<223> OTHER INFORMATION: Nucleic acid fragment deleted from the AOX1
      promoter

<400> SEQUENCE: 52
tttttttatc atcattatta gcttactttc ataattgcg                     39

<210> SEQ ID NO 53
<211> LENGTH: 40
<212> TYPE: DNA
```

```
<213> ORGANISM: Artificial
<220> FEATURE:
<223> OTHER INFORMATION: Primer

<400> SEQUENCE: 53
gaatgaaacc tttttgccat atccacaggt ccattctcac                                40

<210> SEQ ID NO 54
<211> LENGTH: 40
<212> TYPE: DNA
<213> ORGANISM: Artificial
<220> FEATURE:
<223> OTHER INFORMATION: Primer

<400> SEQUENCE: 54
gaatggacct gtggatatgg caaaaaggtt tcattcaacc                                40

<210> SEQ ID NO 55
<211> LENGTH: 38
<212> TYPE: DNA
<213> ORGANISM: Artificial
<220> FEATURE:
<223> OTHER INFORMATION: Primer

<400> SEQUENCE: 55
ccgttgcaaa cgcaggacct cttctcctca acacccac                                  38

<210> SEQ ID NO 56
<211> LENGTH: 38
<212> TYPE: DNA
<213> ORGANISM: Artificial
<220> FEATURE:
<223> OTHER INFORMATION: Primer

<400> SEQUENCE: 56
gtgttgagga agaggtcc tgcgtttgca acggtctg                                    38

<210> SEQ ID NO 57
<211> LENGTH: 42
<212> TYPE: DNA
<213> ORGANISM: Artificial
<220> FEATURE:
<223> OTHER INFORMATION: Primer

<400> SEQUENCE: 57
cgaaaaacca gcccagttgc ttgattggag ctcgctcatt cc                             42

<210> SEQ ID NO 58
<211> LENGTH: 40
<212> TYPE: DNA
<213> ORGANISM: Artificial
<220> FEATURE:
<223> OTHER INFORMATION: Primer

<400> SEQUENCE: 58
gagcgagctc caatcaagca actgggctgg ttttcgatg                                 40

<210> SEQ ID NO 59
<211> LENGTH: 40
<212> TYPE: DNA
<213> ORGANISM: Artificial
<220> FEATURE:
<223> OTHER INFORMATION: Primer

<400> SEQUENCE: 59
cagcccagtt attgggcttg agctcgctca ttccaattcc                                40
```

```
<210> SEQ ID NO 60
<211> LENGTH: 40
<212> TYPE: DNA
<213> ORGANISM: Artificial
<220> FEATURE:
<223> OTHER INFORMATION: Primer

<400> SEQUENCE: 60
ggaattggaa tgagcgagct caagcccaat aactgggctg                              40

<210> SEQ ID NO 61
<211> LENGTH: 39
<212> TYPE: DNA
<213> ORGANISM: Artificial
<220> FEATURE:
<223> OTHER INFORMATION: Primer

<400> SEQUENCE: 61
ggcttgattg gagctcgcta attccttcta ttaggctac                               39

<210> SEQ ID NO 62
<211> LENGTH: 39
<212> TYPE: DNA
<213> ORGANISM: Artificial
<220> FEATURE:
<223> OTHER INFORMATION: Primer

<400> SEQUENCE: 62
gtagcctaat agaaggaatt agcgagctcc aatcaagcc                               39

<210> SEQ ID NO 63
<211> LENGTH: 42
<212> TYPE: DNA
<213> ORGANISM: Artificial
<220> FEATURE:
<223> OTHER INFORMATION: Primer

<400> SEQUENCE: 63
gcctgtctat cctggccggc gaggttcatg tttgtttatt tc                           42

<210> SEQ ID NO 64
<211> LENGTH: 42
<212> TYPE: DNA
<213> ORGANISM: Artificial
<220> FEATURE:
<223> OTHER INFORMATION: Primer

<400> SEQUENCE: 64
caaacatgaa cctcgccggc caggatagac aggctaataa ag                           42

<210> SEQ ID NO 65
<211> LENGTH: 38
<212> TYPE: DNA
<213> ORGANISM: Artificial
<220> FEATURE:
<223> OTHER INFORMATION: Primer

<400> SEQUENCE: 65
gcaacaagct ccgcattaca acatcactcc agatgagg                                38

<210> SEQ ID NO 66
<211> LENGTH: 38
<212> TYPE: DNA
<213> ORGANISM: Artificial
<220> FEATURE:
```

<223> OTHER INFORMATION: Primer

<400> SEQUENCE: 66
cctcatctgg agtgatgttg taatgcggag cttgttgc                                38

<210> SEQ ID NO 67
<211> LENGTH: 40
<212> TYPE: DNA
<213> ORGANISM: Artificial
<220> FEATURE:
<223> OTHER INFORMATION: Primer

<400> SEQUENCE: 67
ccagatgagg gctttctgag tgaaatagtt tcatgttccc                              40

<210> SEQ ID NO 68
<211> LENGTH: 40
<212> TYPE: DNA
<213> ORGANISM: Artificial
<220> FEATURE:
<223> OTHER INFORMATION: Primer

<400> SEQUENCE: 68
gggaacatga aactatttca ctcagaaagc cctcatctgg                              40

<210> SEQ ID NO 69
<211> LENGTH: 39
<212> TYPE: DNA
<213> ORGANISM: Artificial
<220> FEATURE:
<223> OTHER INFORMATION: Primer

<400> SEQUENCE: 69
gccagttggt caaaaacaaa agtcggcata ccgtttgtc                               39

<210> SEQ ID NO 70
<211> LENGTH: 40
<212> TYPE: DNA
<213> ORGANISM: Artificial
<220> FEATURE:
<223> OTHER INFORMATION: Primer

<400> SEQUENCE: 70
cggtatgccg actttgtttt ttgaccaact ggccgttagc                              40

<210> SEQ ID NO 71
<211> LENGTH: 42
<212> TYPE: DNA
<213> ORGANISM: Artificial
<220> FEATURE:
<223> OTHER INFORMATION: Primer

<400> SEQUENCE: 71
caaatgggga acacccgct tatgattatg cattgtctcc ac                            42

<210> SEQ ID NO 72
<211> LENGTH: 41
<212> TYPE: DNA
<213> ORGANISM: Artificial
<220> FEATURE:
<223> OTHER INFORMATION: Primer

<400> SEQUENCE: 72
gagacaatgc ataatcataa gcgggtgttt ccccatttgc g                            41

<210> SEQ ID NO 73
<211> LENGTH: 41
<212> TYPE: DNA
<213> ORGANISM: Artificial
<220> FEATURE:
<223> OTHER INFORMATION: Primer

<400> SEQUENCE: 73 gcttttgga tgattatgcc tccacattgt atgcttccaa g                 41

<210> SEQ ID NO 74
<211> LENGTH: 41
<212> TYPE: DNA
<213> ORGANISM: Artificial
<220> FEATURE:
<223> OTHER INFORMATION: Primer

<400> SEQUENCE: 74
cttggaagca tacaatgtgg aggcataatc atccaaaaag c                 41

<210> SEQ ID NO 75
<211> LENGTH: 42
<212> TYPE: DNA
<213> ORGANISM: Artificial
<220> FEATURE:
<223> OTHER INFORMATION: Primer

<400> SEQUENCE: 75
cattgtctcc acattgtatg aagattctgg tgggaatact gc                 42

<210> SEQ ID NO 76
<211> LENGTH: 40
<212> TYPE: DNA
<213> ORGANISM: Artificial
<220> FEATURE:
<223> OTHER INFORMATION: Primer

<400> SEQUENCE: 76
gtattcccac cagaatcttc atacaatgtg gagacaatgc                 40

<210> SEQ ID NO 77
<211> LENGTH: 42
<212> TYPE: DNA
<213> ORGANISM: Artificial
<220> FEATURE:
<223> OTHER INFORMATION: Primer

<400> SEQUENCE: 77
gctgatagcc taacgttcat gttctaaccc ctacttgaca gc                 42

<210> SEQ ID NO 78
<211> LENGTH: 41
<212> TYPE: DNA
<213> ORGANISM: Artificial
<220> FEATURE:
<223> OTHER INFORMATION: Primer

<400> SEQUENCE: 78
gtcaagtagg ggttagaaca tgaacgttag gctatcagca g                 41

<210> SEQ ID NO 79
<211> LENGTH: 41
<212> TYPE: DNA
<213> ORGANISM: Artificial
<220> FEATURE:
<223> OTHER INFORMATION: Primer

<400> SEQUENCE: 79
ggaatactgc tgatagcttc atgatcaaaa tttaactgtt c    41

<210> SEQ ID NO 80
<211> LENGTH: 40
<212> TYPE: DNA
<213> ORGANISM: Artificial
<220> FEATURE:
<223> OTHER INFORMATION: Primer

<400> SEQUENCE: 80
gttaaatttt gatcatgaag ctatcagcag tattcccacc    40

<210> SEQ ID NO 81
<211> LENGTH: 42
<212> TYPE: DNA
<213> ORGANISM: Artificial
<220> FEATURE:
<223> OTHER INFORMATION: Primer

<400> SEQUENCE: 81
ggaatactgc tgatagccac gttcatgatc aaaatttaac tg    42

<210> SEQ ID NO 82
<211> LENGTH: 40
<212> TYPE: DNA
<213> ORGANISM: Artificial
<220> FEATURE:
<223> OTHER INFORMATION: Primer

<400> SEQUENCE: 82
gttaaatttt gatcatgaac gtggctatca gcagtattcc    40

<210> SEQ ID NO 83
<211> LENGTH: 37
<212> TYPE: DNA
<213> ORGANISM: Artificial
<220> FEATURE:
<223> OTHER INFORMATION: Primer

<400> SEQUENCE: 83
gagatcagat ctaacatatg ccaaagacga aaggttg    37

<210> SEQ ID NO 84
<211> LENGTH: 37
<212> TYPE: DNA
<213> ORGANISM: Artificial
<220> FEATURE:
<223> OTHER INFORMATION: Primer

<400> SEQUENCE: 84
caacctttcg tctttggcat atgttagatc tgatctc    37

<210> SEQ ID NO 85
<211> LENGTH: 34
<212> TYPE: DNA
<213> ORGANISM: Artificial
<220> FEATURE:
<223> OTHER INFORMATION: Primer

<400> SEQUENCE: 85
aaacatatga gatctaacat ccaaagacga agg    34

<210> SEQ ID NO 86
<211> LENGTH: 27

```
<212> TYPE: DNA
<213> ORGANISM: Artificial
<220> FEATURE:
<223> OTHER INFORMATION: Primer

<400> SEQUENCE: 86
tggttgaatt ctttcaataa ttagttg                                        27

<210> SEQ ID NO 87
<211> LENGTH: 46
<212> TYPE: DNA
<213> ORGANISM: Artificial
<220> FEATURE:
<223> OTHER INFORMATION: Primer

<400> SEQUENCE: 87
cgccacaaca ttgaagatgg ttccgttcaa ctagcagacc attatc                   46

<210> SEQ ID NO 88
<211> LENGTH: 49
<212> TYPE: DNA
<213> ORGANISM: Artificial
<220> FEATURE:
<223> OTHER INFORMATION: Primer

<400> SEQUENCE: 88
ggaaacattc tcggacacaa acttgagtac aactataact cacacaatg                49

<210> SEQ ID NO 89
<211> LENGTH: 44
<212> TYPE: DNA
<213> ORGANISM: Artificial
<220> FEATURE:
<223> OTHER INFORMATION: Primer

<400> SEQUENCE: 89
atctcgagtt acttgtacaa ttcatccatg ccatgtgtaa tccc                     44

<210> SEQ ID NO 90
<211> LENGTH: 178
<212> TYPE: DNA
<213> ORGANISM: Artificial
<220> FEATURE:
<223> OTHER INFORMATION: AOX1 promoter fragment

<400> SEQUENCE: 90
cttaaggaca gcaatatata aacagaagga agctgccctg tcttaaacct ttttttttat    60
catcattatt agcttacttt cataattgcg actggttcca attgacaagc ttttgatttt   120
aacgactttt aacgacaact gagaagatc aaaaaacaac taattattga aagaattc      178

<210> SEQ ID NO 91
<211> LENGTH: 195
<212> TYPE: DNA
<213> ORGANISM: Artificial
<220> FEATURE:
<223> OTHER INFORMATION: AOX1 promoter fragment

<400> SEQUENCE: 91
cttaagtgtt ctaacccta cttgacagca atatataaac agaaggaagc tgccctgtct    60
taaacctttt ttttatcat cattattagc ttactttcat aattgcgact ggttccaatt   120
gacaagcttt tgattttaac gactttaac gacaacttga agatcaaa aacaactaa      180 ttattgaaag aattc                                                   195
```

```
<210> SEQ ID NO 92
<211> LENGTH: 12
<212> TYPE: DNA
<213> ORGANISM: Artificial
<220> FEATURE:
<223> OTHER INFORMATION: AOX1 promoter fragment

<400> SEQUENCE: 92
tagcctaacg tt                                                              12

<210> SEQ ID NO 93
<211> LENGTH: 14
<212> TYPE: DNA
<213> ORGANISM: Artificial
<220> FEATURE:
<223> OTHER INFORMATION: AOX1 promoter fragment

<400> SEQUENCE: 93
catgatcaaa attt                                                            14

<210> SEQ ID NO 94
<211> LENGTH: 32
<212> TYPE: DNA
<213> ORGANISM: Artificial
<220> FEATURE:
<223> OTHER INFORMATION: Primer

<400> SEQUENCE: 94
tttgaattct ttcaataatt agttgttttt tg                                        32

<210> SEQ ID NO 95
<211> LENGTH: 43
<212> TYPE: DNA
<213> ORGANISM: Artificial
<220> FEATURE:
<223> OTHER INFORMATION: Primer

<400> SEQUENCE: 95
ttagatctcg acttaaggac agcaatatat aaacagaagg aag                            43

<210> SEQ ID NO 96
<211> LENGTH: 39
<212> TYPE: DNA
<213> ORGANISM: Artificial
<220> FEATURE:
<223> OTHER INFORMATION: Primer

<400> SEQUENCE: 96
ttagatctcg acttaagtgt tctaacccct acttgacag                                 39

<210> SEQ ID NO 97
<211> LENGTH: 52
<212> TYPE: DNA
<213> ORGANISM: Artificial
<220> FEATURE:
<223> OTHER INFORMATION: Primer

<400> SEQUENCE: 97
aaagatctta gcctaacgtt cttaaggaca gcaatatata aacagaagga ag                  52

<210> SEQ ID NO 98
<211> LENGTH: 54
<212> TYPE: DNA
<213> ORGANISM: Artificial
<220> FEATURE:
<223> OTHER INFORMATION: Primer
```

<400> SEQUENCE: 98
aaagatctca tgatcaaaat ttcttaagga cagcaatata taaacagaag gaag            54

<210> SEQ ID NO 99
<211> LENGTH: 57
<212> TYPE: DNA
<213> ORGANISM: Artificial
<220> FEATURE:
<223> OTHER INFORMATION: Primer

<400> SEQUENCE: 99
gatctcgact taagcaatcg tcttactttc taacttttct tacctttac atttcag          57

<210> SEQ ID NO 100
<211> LENGTH: 31
<212> TYPE: DNA
<213> ORGANISM: Artificial
<220> FEATURE:
<223> OTHER INFORMATION: Primer

<400> SEQUENCE: 100
caatatatat atatatttca aggatatacc g                                     31

<210> SEQ ID NO 101
<211> LENGTH: 49
<212> TYPE: DNA
<213> ORGANISM: Artificial
<220> FEATURE:
<223> OTHER INFORMATION: Primer

<400> SEQUENCE: 101
aattcggtat atccttgaaa tatatatata tattgctgaa atgtaaaag                  49

<210> SEQ ID NO 102
<211> LENGTH: 39
<212> TYPE: DNA
<213> ORGANISM: Artificial
<220> FEATURE:
<223> OTHER INFORMATION: Primer

<400> SEQUENCE: 102
gtaagaaaag ttagaaagta agacgattgc ttaagtcga                             39

<210> SEQ ID NO 103
<211> LENGTH: 22
<212> TYPE: DNA
<213> ORGANISM: Artificial
<220> FEATURE:
<223> OTHER INFORMATION: Primer

<400> SEQUENCE: 103
ggttgaattc ggtatatcct tg                                               22

<210> SEQ ID NO 104
<211> LENGTH: 46
<212> TYPE: DNA
<213> ORGANISM: Artificial
<220> FEATURE:
<223> OTHER INFORMATION: Primer

<400> SEQUENCE: 104
aaagatctta gcctaacgtt cttaagcaat cgtcttactt tctaac                     46

<210> SEQ ID NO 105

```
<211> LENGTH: 15
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 105
gccatccgac atcca                                                          15

<210> SEQ ID NO 106
<211> LENGTH: 18
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 106
ggacctccac tcctcttc                                                       18

<210> SEQ ID NO 107
<211> LENGTH: 76
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 107
ccacttttgc catcgaaaaa ccagcccagt tattgggctt gattggagct cgctcattcc         60
aattccttct attagg                                                         76

<210> SEQ ID NO 108
<211> LENGTH: 15
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 108
cagttattgg gcttg                                                          15

<210> SEQ ID NO 109
<211> LENGTH: 15
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 109
gcttgattgg agctc                                                          15

<210> SEQ ID NO 110
<211> LENGTH: 16
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 110
tcgctcattc caattc                                                         16
```

```
<210> SEQ ID NO 111
<211> LENGTH: 15
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 111
tggcccccct ggcga                                                    15

<210> SEQ ID NO 112
<211> LENGTH: 57
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 112
tttgtttatt tccgaatgca acaagctccg cattacaccc gaacatcact ccagatg      57

<210> SEQ ID NO 113
<211> LENGTH: 15
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 113
attacacccg aacat                                                    15

<210> SEQ ID NO 114
<211> LENGTH: 40
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 114
gctttctgag tgtggggtca aatagtttca tgttccccaa                         40

<210> SEQ ID NO 115
<211> LENGTH: 17
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 115
gagtgtgggg tcaaata                                                  17

<210> SEQ ID NO 116
<211> LENGTH: 53
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 116
agttgacaag acaaacggta tgccgacttt tggaagtttc ttttgactt ggt            53

<210> SEQ ID NO 117
```

```
<211> LENGTH: 18
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 117
aaaaagaaac ttccaaaa                                                 18

<210> SEQ ID NO 118
<211> LENGTH: 69
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 118 gaacccggt gcacctgtgc cgaaacgcaa atggggaaac acccgctttt tggatgatta    60
tgcattgtc                                                           69

<210> SEQ ID NO 119
<211> LENGTH: 15
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 119 cgcttttttgg atgat                                                   15

<210> SEQ ID NO 120
<211> LENGTH: 15
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 120
tatgcattgt ctcca                                                    15

<210> SEQ ID NO 121
<211> LENGTH: 40
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 121
tccacattgt atgcttccaa gattctggtg ggaatactgc                         40

<210> SEQ ID NO 122
<211> LENGTH: 12
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 122
tagcctaacg tt                                                       12
```

```
<210> SEQ ID NO 123
<211> LENGTH: 15
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 123
gtatgcttcc aagat                                                      15

<210> SEQ ID NO 124
<211> LENGTH: 45
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 124
actgctgata gcctaacgtt catgatcaaa atttaactgt tctaa                     45

<210> SEQ ID NO 125
<211> LENGTH: 25
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 125
ttcatgatca aaatttaact gttct                                           25

<210> SEQ ID NO 126
<211> LENGTH: 36
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 126
atagcctaac gttcatgatc aaaatttaac tgttct                               36

<210> SEQ ID NO 127
<211> LENGTH: 27
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 127
acagcaatat ataaacagaa ggaagct                                         27

<210> SEQ ID NO 128
<211> LENGTH: 49
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 128
accttttttt ttatcatcat tattagctta ctttcataat tgcgactgg                 49

<210> SEQ ID NO 129
```

```
<211> LENGTH: 16
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 129
atagcctaac gttcat                                                     16

<210> SEQ ID NO 130
<211> LENGTH: 85
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 130
cttggaacct aatatgacaa aagcgtgatc tcatccaaga tgaactaagt ttggttcgtt     60
gaaatgctaa cggccagttg cttgg                                           85

<210> SEQ ID NO 131
<211> LENGTH: 32
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 131 ccactttttgc catcgaaaaa ccagcccagt ta                                  32

<210> SEQ ID NO 132
<211> LENGTH: 32
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 132
agcccagtta ttgggcttga ttggagctcg ct                                   32

<210> SEQ ID NO 133
<211> LENGTH: 32
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 133
ggagctcgct cattccaatt ccttctatta gg                                   32

<210> SEQ ID NO 134
<211> LENGTH: 51
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 134 ccactttttgc catcgaaaaa ccagcccagt tattgggctt gattggagct c             51
```

```
<210> SEQ ID NO 135
<211> LENGTH: 40
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 135
aatactgctg atagcctaac gttcatgatc aaaataatac                              40

<210> SEQ ID NO 136
<211> LENGTH: 43
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 136
taatctcatt aatgcttagc gcagtctctc tatcgcttta atc                          43

<210> SEQ ID NO 137
<211> LENGTH: 50
<212> TYPE: DNA
<213> ORGANISM: Artificial
<220> FEATURE:
<223> OTHER INFORMATION: AOX1 promoter fragment containing transcription
      factor binding site to be deleted

<400> SEQUENCE: 137
ttctgaaccc cggtgcacct gtgccgaaac gcaaatgggg aaacacccgc                   50
```

MUTANT AOX1 PROMOTERS

The present invention relates to mutant *Pichia pastoris* AOX1 promoters.

*S. cerevisiae* has dominated (and still dominates) the scientific and biotechnological use as eukaryotic model organism and production system. In the last century another yeast gained great attraction: the fission yeast *Schizosaccharomyces pombe*. For its attribute to reproduce only by means of fission *S. pombe* gained outstanding attention as model organism and by today it is the most intensely studied yeast species in terms of molecular genetics and cell biology, along with *S. cerevisiae*. Among over 700 different yeast species known to date, the two yeasts mentioned above can provide only a limited set of interesting attributes for technological and scientific applications. Since the 1970's or 80's more and more yeast species with outstanding characteristics were investigated for biotechnology and research. These so called non-conventional yeasts (NCY) or non-*Saccharomyces* yeasts (in this case the term *Saccharomyces* includes the yeast *Schizosaccharomyces pombe*) are developed for several reasons: they possess either medical importance like *Candida albicans* or technological relevance like *Yarrowia lipolytica* and *Kluyveromyces lactis* which have the ability to grow on particular substrates (e.g. n-alkanes, lactose). E.g. the most common human fungal pathogen *C. albicans* is studied extensively to reveal the nature of the virulence factors involved in pathogenesis therefore becoming the model organism for pathogenic yeasts. Another well established group of NCY are the methylotrophic yeasts *Pichia pastoris* and *Hansenula polymorpha* (*Pichia angusta*) which are superior to *S. cerevisiae* in terms of recombinant protein production and studies of peroxisome biogenesis. These are only the most prominent members of non-conventional yeasts still having either technological or academic attraction. To date several other species are also of particular interest and this group will grow rapidly the next years.

Sugars, the most abundant class of molecules in nature, are utilised by all known yeasts. Although there are great differences in substrate acceptance from species to species (see Table 1), the conversion of glucose 6-phosphate or fructose 6-phosphate to pyruvate is a common theme in their metabolism. Anyhow, the enzymatic equipment for the glycolytic pathway varies significantly among different yeasts. While in *S. cerevisiae* most of the enzymes are known and characterised, at least partially, only a few enzymes were described in NCYs. Some of the functions needed for glycolysis are mediated by several genes/enzymes in some yeasts, especially those playing an additional role in control or regulation of the metabolism and/or being on a branching point like glucokinase/hexokinase, phosphofructokinase and glyceraldehyde 3-phosphate dehydrogenase. Normally, the isoenzymes are regulated differentially indicating diverse functions under changing environmental prerequisites. Some of the genes encoding for glycolytic enzymes are constitutive and highly expressed, e.g. the *S. cerevisiae* PGK1 (phosphoglycerate kinase) or the *P. pastoris* GAP gene (glyceraldehyde 3-phosphate dehydrogenase) while other enzymes are strictly regulated like the ENO1 (enolase) gene of *S. cerevisiae*.

TABLE 1

Selected yeasts of biotechnological interest with relevant commercial substrates other than glucose and fructose

| Yeast | Energy metabolism | Selected substrates |
| --- | --- | --- |
| *S. cerevisiae* | Crabtree positive | sucrose, maltose, raffinose, ethanol |
| *S. pombe* | Crabtree positive | sucrose, maltose, raffinose |
| *Zygosaccharomyces bailii* | Crabtree positive | acetic acid, ethanol, glycerol |
| *Yarrowia lipolytica* | Crabtree negative | n-alkanes, fatty acids, ethanol |
| *Pichia stipitis* | Crabtree negative | xylose |
| *Pichia pastoris* | Crabtree negative | methanol, glycerol |
| *Hansenula polymorpha* | Crabtree negative | methanol, glycerol |
| *Schwanninomyces occidentalis* | Crabtree negative | starch, n-alkanes, xylose, sucrose, raffinose, trehalose, lactose, ethanol |
| *Kluyveromyces lactis* | Crabtree negative | lactose, sucrose, maltose, raffinose, ethanol, glycerol, xylitol, lactate |

The fate of pyruvate in metabolism varies significantly between yeast species and culture conditions. In *S. cerevisiae* and other so called Crabtree positive yeasts, respiration is inhibited by glucose and related sugars. This leads to the transformation of pyruvate via the pyruvate decarboxylase to ethanol and $CO_2$, even under high amounts of oxygen, which is also known as fermentation. In Crabtree negative yeasts, where the majority of NCY is belonging to, transformation of pyruvate to ethanol occurs only under anaerobic conditions. Under aerobic conditions pyruvate is oxidised to $CO_2$ via the pyruvate dehydrogenase and the tricarboxylic acid (TCA) cycle. The TCA cycle is of outstanding interest for the cell metabolism due to the fact that it is the only way for the oxidation of sugars to $CO_2$. Oxidation to $CO_2$ results in production of NADH, which is used for energy production. Furthermore TCA cycle intermediates are the major sources of metabolites for biosynthetic purposes. Due to the removal of intermediates the TCA cycle has to be refilled to keep it running. The main anaplerotic reactions in yeasts are the pyruvate carboxylase and the glyoxylate cycle. The first one is the major pathway when growing on ammonium as sole nitrogen source while the latter one is needed when growing on carbon sources with less than 3 carbon atoms. In contrast to this eminent interest almost nothing is known about genes or enzymes involved in the TCA cycle in NCYs. NADH generated by catabolic reactions, either in the cytosol or in mitochondria, has to be reoxidized to $NAD^+$ to keep the reactions running. In Crabtree negative yeasts (e.g. *Pichia pastoris*) under aerobic conditions NADH is reoxidized mainly through the respiratory chain. The situation is significantly different in Crabtree positive yeasts like *S. cerevisiae* where respiration and fermentation coexists. When grown on glucose under aerobic conditions, respiration is repressed by glucose and fermentation occurs. Under these conditions $NAD^+$ is regenerated by the formation of ethanol (NADH produced by glycolysis) or glycerol. Respiration in yeasts differs from the animal paradigm of this pathway as described in every biochemistry textbook. First, some yeasts, like *S. cerevisiae* and *Kluyveromyces lactis*, are lacking complex I of the respiratory chain. In these yeasts $NAD^+$ regeneration is done without pumping protons through the inner mitochondrial membrane by external and internal NADH dehydrogenases. The second major difference, found in Crabtree negative yeasts, fungi and plants, is an alternative respiration pathway in parallel to complex III and IV of the cytochrome chain. This alternative respiration is mediated by a so called alternative oxidase which transfers electrons directly from the ubiquinone pool to oxygen without pumping protons through the inner mitochondrial membrane.

NADPH for biosynthetic purposes is produced in the oxidative part of the pentose phosphate pathway (PPP). Other very important metabolites provided by this pathway are ribose 5-phosphate and erythrose 4-phosphate, needed for synthesis of nucleic acids and nucleotide cofactors and for the synthesis of aromatic amino acids, respectively. There are still many gaps in the information about genes and their corresponding enzymes involved in the PPP in non-conventional yeasts. A few enzymes were isolated from *Candida utilis, S. pombe* and *K. lactis*. Compositional and kinetic characterisation revealed several differences between these enzymes. Due to the lack of information the influence on the PPP in these yeasts cannot be estimated but it has been shown that e.g. phosphoglucose isomerase mutants of *K. lactis*, which are deficient in glycolysis, are able to grow in glucose media, in contrast to *S. cerevisiae*. This observation indicates that the capacity of the pentose phosphate pathway in *K. lactis* is sufficient for growth on glucose as carbon source. In methylotrophic yeasts, an additional transketolase (dihydroxyacetone synthase) could be found. This enzyme is localised in peroxisomes and confers the assimilation of formaldehyde into the cell metabolism by condensation with xylulose 5-phosphate with formation of dihydroxyacetone and glyceraldehyde 3-phosphate.

Yeasts as unicellular eukaryotic organisms provide attractive expression systems for recombinant protein production. They combine the pros of bacteria, like well-developed genetic manipulation techniques, simple, safe and therefore cheap (large-scale) cultivation techniques, with the main benefit of eukaryotic expression systems, namely eukaryotic protein processing. Due to the above-mentioned reasons *S. cerevisiae* has dominated this field for many years resulting in a large number of proteins (e.g. insulin, HBsAg, HSA) produced in this organism. *S. cerevisiae* shows some limitations due to hyperglycosylation, retention of secreted proteins in the periplasmic space, plasmid instability and low product yields. To overcome the limitations of this single organism a small set of non-conventional yeasts has been developed as hosts for heterologous gene expression. Among others, *K. lactis, Y. lipolytica* and the methylotrophic yeasts *Candida boidinii, H. polymorpha* and *P. pastoris* were used, but only the latter 2 species gained outstanding commercial interest. *Schizosaccharomyces pombe* exhibits some characteristics with close proximity to higher eukaryotes which makes this yeast a very attractive host for heterologous protein production: (1) the transcription initiation mechanism is more similar to that of higher eukaryotes, (2) some mammalian promoters are functional in *S. pombe*, (3) the capability of RNA-splicing, highlighting in a similarity of components of the splicosome to that of mammalians, (4) the mammalian endoplasmatic reticulum retention signal KDEL can be recognised, (5) the existence of galactose residues in glycoproteins and (6) some other posttranslational modifications like acetylation and isoprenylation of proteins are performed in a more similar way to mammalian than yeast cells. Several of the above-mentioned features might increase the importance of *S. pombe* in recombinant protein production in the near future in respect to production of authentic heterologous proteins and high-throughput applications thereof, like structural and functional genomics.

All microorganisms possess mechanisms to adapt their metabolism for optimal utilisation of nutrients available in the environment. Fast and accurate adaptation to these environmental constraints is the major factor controlling growth and other physiological parameters of all organisms. For yeast, as for most microorganisms glucose is the preferred carbon and energy source. Therefore it is not surprising that glucose, the most abundant monosaccharide in nature, is a major messenger for cells affecting growth and development of these organisms by regulation of gene expression, mainly, but not exclusively, on the transcriptional control level. Genomic transcription analysis revealed that a considerable amount of genes is regulated by the environmental determined glucose level. Genes with known metabolic function in glucose utilisation like low-affinity glucose transporters and glycolytic enzymes as well as genes encoding ribosomal proteins are induced by glucose. On the other hand glucose represses a large set of genes, including genes involved in utilisation of alternative carbon sources, gluconeogenesis, the glyoxylate cycle, peroxisomal functions and respiration. Repression of respiration (Crabtree effect) occurs only in a few yeast species (fermentative yeasts, Crabtree positive) like *Saccharomyces cerevisiae* while in the majority of yeast species glucose does not repress respiration (Crabtree negative). Although a broad knowledge on the glucose repression machinery was achieved over the last 20 years, mainly based on the yeast *Saccharomyces cerevisiae*, its actual mechanism, especially the upstream parts of glucose sensing and signalling, is not fully understood. Nevertheless, to get a better understanding of the present work, a few main players of carbon catabolite repression as described for *S. cerevisiae* are described briefly below.

The SNF1 gene encodes for a Ser/Thr protein kinase which can be found in high molecular mass complexes in yeast cells. It is regulated by conformational changes within the complex caused by phosphorylation in the regulatory subunit of Snf1p. To date 3 upstream kinases (Pak1p, Elm1p and Tos3p) are identified to phosphorylate and therefore activate Snf1p. Its activity is absolutely required for the derepression of a wide variety of genes repressed by glucose. Hence it is not surprising that Snf1p or homologues are widely conserved in eukaryotes.

The zink finger protein Mig1p is able to bind to promoter regions of a wide variety of genes repressed by glucose. It is acting most probably by recruiting the general repressor complex Ssn6(Cyc8)-Tup1p. The function of Mig1p is controlled by the protein kinase Snf1, yet there is no clear evidence for a direct phosphorylation. Mig1p is localised in the nucleus in its non-phosphorylated form. Glucose depletion causes phosphorylation of Mig1p followed by translocation to the cytoplasm. When glucose is added to the cells Mig1p quickly moves back to the nucleus and represses transcription.

Adr1p also belongs to the family of zink finger proteins and was found to be a positive effector of peroxisomal proteins and the ADH2 gene, encoding for the glucose repressed alcohol dehydrogenase II. ADR1 expression is downregulated by glucose through the cyclic AMP (cAMP)-dependent protein kinase at high cAMP levels. The main regulatory effect appears at the mRNA translation level, but regulatory effects on transcription as well as mRNA stability were also observed, depending on the *S. cerevisiae* strain analysed.

For a large number of genes including many of the genes involved in respiratory metabolism transcription is activated on non-fermentable carbon sources by the Hap2/3/4/5 complex. For a few genes involved in respiration like CYC1 (encoding for iso-1-cytochrome c) and COX6 (cytochrome c oxidase subunit VI) it has been established that Snf1 is required for derepression after growth on glucose. Transcription of HAP4 is repressed when glucose is present, nonetheless a direct involvement of either Hap4p or Snf1p in derepression could not be shown.

Gcr1p is a major transcription activator protein of glycolytic genes (e.g. enolase, glyceraldehyde 3-phosphate dehydrogenase). Gcr1p, together with the general transcription factor Rap1p is the principal item of glycolytic gene expression in respect to coordination of transcription and it is absolutely necessary for high level expression. Genomic expression pattern of wild-type and *S. cerevisiae* gcr 1 mutant growing on various carbon sources revealed 53 open reading frames (ORFs), including genes of the glycolysis, as Gcr1p dependent.

This description of some transcription factors and of the Snf1p and Mig1p pathway should give a short overview of some players in the glucose repression network. It should be noticed that there are more regulatory cycles than the Snf1p-pathway for glucose repression. Although a broad knowledge on glucose sensing and signalling has been achieved the last 20 years, major questions still remain unanswered: what is the nature of the glucose signal and how are the known signalling pathways regulated and integrated.

A limited number of yeast species is able to grow on methanol as sole carbon and energy source. They are belonging to one of the four genera *Pichia, Hansenula, Candida* and *Torulopsis* and share a general methanol utilisation pathway which is expressed after derepression or induction with methanol (see 1.3.1). Since initial reactions of this pathway are compartmentalised within peroxisomes, these organelles are also induced. Due to the strong induction of peroxisomes, the yeasts *Candida boidinii, Pichia methanolica, Pichia pastoris* and *Hansenula polymorpha* were frequently used in cell biology to study peroxisome biogenesis and function.

As mentioned above methylotrophic yeasts share a common methanol utilisation pathway. The first step is the oxidation of methanol to formaldehyde and hydrogen peroxide, catalysed by alcohol oxidases (AOX, EC 1.1.3.13). The toxic $H_2O_2$ is disarmed to oxygen and water by the action of catalase. Both enzymes are sequestered in peroxisomes. Formaldehyde is either oxidised by two subsequent dehydrogenase reactions or assimilated in the cell metabolism by the condensation with xylulose 5-phosphate (Xu5P). Formaldehyde is oxidised to formate and further on to carbon dioxide by a glutathione (GSH)-dependent formaldehyde dehydrogenase and a formate dehydrogenase, both localised in the cytosol. NADH, generated in both reactions, is used to produce energy for growth on methanol. The condensation reaction takes place within the peroxisomes and is catalysed by the above mentioned transketolase dihydroxyacetone synthase. The resulting C3-compounds dihydroxyacetone (DHA) and glyceraldehyde 3-phosphate (GAP) are further metabolised in the cytosol. After a phosphorylation of DHA, fructose 1,6-bisphosphate (FBP) is formed by an aldolase reaction of dihydroxyacetone phosphate (DHAP) and GAP. FBP is converted to fructose 6-phosphate by a phosphatase and xylulose 5-phosphate (Xu5P) is regenerated in the pentose phosphate pathway. One third of the GAP generated enters the gluconeogenesis pathway for cell constituent synthesis.

The key enzymes of the methanol utilisation pathway, alcohol oxidase and formate dehydrogenase, are produced at very high levels after induction with methanol. Alcohol oxidase can account for more than 30% of the total soluble protein, dihydroxyacetone synthase and formate dehydrogenase up to 20%. The peroxisomes, which are also induced, can account for about 80% of the cell volume. Promoter sequences of several methanol utilisation genes were developed for recombinant protein production. Among others, these strong and inducible promoters are a main reason for the wide use of *Pichia pastoris* and *Hansenula polymorpha* as protein production hosts.

In *H. polymorpha* and *C. boidinii* one gene encodes for an alcohol oxidase: MOX (methanol oxidase, *H. polymorpha*) and AOD1 (alcohol oxidase, *C. boidinii*). 2 genes were found in the two *Pichia* species *P. pastoris* (AOX1 and AOX2) and *P. methanolica* (AUG1 and AUG2, alcohol utilising gene, or MOD1 and MOD2), with Aox 1p and Aug1p being the main alcohol oxidase. Comparison of coding regions revealed 73-85% similarity on the amino acid level between the methylotrophic yeasts [1]. The homology between the *P. pastoris* AOX1 and AOX2 ORFs (open reading frames) is 92% and 97% on the nucleotide and the amino acid sequence levels, respectively [2,3]. Alcohol oxidase is an octameric flavoprotein containing one non-covalently bound FAD or a modified analogue (mFAD) per subunit. AOX translation occurs on free ribosomes followed by a posttranslational import into peroxisomes. Translocation into peroxisomes is targeted by a PTS1 (type 1 peroxisome targeting signal) sequence at its extreme C-terminus. Aox oligomers are formed only after the import into the peroxisomal matrix.

In *C. boidinii* and *P. pastoris* no Aox oligomers could be found in the cytosol in contrast to the dihydroxyacetone synthase, which forms a dimer in the cytosol prior to its translocation into the peroxisomal matrix. Not only the alcohol oxidase 1 promoter sequence of *Pichia pastoris*, but also the enzyme is of biotechnological interest due to a broad substrate range (unsaturated and saturated primary alcohols with short to moderate chain length) and a high stability under various reaction conditions. Regulation of all alcohol oxidase genes occurs on the transcription level and most probably at the transcription initiation stage. Although AOX1 and AOX2 are regulated similarly (mRNA not detectable on glycerol or glucose, detectable at carbon starvation phase, high amounts on methanol), their 5-flanking regions share no significant homology [2, 4].

Each AOX locus exhibits a putative RNA polymerase binding site (TATAAA; Goldberg-Hogness or TATA box) at position −43 relative to the primary transcription initiation site. Both P. pastoris AOX mRNA leader sequences are extremely rich in A residues and unusually long for yeasts (115 nucleotides (nt) for AOX1 and 160 nt for AOX2). The translation initiation regions around the ATG start codon (Kozak sequence; AOX1: CGAAACG ATG GCT, AOX2: GAGAAAA ATG GCC) are consistent with previously described consensus sequences for *S. cerevisiae* and higher eukaryotes. The physiological role of the second alcohol oxidase gene in P. pastoris and *P. methanolica* is still obscure. Disruption of AOX1 or AUG1 causes severe growth defects in these strains (the so-called methanol utilisation slow (Mut$^s$) phenotype) while aox2 and aug2 strains show comparable growth rates to the wild-type strain. 9 multiple forms of alcohol oxidase were observed in *P. methanolica* representing a random oligomerisation of the 2 gene products Aug1p and Aug2p. AUG1 and AUG2 are regulated differentially: at carbon starvation and low methanol concentration only Aug1p could be detected, and with increasing methanol concentration the Aug2p to Aug1p ratio increases. The shift to octamers with elevated Aug2p content is due to an increase in AUG2 expression, regulated on the transcription level. Km values for methanol of the two homooctamers of Aug1p and Aug2p are about 0.56 an 5.6 mM, respectively. Together with the finding, that disruption of AUG1 causes a growth defect at low methanol concentrations [5], these results implicate that AUG2 is an advantage for *P. methanolica* when growing at higher methanol concentrations. In *Pichia pastoris* neither the role of the AOX2 gene was analysed in further detail nor were favourable conditions for possessing a second alcohol oxidase gene found. Since laboratory conditions represent only a very small fraction of conditions free-living microorganisms are confronted, there should be situations in nature where the AOX2 gene is of selective importance to *P. pastoris*.

*C. boidinii* AOD1 and *H. polymorpha* MOX expression is strictly repressed during growth on glucose or ethanol as sole carbon source, derepressed on glycerol and strongly induced on methanol. Expression of these two enzymes is also repressed when glucose and methanol are present in the medium. If glycerol is present methanol is able to induce gene expression. Transcription of AOD1 and MOX is also derepressed at carbon starvation and repressed when ethanol is present [6-9]. Two distinct regulatory mechanisms are responsible for repression of the methanol utilisation metabolism by ethanol or glucose [10,11]. In *Pichia pastoris* the situation is significantly different: AOX1 is repressed when glucose, ethanol or glycerol is present in the media (in non-growth limiting concentrations). Derepression at carbon starvation and induction by methanol are similar to AOD1 and MOX. Carbon sources with which AOX1 expression is derepressed are e.g. sorbitol, mannitol, trehalose and alanine [12].

Upon shift from methanol to a repressing carbon source like glucose or ethanol, peroxisomes are degraded within hours during adaptation to the new carbon source. Proteolytic degradation in the yeast vacuole again follows two distinct mechanisms when adapted to glucose or ethanol, called micro- and macroautophagy, respectively.

As mentioned above, the methylotrophic yeasts *Pichia pastoris* and *Hansenula polymorpha* are widely used for recombinant protein production. Up to now, more than 500 proteins have been produced in *P. pastoris*. Their development was driven by a few characteristics, which brings them advantages among recombinant expression hosts: 1) they share the general advantages of yeasts in terms of genetic manipulation and cultivation technology (laboratory- and large-scale); 2) the ability to grow to extremely high cell densities; and 3) the high-level production of recombinant protein (secreted or intracellular). The strong inducible promoters of genes encoding for reactions of the methanol utilisation pathway were developed for recombinant protein production. The most widely used ones are the promoter regions of the alcohol oxidase genes AOX1 and MOX of *P. pastoris* and *H. polymorpha*, respectively. But also other promoter regions of the methanol utilisation pathway genes were used to drive recombinantprotein production: FMD (formate dehydrogenase) and DAS1 (dihydroxyacetone synthase) promoters in *H. polymorpha* and *C. boidinii* and the FLD1 (formaldehyde dehydrogenase) promoter in *P. pastoris*. The latter one can also be induced with methylamine as sole nitrogen source with glucose as a carbon source. Promoters for constitutive expression of foreign genes are also available: the GAP (glyceraldehyde 3-phosphate dehydrogenase) promoter element in *P. pastoris* and the PMA1 (encoding for the plasma membrane H+-ATPase) promoter in *H. polymorpha*. Several auxotrophic host strain/marker gene-combinations were developed for *P. pastoris* (e.g. HIS4) and *H. polymorpha* (e.g. LEU2 and URA3). Dominant selection markers are also available (e.g. ZEOCIN™, G418 resistance). Gene integration into methylotrophic yeasts is done mainly (if not exclusively) by homologous integration. Vectors bearing an ARS (autonomously replicating sequence) region are also available but they are usually quite unstable if selection pressure is released which results in their limited technological application. In *P. pastoris* the foreign gene is integrated site-specifically either in the AOX1 or the HIS4 locus. Other possible integration sites are e.g. the GAP locus (for GAP expression) or any other selection marker loci (e.g. ADE1, URA3, ARG4 and LEU2). In *H. polymorpha* expression cassettes are randomly integrated in a head-to-tail arrangement leading to mitotically stable integrants with a high copy-number (up to 100). However, a high copy-number often does not result in a high-level expression. Additional factors of great influence are: structure of the integration cassette, nature and structure of the protein to be expressed and the integration site. Especially the integration cassette structure is of great influence on the effect of gene dosage. A further discussion how to optimise the expression cassette and the gene dosage is given in [13,14]. Methylotrophic yeasts are belonging to the group of Crabtree negative yeasts thus ethanol production occurs at very low level when grown under aerobic conditions. Due to this fact these yeasts can be grown to very high cell densities in fermentor cultures resulting in high product yields. AOX1 driven protein production can be further increased 3-5 times when the methanol concentration in the bioreactor is in growth-limiting spheres. The fact that *P. pastoris* secretes under standard conditions only low amounts of endogenous proteins makes every secreted recombinant protein the most abundant in the medium. Secretion can serve as a substantial first step in the down-stream purification process. For protein secretion, the *S. cerevisiae* MFα1 (mating factor α) prepro leader sequence and sequences derived from the acid phosphatase (PHO1) are widely used in *P. pastoris* and *H. polymorpha*. In some cases sufficient secretion was obtained with plant, fungal and mammalian proteins bearing their natural secretion signals. As mentioned above, yeasts are capable of performing posttranslational modifications like disulfide bond formation, processing of signal sequences (e.g. prepro leader sequence of MFα), lipid addition and N- and O-linked glycosylation. While in mammalian cells highly complex N- and O-linked oligosaccharide-structures composed of a variety of sugars (e.g. N-acetylglucosamine, galactose, and sialic acid) are produced, most yeasts generate high mannose type structures lacking some sugar entities like galactose or sialic acid. These non-mammalian structures can result in severe problems for therapeutic application mainly due to their high potential immunogenicity. In *H. polymorpha* and *P. pastoris*, in contrast to *S. cerevisiae*, hypermannosylation is less abundant and no hyperimmunogenic terminal α–1,3-linked mannoses are incorporated in N-linked oligosaccharides. To overcome the problems of immunogenicity (and some others like low stability in the blood flow) efforts are on the way to humanize yeast-derived oligosaccharide structures, and, as recent literature reveals, especially in *P. pastoris*. To date, the vast majority of research issues and commercial processes rely on the well known yeast *S. cerevisiae*. Due to increasing knowledge about non-conventional yeasts, together with the apparent advantages in terms of large-scale fermentation and glycosylation issues, *H. polymorpha* and *P. pastoris* are rapidly becoming the yeast of choice. This is emphasised by the fact that several production processes were implemented in industry.

In the WO 02/081650 the identification of AOX1 promoter regions is disclosed, which may be used for the construction of mutant AOX1 promoters. Since the deleted sequence regions of the AOX1 promoter disclosed therein are very long, the accumulated effect and not the single effects of the distinct regulatory sequences of the promoter can be observed. However, such an approach will not allow the development of strongly enhanced promoters. Especially when constructing new promoters having enhanced features by deleting or duplicating parts of the original promoter the knowledge of the exact regulatory sequence range is required.

It is an object of the present invention to provide an improved AOX1 promoter with enhanced properties in order to facilitate downstream processing in protein production, to increase time-space-yields and to help to upgrade product quality.

Another object is to provide a strong AOX1 promoter in a vector or a host strain which anticipates partly or entirely glucose repression. It is of advantage to have a promoter which drives strong expression in presence of high glucose concentrations.

A further object of the present invention is to provide an AOX1 promoter which allows the production of a protein employing a reduced amount of methanol or without methanol. Such promoters would have a significant impact on industrial production processes. Due to safety issues special equipment is needed for production plants employing methanol as an inductor. This contradicts *Pichia pastoris* applications in many less specialised production plants. In addition protein stability in presence of methanol can hamper methanol based induction of protein expression. This is less critical for the production of robust industrial proteins, but becomes a major issue for e.g. secreted therapeutical proteins.

The construction of such promoters requires the knowledge of specific portions (e.g. regulatory elements, transcription factor binding sites) of the wild-type *Pichia pastoris* AOX1 promoter which—when mutated somehow—show an effect on the expression behavior. Therefore it is an object of the present invention to identify these portions and to provide therefore the means to create AOX1 promoters with enhanced features.

Therefore the present invention relates to a mutant *Pichia pastoris* alcohol oxidase 1 (AOX1) promoter of the wild type *Pichia pastoris* AOX1 promoter (SEQ ID No. 1) comprising at least one mutation selected from the group consisting of:
 a) a transcription factor binding site (TFBS),
 b) nucleotides 170 to 235 (−784 to −719), nucleotides 170 to 191 (−784 to −763), nucleotides 192 to 213 (−762 to −741), nucleotides 192 to 210 (−762 to −744), nucleotides 207 to 209 (−747 to −745), nucleotides 214 to 235 (−740 to −719), nucleotides 304 to 350 (−650 to −604), nucleotides 364 to 393 (−590 to −561), nucleotides 434 to 508 (−520 to −446), nucleotides 509 to 551 (−445 to −403), nucleotides 552 to 560 (−402 to −394), nucleotides 585 to 617 (−369 to −337), nucleotides 621 to 660 (−333 to −294), nucleotides 625 to 683 (−329 to −271), nucleotides 736 to 741 (−218 to −213), nucleotides 737 to 738 (−217 to −216), nucleotides 726 to 755 (−228 to −199), nucleotides 784 to 800 (−170 to −154) or nucleotides 823 to 861 (−131 to −93) of Seq ID No. 1, and combinations thereof. The (negative) numbers in parenthesis throughout the description reflect the corresponding positions of the promoter in relation to the translation start codon (e.g. ATG). For instance, "A" of "ATG" in a nucleic acid sequence comprising $N_xGACTATGN_y$ corresponds to the position +1, whereas "T" before "A" of "ATG" corresponds to position −1.

According to the present invention the mutant AOX1 promoter comprises at least one mutation within a transcription factor binding site and/or one of the nucleic acid sequence ranges outlined above. It turned out that especially these regions of the AOX1 promoter are suited to modify said promoter in order to alter its features. Of course also a combination of the mutations outlined above may be introduced to enhance the characteristic features of an AOX1 promoter (e.g. two TFBS mutations selected from a), one TFBS mutation selected from a) and one mutation selected from b), one mutation selected from a) and two mutations selected from b)). For instance, a mutation of a TFBS may be combined with a mutation within nucleotides 737 to 738 (−217 to −216) and/or nucleotides 207 to 209 (−747 to −745) of Seq ID No. 1. The expression of a protein under the control of an AOX1 promoter in *Pichia pastoris* is induced generally by the addition of methanol and inhibited by the presence of glucose in the medium. In order to enhance or to reduce the effect of said medium additives on the protein expression, the promoter is preferably mutated in the promoter regions as outlined above. The efficacy of the mutated AOX1 promoters to produce a protein of interest varies depending on the amount (i.e. copies) of vector integrated into the chromosome of the host. Especially multicopy strains turned out to show enhanced promoter effects. Since the antibiotic resistance of *Pichia* strains depends on the number of antibiotic resistance cassettes (vectors introduced into a host comprise preferably an antibiotic resistance cassette allowing the host to grow on/in a medium comprising an antibiotic as selective marker) integrated into the chromosome of said host, multicopy strains may be produced by applying increasing concentrations of antibiotic (within the range of 10 μg/ml to 10 mg/ml, preferably 50 μg/ml to 1000 μg/ml; depending on the antibiotic used; for instance, geneticin: 0.1 to 10 mg/ml, preferably 0.2 to 5 mg/ml, particularly 0.25 to 4 mg/ml, ZEOCIN™: 10 to 5000 μg/ml, preferably 50 to 3000 μg/ml, particularly 100 to 2000 μg/ml) onto the selective agar plates to increase the selection pressure (e.g. [14]; Scorer, C. A. et al. (1994) Bio/Technology 12:181-184). However, it was found that the growth of cells harbouring a multiplicity of antibiotic resistance cassettes is not only dependent on the concentration of the antibiotic but also time dependent. Therefore, multicopy strains are able to grow to a detectable colony on a medium containing the same concentration of antibiotic in a shorter period of time than singlecopy strains. This behaviour enables the person skilled in the art to detect and to isolate multicopy strains before singlecopy strains begin to grow. For instance, a strain harbouring one single copy of an antibiotic resistance cassette grows on an agar plate to a detectable colony size in 72 h, whereas the same strain harbouring more than one copy of said cassette grows in 24 to 48 h to the same size.

Especially multicopy strains harbouring an AOX1 promoter with mutations within nucleotides 694 to 723 (−260 to −231) and within nucleotides 737 to 738 (−217 to −216) showed surprisingly enhanced expression rates.

In order to increase the protein expression efficiency of a host in the presence of methanol, nucleotides 170 to 235 (−784 to −719) of the AOX1 promoter (SEQ ID No. 1) are preferably mutated. A mutation in this region increases the protein expression to 120 to 130% compared to the wild type AOX1 promoter, provided that the plasmid carrying the mutant AOX1 promoter is only once integrated into the chromosome/genome of the host (single copy mutant). However, mutations within all other above mentioned regions reduce or does not affect the efficacy of methanol to induce protein expression. In contrast thereto, mutations in the promoter regions of the wild type AOX1 promoter (as outlined above) lead—depending on the mutation—to increased and decreased protein expression under derepression conditions (e.g. see Table 13, example 1).

However, recombinant strains harbouring more than one copy of mutated AOX1 promoters result in strains having an enhanced activity under derepression and methanol induced conditions (multicopy strains, e.g. see FIG. 7, example 2). In detail, multicopy strains harbouring mutations within nucleotides 694 and 723 of SEQ ID No. 1 (d6), within nucleotides 694 and 723 (−260 and −231) of SEQ ID No. 1 (d6), within nucleotides 694 and 723 (−260 and −231) and within nucleotides 304 and 350 (−650 and −604) of SEQ ID No. 1 (d2d6), within TFBS, especially within Rap1, Gcr1, QA-1F, Hsf_1, Adr1, Hsf_2, Mat1MC, abaA and Hap2345, show an increased expression under derepression conditions and/or under methanol induction compared to the expression of proteins under the control of the wild type AOX1 promoter. Under derepression conditions some of these multicopy strains show protein expressions which are about 10 fold increased compared to expressions under the control of the wild type promoter. In presence of methanol as inductor the expression efficiency is more than 5 times enhanced when a promoter according to the present invention is employed. Therefore, these mutations, especially when present in the host in a multicopy form, are preferably employed for the expression of proteins. The combination of two or more of the above mentioned mutations may further enhance the promoter strength (see e.g. FIG. 7, example 2).

The transcription factor binding sites may be identified experimentally (e.g. by mobility shift or footprint analysis) or by sequence comparison with known transcription factor binding sites (e.g. by computer analysis, [15]).

The knowledge of promoter regions which influence the strength and the characteristics of said promoter may be used to design promoters with distinct properties (high protein expression under derepression conditions and/or high protein expression in presence of methanol). Furthermore these properties may be enhanced or altered if these mutant promoters are integrated one or more times into the genome of the host (e.g. see examples 1 to 3).

However, in some cases the promoter activity should be decreased instead of increased. Especially the co-expression of regulatory proteins like kinases, phosphorylases and helper proteins, such as e.g. chaperones, protein disulfide isomerase, cis-trans isomerases, foldases, protein disulfide isomerases and proteases, is in many cases required to be low in comparison to the main product, which may be produced by the cell under the wild-type promoter or under an enhanced promoter according to the present invention. Especially the combined expression of two different products (e.g. a helper protein and the main product) under the control of an AOX1 promoter with increased activity and an AOX1 promoter with decreased activity (in comparison to the wild-type activity), respectively, turned out to be advantageous, because the expression rate of the main and the secondary product differs even more instead of using wild-type AOX1 promoters. Reduced expression may be preferably obtained by deleting activator binding sites like HSF or HAP or by inserting repressor binding sites into the wild-type AOX1 promoter. Hence, the use of AOX1 promoter with reduced activity prevents the overloading of the protein expression machinery of the cell, which would have the consequence, that the yield of the main product would be reduced. For instance, Bessette P H et al. (PNAS USA (1999) 96:13703-13708) could show that the expression of an active polypeptide could be increased significantly by the co-expression of a thioredoxin.

According to a preferred embodiment the promoter comprises further a mutation within nucleotides 694 to 723 (−260 to −231) and/or nucleotides 729 to 763 (−225 to −191) of Seq ID No. 1.

A mutation affecting these nucleotide ranges in combination with a mutation as outlined above results in even more enhanced promoter activity. For instance, a double mutation affecting nucleotides 694 to 723 (−260 to −231) and nucleotides 737 to 738 (−217 to −216) of Seq ID No. 1 lead to a promoter showing higher expression levels under derepression as well as under induced conditions compared to the expression levels under the same conditions of the wild type promoter. The effect of this double mutation can be enhanced when the nucleic acid comprising the promoter is introduced in the cell in more than one copy (resulting in a multi copy clone).

The mutation is preferably a deletion, a substitution, an insertion, an inversion and/or a multiplication.

In order to modify the characteristics of the wild type AOX1 promoter of *Pichia pastoris* several mutation types are possible. The promoter stretches comprising the above mentioned regions (transcription factor binding sites (TFBS), nucleotides 170 to 235 (−784 to −719), 170 to 191 (−784 to −763), 192 to 213 (−762 to −741), 192 to 210 (−762 to −744), 207 to 209 (−747 to −745), 214 to 235 (−740 to −719), 304 to 350 (−650 to −604), 364 to 393 (−590 to −561), 434 to 508 (−520 to −446), 509 to 551 (−445 to −403), 552 to 560 (−402 to −394), 585 to 617 (−369 to −337), 621 to 660 (−333 to −294), 625 to 683 (−329 to −271), 694 to 723 (−260 to −231), 729 to 763 (−225 to −191), 736 to 741 (−218 to −213), 737 to 738 (−217 to −216), 726 to 755 (−228 to −199), 784 to 800 (−170 to −154) or 823 to 861 (−131 to −93) of Seq ID No. 1) may be partially or completely deleted, partially or completely substituted with other nucleotides or nucleic acid sequences, disrupted by insertion of single nucleotides or nucleic acid sequences, inverted partially or completely or multiplied. All these mutations lead to a change in promoter activity, because structural features and/or recognition/binding sites for e.g. transcription factors are affected by said mutations. However, these changes may lead to an increased or decreased activity of the promoter compared to the wild type promoter.

It is well known in the prior art that the multiplication/duplication of specific nucleic acid stretches may increase the promoter activity. The regulation of gene expression of many eukaryotic promoters, especially yeast promoters, involves multiple interactions between transcription factors bound within a promoter. Multiple sites may be required for the functioning of even the smallest cis-acting elements. In yeast cells, upstream activator sequences (UAS) are necessary for transcription. They work in either orientation and at variable distance with respect to the TATA box and transcription start site, but in contrast to enhancers in higher eukaryotes, they must be upstream from these basal elements. UAS are targets of several transcriptional activators.

Most repression phenomena in yeast cells result from the inactivation or absence of transcription factors. However, some negative regulatory sites (upstream repression sequences (URS)) could also be identified.

Based upon deletion analysis of the *P. pastoris* AOX2 promoter three regulatory regions were found, two negative acting regions (URS1 and URS2) and a positive acting domain (UAS) [3]. For the *H. polymorpha* MOX promoter two upstream activating sequences (UAS1 and UAS2) and one repressor binding site (URS1) were also described [8]. Corresponding sequences could also be identified on AOX1 promoters (nucleotides 585 to 614 (−369 to −340) and 725 to 756 (−229 to −198), showing similarities to AOX2 UAS [3], as well as nucleotides 622 to 656 (−332 to −298) [8]). The multiplication (2, 3, 4, 5, 6 or 7 times UAS) of these nucleic acid stretches may result in a promoter with an enhanced strength leading to even more powerful protein expression. Therefore the construction of promoters comprising multiple UAS, preferably involving the above mentioned sequence regions similar to the AOX2 and MOX UAS, or other multiple sequence stretches (e.g. the nucleic acid sequences ranges outlined above) falls also within the scope of the present invention and is considered to be a preferred embodiment. An activating sequence is usually within a few hundred basepairs of a promoter. For example, most activating sequences are within about 200 to 400 basepairs of the promoter that is enhanced. Further upstream the promoter usually contains further enhancers and transcription factor binding sites.

At least one mutation of the AOX1 promoter may be introduced by standard methods known to a person skilled in the art (e.g. Molecular Cloning: A Laboratory Manual (Third Edition), J. Sambrook and D. Russell, 2001, Cold Spring Harbor Laboratory Press).

According to a preferred embodiment of the present invention the transcription factor binding site (TFBS) is selected from the group consisting of Hap1, Hsf, Hap234, abaA, Stre, Rap1, Adr1, Mat1MC, Gcr1 and QA-1F.

The mutation of at least one of these TFBS results in mutant promoters with varying characteristics (see example 2).

(−437) to 524 (−430) of Seq ID No. 1, Hap234 nucleotides 196 (−758) to 200 (−754), 206 (−748) to 210 (−744) and 668 (−286) to 672 (−282) of Seq ID No. 1, abaA nucleotides 219 (−735) to 224 (−730) of Seq ID No. 1, Stre nucleotides 281 (−673) to 285 (−669) of Seq ID No. 1, Rap1 nucleotides 335 (−619) to 339 (−615) of Seq ID No. 1, Adr1 nucleotides 371 (−583) to 377 (−577) of Seq ID No. 1, Mat1MC nucleotides 683 (−271) to 687 (−267) of Seq ID No. 1, Gcr1 nucleotides 702 (−252) to 706 (−248) of Seq ID No. 1 and QA-1F nucleotides 747 (−207) to 761 (−193) of Seq ID No. 1.

These TFBS may be identified experimentally or by comparison with known TFBS of other promoters (e.g. promoters of eukaryotes) with the assistance of computer programmes (e.g. see example 1).

A summary of the influence of mutant AOX1 promoters on the expression of proteins, peptides or functional nucleic acids is provided in table 2 (in comparison to the wild-type activity).

TABLE 2

Influence of mutants of the wild-type AOX1 promoter on the expression of proteins, peptides or functional nucleic acids

| Mutation | Singlecopy clone | | Multicopy clone | |
|---|---|---|---|---|
| | Derepression condition[1] | Methanol induced condition[1] | Derepression condition[1] | Methanol induced condition[1] |
| ΔHap1 | | + | | |
| ΔHsf_1 | − | + | + | + |
| Δ1 | + | + | | |
| ΔHap2345_1 | | + | | + |
| ΔHap2345_2 | − | + | | + |
| ΔabaA | − | | + | + |
| ΔStre | + | + | | |
| Δ2 | | − | | |
| ΔRap1 | − | | + | + |
| Δ3 | − | − | | |
| ΔAdr1 | − | − | + | + |
| Δ4 | − | − | | |
| ΔHsf_2 | | | | |
| Δ5 | − | − | | |
| ΔHap2345_3 | | | + | + |
| ΔMat1MC | | | | |
| Δ6 | + | + | + | + |
| Δ6* | + | − | + | + |
| ΔGcr1 | − | + | + | + |
| Δ7 | − | − | | |
| ΔQA-1F | + | | + | + |
| ΔQA-1Fzus | + | − | | |
| Δ Hsf_2_dHap 2345_1 | | + | + | + |
| Δ Hsf_2_dHap 2345_1zus | | + | | |
| ΔHsf_2_Mat1MC | − | | + | + |
| Δ8 | − | − | | |
| Δ9 | − | − | | |
| Δ2Δ6 | | − | + | + |
| Δ736-41 | | − | | |
| Δ737-38 | | | | |
| ΔInD-d4m | | | | |
| ΔD-d4 | | | | |
| Δ1-1 | | | | |
| Δ1-2 | | | | |
| Δ1-3 | | | | |
| Δ1-SacI | | | | |

[1]Expression rate in comparison to the wild-type AOX1 promoter: − decreased, + increased Preferably, the transcription factor binding site (TFBS) Hap1 comprises nucleotides 54 (−900) to 58 (−896) of Seq ID No. 1, Hsf nucleotides 142 (−812) to 149 (−805) and 517

Another aspect of the present invention relates to a nucleic acid molecule comprising a mutant *Pichia pastoris* alcohol oxidase 1 (AOX1) promoter according to the present invention and a nucleic acid encoding a protein, peptide or functional nucleic acid, wherein the promoter and said nucleic acid are operably linked together.

The mutant AOX1 promoter can be linked to a gene encoding for a protein (e.g. enzyme), a peptide (e.g. hormone) or functional nucleic acid (e.g. siRNA). The resulting nucleic acid fragment may be used to express e.g. a protein when introduced into an organism, preferably a yeast, especially a *Pichia pastoris* strain. The construction of said nucleic acid molecule is well known to the person skilled in the art and can be performed with standard molecular biological methods (e.g. Molecular Cloning: A Laboratory Manual (Third Edition), J. Sambrook and D. Russell, 2001, Cold Spring Harbor Laboratory Press; manual "*Pichia* Expression Kit", Invitrogen Corp.).

"Operably linked" refers to a first sequence(s) being positioned sufficiently proximal to a second sequencers) so that the first sequence(s) can exert influence over the second sequence(s) or a region under control of that second sequence. For instance, a promoter can be operably linked to a gene so that the gene will be expressed under the control of the promoter, which would typically be 5' to the gene. Usually, a core promoter would be within a few hundred base pairs from the start site of translation. About 30 bp downstream there is usually a downstream promoter element.

Another aspect of the present invention relates to a vector comprising a mutant *Pichia pastoris* alcohol oxidase 1 (AOX1) promoter according to the present invention or a nucleic acid molecule as outlined above.

In order to introduce the mutant promoter, optionally operably linked to a nucleic acid encoding for a protein, peptide or functional nucleic acid, into a host, preferably into a methylotrophic yeast strain (e.g. a *Pichia pastoris* strain), said promoter has to be provided in a vector, which may be used for the transformation of said host. For instance, said vectors may be yeast episomal plasmids (YEp), yeast integrative plasmids (YIp) or yeast artificial chromosomes. Such vectors comprise usually an origin of replication (if amplification in microbial hosts is needed) and a selection marker for the propagation of the vectors in *E. coli*, promoters and terminators for the recombinant protein expression in yeast and selection markers for yeast. Non-integrative vectors further comprise an autonomous replicating sequence (ARS), which ensures the stability of the vector in the cell (e.g. Myers, A. M., et al. (1986) Gene 45: 299-310). Integrative vectors, which do not harbour AR sequences, comprise sequence regions which are homologous to regions of the genome. Alternatively linear DNA, e.g originating from PCR can be used for transformation.

Another aspect of the present invention relates to a cell comprising at least one mutant *Pichia pastoris* alcohol oxidase 1 (AOX1) promoter, at least one nucleic acid fragment or at least one vector as disclosed herein. The introduction of a nucleic acid molecule harbouring a mutant AOX1 promoter (e.g. vector, wherein the promoter is operably linked to a nucleic acid encoding for a protein) into a host may be done e.g. by electroporation. Said nucleic acid molecule is integrated into the chromosome after its introduction into said host in a single copy or in multiple copies or present in the cell as a single copy or multicopy autonomous replicating plasmid. If several mutant promoters are used, they can all be linked with one single gene (coding for a protein or functional nucleic acid (e.g. Ribozyme, antisense RNA etc.), an identical protein or different proteins (e.g. 1 promoter variant is linked to a selection marker and another mutant promoter is linked to another protein which should be expressed). Therefore within the scope of the present invention singlecopy strains comprising one copy of the AOX1 promoter operably linked to a nucleic acid encoding for a protein, a peptide or a functional nucleic acid as well as multicopy strains comprising more than one, preferably at least 2, 3, 4, 5, 6, 7, 8, 9, 10, 15 or 20 copies of the AOX1 promoter operably linked to a nucleic acid encoding for a protein, a peptide or a functional nucleic acid are preferably produced.

According to a preferred embodiment of the present invention said cell is a eukaryotic cell, in particular a yeast cell, preferably a methylotrophic yeast cell.

Preferably the methylotrophic yeast cell is selected from the group consisting of *Candida, Hansenula, Pichia* and *Toruplosis*, especially a *Pichia pastoris* cell.

AOX1 promoters as well as mutated variants therefrom may be functionally introduced in a very large number of different yeast cells, including methylotrophic (e.g. *Pichia pastoris*) and non-methylotrophic (e.g. *Saccharomyces cerevisiae*) cells. The transferability of promoters to other organisms, especially of AOX1 and MOX promoters, is known to the person skilled in the art. Although the substrate specificity and some regulatory features are different in different yeasts (e.g. *Pichia pastoris, Hansenula polymorpha* and *Saccharomyces cerevisiae*) a recognition of foreign promoters was demonstrated (e.g. Raschke, W. C., et al., Gene, 1996. 177: 163-7; Pereira, G. G. and C. P. Hollenberg, Eur J Biochem, 1996. 238:181-91). For instance, the *H. polymorpha* MOX promoter is recognised in *S. cerevisiae*, repressed in presence of glucose and de-repressed under carbon source limitation. Similarly the AOX1 promoter can be employed in *H. polymorpha* and is regulated in the same way as the MOX promoter. The ZZA1 promoter, which is closely related to the AOX1 promoter could also be successfully employed in *S. cerevisiae*.

Another aspect of the present invention relates to a kit for the expression of a selected protein or transcription to a functional RNA, comprising
  i) a vector as defined above, and
  ii) a cell capable to express said protein or functional RNA under the control of a promoter according to the present invention.

The vector according to the present invention can be used in a kit for the expression of a selected protein or transcription of a functional RNA (e.g. ribozyme, antisense RNA, RNAi).

According to a preferred embodiment of the present invention said cell is a yeast cell, preferably a methylotrophic yeast cell.

Preferably the methylotrophic yeast cell is selected from the group consisting of *Candida, Hansenula, Pichia* and *Toruplosis*, especially a *Pichia pastoris* cell.

Another aspect of the present invention relates to a method for the expression of a recombinant protein, peptide or functional nucleic acid in a cell comprising the following steps:
  providing a vector or a nucleic acid molecule comprising an AOX1 promoter according to the present invention and a nucleic acid encoding for a protein, peptide or functional nucleic acid, said promoter being operably linked to said nucleic acid,
  transforming said cell with said vector or said nucleic acid molecule,
  culturing the transformed cell in a suitable culture medium,
  optionally inducing expression of said protein, peptide or functional nucleic acid and
  isolating said expressed protein, peptide or functional nucleic acid.

According to a preferred embodiment of the present invention said cell is a yeast cell, preferably a methylotrophic yeast cell.

Preferably the methylotrophic yeast cell is selected from the group consisting of *Candida, Hansenula, Pichia* and *Toruplosis*, especially a *Pichia pastoris* cell. Another aspect of the present invention relates to the use of a nucleic acid molecule, a vector or a cell according to the present invention for the expression of a protein, peptide or functional nucleic acid.

When a nucleic acid molecule, a vector or a cell according to the present invention is used for the expression of a protein, peptide or functional nucleic acid it is advantageous to choose an appropriate AOX1 promoter which fulfils the requirements posed for the expression (e.g. high or constitutive expression under derepression conditions (=without the addition of glucose to the medium) or under methanol induced conditions). Suitable mutant AOX1 promoters can be selected with the help of table 2.

Another aspect of the present invention relates to a method for the isolation of super expression clones comprising the steps:

a) introducing a nucleic acid molecule or vector comprising a mutated methanol inducible promoter, preferably an AOX1 promoter, operably linked to a nucleic acid encoding for a protein or to a functional nucleic acid and a marker resistance gene into a cell, b) transferring the cell of step a) to a medium comprising an appropriate selective marker, a non-repressing carbon source and methanol for the selective growth of super expression clones under inducing conditions or to a medium comprising an appropriate selective marker and a non-repressing carbon source without methanol for the selective growth of super expression clones under derepressing conditions, c) incubating the cell from step b) on said medium, d) isolating a colony of the cell obtained from step c) and e) detecting super expressing clones by determining the expression rate of said cell.

The construction of super or high expression clones harbouring a vector or a nucleic acid comprising a mutated methanol inducible promoter requires methods enabling the person skilled in the art to isolate these clones. Such a method is provided herein. The first step of said method is the introduction of the promoter comprising nucleic acid (e.g. vector) into a suitable cell, which is able to regulate said promoter. The promoter itself may be mutated by genetic engineering or by chemical (e.g. bisulfite, nitrite, fumaric acid, hydrazine) or physical (e.g. radiation, especially UV radiation) mutagenesis. In a further step the cells harbouring said mutated promoter are transferred to a medium, preferably to a solid medium directly or via a liquid medium, which comprises an antibiotic (e.g. ZEOCIN™) and sorbitol (or another non-repressing carbon source as described, e.g. in [12], in particular alanine, mannitol or trehalose) for the growth of high expression clones under derepression conditions and which comprises further methanol, if high expression clones under induced conditions should be discovered. By including glucose to the media together with methanol glucose non-repressed and methanol induced transformants might be isolated (to prevent methanol volatilization the medium may be stored during incubation in a methanol saturated or methanol comprising atmosphere). After the cultivation of the cells in or on a suitable medium, said cells are isolated from said medium and may be used for further analysis (e.g. determination of the exact expression rate, isolation of the promoter in order to analyse the changes in the nucleic acid sequence of the promoter compared to the wild type promoter). The non-repressing carbon sources used in the method according to the present invention and disclosed, e.g. in [12], are preferably employed in an amount of 0.1 to 10%, preferably in an amount of 0.2 to 5%, more preferably in an amount of 0.3 to 3%, in particular in an amount of 0.5 to 1%. A preferred non-repressing carbon source is selected from the group consisting of alanine, mannitol, sorbitol, trehalose, lactose and combinations thereof.

The selection of suitable marker resistance gene depends on the marker used to select transformants. For instance, if ZEOCIN™ is used as marker the marker resistance gene to be introduced into the vector under the control of the mutant AOX1 promoter is the Sh ble gene. If the nucleic acid encodes for a protein or a peptide the resulting/expressed protein may be a fusion protein. It is especially advantageous to provide the marker resistance gene under the control of the mutant AOX1 promoter, because in such a case the expression rate of the marker resistance gene product depends also on the promoter strength and behaviour of the mutated promoter. For instance, a strong promoter responsible for high expression of the nucleic acid product will also increase the expression rate of the marker resistance gene product. Such clones have a selective advantage over clones with a promoter exhibiting a reduced promoter strength. This allows the selection of super expression clones directly after the regeneration from the transformation of the cells.

The expression rate is preferably determined by methods like gel electrophoresis (e.g. SDS-PAGE), antibody binding (e.g. ELISA), quantitative (reverse transcriptase) PCR (e.g. real time RT-PCR), enzymatic activity (e.g. if the expressed protein is an enzyme) or fluorometrically (protein with a characteristic emission spectrum like green fluorescent protein).

Promoters (transformants) showing increased expression in absence of otherwise repressing C-sources (in the case of AOX1 promoter glucose) are selected by selective growth of transformed cells in/on media containing a non-repressing carbon source. Promoters (transformants) showing increased expression in absence of otherwise repressing C-sources (in the case of AOX1 promoter glucose) in presence of an inductor (e.g methanol) are selected by selective growth of transformed cells in/on media containing a non-repressing carbon source and the inductor (e.g. methanol). The inductor can also be a non-repressing carbon source. Superexpressing clones are selected by combining a multicopy leading to higher resistance against antibiotics (e.g ZEOCIN™) or higher productivity of an essential media component (e.g. Leu, H is, Arg, Ura) with the regulatory selection described above.

The media compositions to be used in a method according to the present invention may be obtained directly from manufacturers or distributors from kits, cells and vectors relating to *Pichia Pastoris* (e.g Invitrogen). The methanol concentration in the medium may be preferably 0.05 to 15%, more preferably 0.1 to 10%, particularly 0.3 to 5%. In the scientific literature different methanol concentrations for different cultivation conditions are described. For instance, shaking flasks may contain 1% methanol or less (Guarna M M, et al. (1997) Biotech. Bioeng. 56:279-286), fermentation processes may contain 0.5% methanol (Damasceno L M, et al. (2004) Protein Expr Purif 37:18-26; Hellwig S., et al. (2001) Biotechnol Bioeng 74:344-352; Hellwig S., et al. (1999) Biotechnol Appl Biochem 30:267-275).

The enhanced expression of multicopy clones may depend not only on the presence of more than one copy of mutated promoter in a cell but also due to the fact that there is a lack of several transcription factors, because these factors may be bound to the high number of transcription factor binding sites in said cell. This could be shown by comparison of the expression rate under methanol inducing conditions with the expression rate under derepression conditions wherein it could be found that the enhanced expression rate is not only an effect of the copy number of the mutated AOX1 promoter in the cell (no linear effect). For instance, strain d6*F10 shows such characteristics.

The medium used to isolate super expression clones may comprise further media components like leucine, uracil, arginine, histidine and/or adenine and sorbitol may be exchanged by glucose in order to identify promoter variants which show a reduced repression in the presence of glucose compared to wild-type promoter variants.

When auxotrophic strains are used, the cell may be transferred to a medium comprising sorbitol (or other no-repressing carbon sources) and containing individual media components (e.g. leucine, uracil, arginine, histidine and adenine) for the selective growth of super expression clones under derepressing conditions employing auxotrophy markers (step b)).

The commonly used P(TEF)-Zeo resistance marker in AOX1 promoter comprising vectors leads to constitutive expression of the ZEOCIN™ resistance protein and therefore allows the isolation of multicopy clones by resistance against higher concentrations of the antibiotic. The described new method allows to combine this effect with regulatory features to detect promoters and multicopy clones which lead to higher expression under certain controllable regulatory circumstances (e.g. derepressed expression, induced expression etc.). This makes it possible to dedect new promoters with altered regulatory properties and also clones where multicopy clones lead to enhanced expression under such special regulatory conditions.

"Super expression clones" are expression clones which express more of a protein or of a functional nucleic acid under the control of the mutated promoter than under the control of the wild type promoter or more of a protein or functional nucleic acid than by applying vectors with usually used promoter-selection marker combinations such as P(TEF)-Zeo. The expression rate of the "super expression clones" according to the present invention may be at least 20%, preferably at least 50%, more preferably at least 100%, particularly at least 500% increased compared to the expression rate of the same protein or peptide or functional nucleic acid under the control of the wild-type promoter (mean value plus two to three times standard deviation). "Super expression clones" may preferably comprise more than one copy of the mutated promoter or nucleic acid molecule according to the present invention. Alternatively, "super expression clones" may also be denominated "high expression clones".

According to the present invention "methanol inducible promoters" are promoters whose activity is regulated by the presence of methanol in the culture medium. Such promoters are preferably AOX1 (from *Pichia pastoris*) or MOX (from *Hansenula polymorpha*) promoters or any other methanol inducible and glucose repressed promoter derived from methylotrophic yeasts such as e.g. FMD, FLD, DAS (e.g. see table 6, example 1).

According to a preferred embodiment of the present invention the selective marker is an antibiotic, preferably ZEOCIN™.

The selective marker to be used in the medium depends on the fact which molecular characteristic of the cell can be used to distinguish a cell harbouring the nucleic acid or vector comprising a mutated or wild-type methanol inducible promoter from a cell which does not harbour said nucleic acid or vector. Selective markers may therefore be antibiotics (the genes for antibiotic resistance can be found in the vector or nucleic acid introduced in said cell). To compensate auxotrophy of certain strains the selective marker in the medium may be a substance like leucine, uracil, arginine, histidine and adenine, depending on the type of auxotrophy.

Preferably, the nucleic acid molecule, the vector and the cell are a nucleic acid, a vector and a cell according to the present invention.

According to a preferred embodiment of the present invention the nucleic acid molecule or vector is introduced into the cell by transformation by standard methods known to a person skilled in the art, preferably electroporation, chemical transformation, protoplast fusion or by particle bombardment (see e.g. Current Protocols in Molecular Biology, John Wiley & Sons, Edited by: Fred M. Ausubel et al.; Molecular Cloning: A Laboratory Manual (Third Edition), J. Sambrook and D. Russell, 2001, Cold Spring Harbor Laboratory Press).

The present invention is further illustrated by the following figures and examples without being restricted thereto.

FIG. 1 shows SDS-PAGE of GFP-Zeo expressing *P. pastoris* strains in microscale before induction with methanol (A) and 24 (B) and 72 (C) hours after induction. Samples were prepared as described in example 1 h). Lane 1 is X-33 (negative control), Lane 2-4 are X-33 GFP-Zeo strains Mut$^s$ A9, D2 and E2, Lane 5 is X-33 d6*F10. A strong band at 42 kDa is present in all GFP-Zeo clones.

FIG. 2 shows an overview of sequence deletions within the AOX1 promoter region and some transcription factor binding sites. Regions delta1-9 were deleted by overlap extension PCR.

FIG. 3 shows a bar chart of the fluorescence intensity of AOX1 promoter variants in microscale after derepression (carbon starvation). Cells were grown on 1% glucose in microscale. The data represents the mean ±SD of 4 independent measurements. RFU: relative fluorescence units; WT: *P. pastoris* strain GFP-Zeo D2 with GFP-Zeo under the control of the wild type AOX1 promoter; D1-D9: *P. pastoris* strains with deletion constructs AOX1Δ1-Δ9 in front of the GFP-Zeo gene; EX. excitation wavelength; EM: emission wavelength.

FIG. 4 shows a bar chart of the fluorescence intensity of AOX1 promoter variants in microscale after methanol induction. Cells were grown on 1% glucose in microscale. The data represents the mean ±SD of 4 independent measurements. RFU: relative fluorescence units; WT: *P. pastoris* strain GFP-Zeo D2 with GFP-Zeo under the control of the wild type AOX1 promoter; D1-D9: *P. pastoris* strains with deletion constructs AOX1Δ1-Δ9 in front of the GFP-Zeo gene; EX. excitation wavelength; EM: emission wavelength.

FIG. 5 shows a bar chart of the fluorescence intensity of selected AOX1 promoter variants in microscale. Expression levels under derepressing as well as inducing conditions of single copy strains and multicopy strains with wild type and Δ6 promoter variants are shown. The data represents the mean ±SD of 4 independent measurements. WT: single copy GFP-Zeo strain with wild type AOX1 promoter (GFP-Zeo D2), D6: single copy AOX1Δ6* clone; WT_E2: multicopy GFP-Zeo clone with wild type AOX1 promoter; D6* F10: multicopy AOX1Δ6* clone (X-33 d6F10).

FIG. 6 shows the result of a drop test of *P. pastoris* strains on MD and MDM agar plates with distinct ZEOCIN™ concentrations. Cells were grown on BMD(1%) medium to a OD595 of 1.5, diluted in steps of 10 to a final dilution rate of lo5 and transferred to the agar plates using a 48 pin replicator. Numbers on top of the picture denote the dilution factor which is the same for all plates. MD medium was prepared as described above. Methanol in MDM-Zeo plates was added to a final concentration of about 0.5%. ZEOCIN™ was added to final concentrations of 100, 200 and 500 µg/ml, respectively. X-33: *P. pastoris* X-33, A9: *P. pastoris* GFP-Zeo MutS A9, D2: *P. pastoris* GFP-Zeo D2, E2: *P. pastoris* GFP-Zeo E2.

EXAMPLES

Example 1

Figure 1:
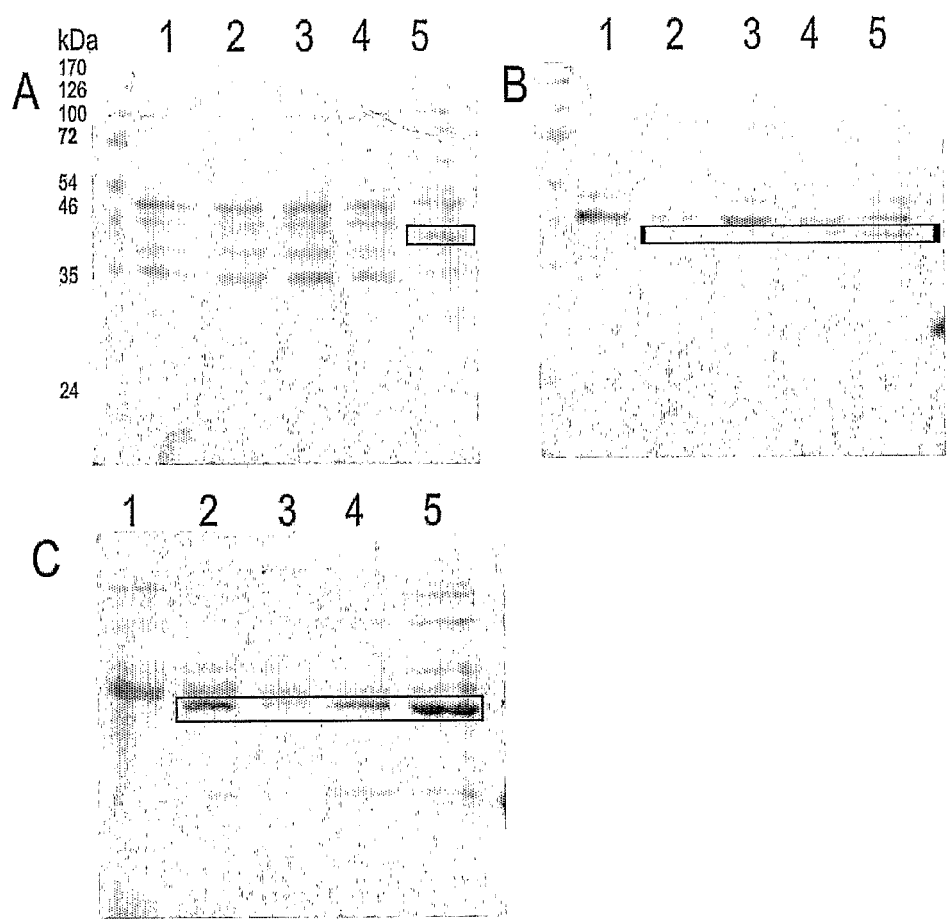

Material And Methods
a) DNA Preparation/Purification Kits
Several commercially available DNA preparation and purification kits have been used according to the supplied manuals (see Table 3).

TABLE 3

DNA Preparation and Purification Kits

| Kit | Producer |
| --- | --- |
| Easy-DNA ™ Kit | Invitrogen Corp., Carlsbad, CA, USA |
| QIAprep ® Spin Miniprep Kit | QIAGEN GmbH, Hilden, Germany |
| Wizard ® Plus SV Minipreps DNA Purification System | Promega GmbH, Mannheim, Germany |
| GenElute ™ High Performance (HP) Plasmid Midiprep Kit Germany | Sigma-Aldrich Handels GmbH, Vienna, Austria |
| QIAquick ® Gel Extraction Kit | QIAGEN GmbH, Hilden, Germany |
| Quantum Prep ™ Freeze N Squeeze DNA Gel Extraction Spin Columns | Bio-Rad Laboratories GmbH, Vienna, Austria |
| QIAquick ® PCR Purification Kit | QIAGEN GmbH, Hilden, Germany | b) TOPO® Cloning:
TOPO® cloning was performed according to the supplied manuals (for cloning into pCR®4Blunt-TOPO® and for cloning into pCR®-Blunt II-TOPO®). Always 4 µl of PCR product were used for cloning. 2 and 4 µl of every cloning reaction were transformed into One Shot® chemically competent *E. coli* TOP10F' cells (Invitrogen Corp., Carlsbad, Calif., USA) according to the above mentioned protocols.

c) *E. coli* transformation:
Transformation of ligation reactions and plasmids into *E. coli* was performed according to the SEM (simple and efficient method)-Protocol [16]. Chemically competent *E. coli* TOP10F' cells were used for transformation.

d) *Pichia pastoris* transformation:
Preparation of competent *Pichia pastoris* cells: A single colony of the desired *Pichia pastoris* host strain was used to inoculate 50 ml YPD (2% glucose) in a 300 ml baffled wide-necked Erlenmeyer flask. After an overnight incubation at 30° C., 60% humidity and 130 rpm (Pilot Shake® RC-2 TE) a certain volume of this pre-culture was used to inoculate 200 ml of YPD (2% glucose) in a 2 l baffled wide-necked Erlenmeyer flask to an optical density of about 0.1 at 595 nm (OD595). The culture was grown under the same conditions as the pre-culture to an optical density of 1.0 to 1.5. Cells were pelleted at 4° C. and 4000 rpm for 10 minutes and resuspended in 200 ml ice-cold sterile water. This procedure was repeated 3 time with re-suspension of the cells in 100 ml water, 10 ml 1 M sorbitol and 0.5 ml 1 M sorbitol, respectively.

10 µg of the desired plasmid were linearised with BglII and NotI (each 50 u) over night in a final volume of 300 µl. After restriction digestion the DNA was precipitated in EtOH and 0.3 M sodium acetate according to a standard protocol [16]. DNA was dissolved in 11 µl sterile ddH$_2$O and desalted using a MF-Millipore™ Membrane Filter (see Table 12) for about 1-2 h. If PCR-product was used for transformation about 4-5 µg DNA was processed as described above starting at EtOH precipitation.

For each transformation 80 µl of the prepared cells were mixed with 10 µg DNA as described above and incubated for 5 minutes on ice. The mixture was transferred to ice-cold electro-transformation cuvettes (Bio-Rad) and pulsed at 200Ω, 25 µF and 2.5 kV. 1 ml of icecold 1 M sorbitol was added immediately. The suspension was transferred to a sterile 12 ml PP-tube (Greiner, Frickenhausen, Germany, #184261) and incubated for 2 hours at 30° C. without shaking. After this regeneration phase aliquots were plated on selection plates. For selection of transformants with high expression under inducing condition, the cells were plated on MSM-Zeo plates containing minimal media with sorbitol (or any other non-repressing carbon source) methanol and ZEOCIN™. For the selection of clones showing high expression under derepressing conditions, the cells can be plated on minimal sorbitol zeo plates lacking methanol. The inclusion of glucose to methanol containing selection plates enables the detection of glucose non-repressed expression clones and their promoters.

e) Colony PCR:
A single colony of the desired *Pichia* strain was resuspended in 100 µl ddH$_2$O in a 100 µl microtube and heated for 5 to 10 minutes at 95° C. After centrifugation at 13,200 rpm for 1 minute 10 µl of supernatant were used as template for PCR reaction. 5 µl of this first PCR round were used as template for a second one. 5 µl of the second PCR round were used for a control gel. PCR reactions contained 10 µmol of each primer (AOX1_col and GFPrev), 200 µM of each dNTP and 2.5 units of Hot Star Taq® DNA polymerase (QIAGEN) or Taq DNA polymerase (Promega) under buffer conditions according to the supplied manuals in a final volume of 50 µl. For sequencing the second PCR product was purified using the QIAquick® PCR Purification Kit.

TABLE 4

Temperature programme for colony PCR

| Temperature | Taq | Hot Star Taq ® | Cycles |
| --- | --- | --- | --- |
| 95° C. | 5 min | 15 min | 1 |
| 95° C. | 30 sec | 30 sec | |
| 57° C. | 30 sec | 30 sec | |
| 72° C. | 1 min 30 sec | 1 min 30 sec | 30 |
| 72° C. | 10 min | 10 min | 1 | f) *Pichia pastoris* genomic DNA isolation:
The desired *P. pastoris* strain was grown overnight in 5 ml YPD in a sterile 12 ml PP-tube on a rotation barrel at 30° C. to a final OD595 of 5-10. 1.5 ml of the culture were used for DNA isolation using the Easy-DNA™ Kit according to the supplied protocol.

g) Protein assay:
Measurement of protein concentration in solution has long been used in biochemistry. One of their major applications is to normalise a wide variety of biochemical methods to the total protein amount as is done in the present case for the oxygen consumption rates. The most commonly used ways to determine protein concentrations are the Bradford, Lowry and BCA™ methods. These methods have definite limitations in respect of sensitivity, dynamic range and compatibility to specific reagents. Between these 3 assays, Bradford and Lowry are more reliable and reproducible than the BCA™. On the other hand Lowry and Bradford possess severe limitations when detergents and/or reducing agents are present which results in high blank values. Thus the BCA™ assay is the method of choice after a chemical lysis. Protein concentrations were determined using the BCA™-assay after chemical cell lysis with Y-Per® and BSA as standard according to the instruction manuals (Pierce Biotechnology Inc.) therefore only the main steps will be described briefly below. 200 µl of the cultures were centrifuged at 4000 rpm and 4° C. for 5 minutes. After discarding the supernatant the pellet was resuspended in 100 µl Y-Per® by pipetting up and down. The suspension was incubated in 1.5 ml microtubes in a Thermomixer at room temperature and 600 rpm for 20 minutes. After the cell debris was pelleted at 13,200 rpm and room temperature for 10 minutes the supernatant was transferred into a new microtube and stored at 4° C. for the BCA™ assay or SDS-PAGE. 25 µl sample were mixed in a microplate well with 200 µl BCA™ working reagent (reagent A: reagent B=50:1), agitated thoroughly for 30 seconds and covered tightly with plate sealers (Promega). After incubation for 30 minutes at 37° C. and cooling to room temperature the absorption was determined at 562 nm using a Spectramax Plus 384 plate reader. If necessary, samples were diluted with ddH$_2$O prior to the BCA assay.

h) SDS-PAGE:

Samples for SDS-PAGE were prepared by chemical cell lysis using Y-Per® as reagent as described in the section above. 10 µl of lysate were mixed with 10 µl 2×SSB (sigma sample buffer) and incubated at 95° C. for 5-10 min and 15 µl of this mixture were loaded on the protein gel. Electrophoresis was performed with 180 V for about 1 h and protein bands were detected using Coomassie™ blue staining.

TABLE 5

Gel preparation for SDS-PAGE

|  | Stacking gel (4%) | Resolving gel (12%) |
| --- | --- | --- |
| ddH2O | 3.05 ml | 3.35 ml |
| 30% Acrylamid/bis | 650 µl | 4 ml |
| 0.5M Tris-HCl pH 6.8 | 1.25 ml |  |
| 1.5M Tris-HCl pH 8.8 |  | 2.5 ml |

TABLE 5-continued

Gel preparation for SDS-PAGE

|  | Stacking gel (4%) | Resolving gel (12%) |
| --- | --- | --- |
| 10% (w/v) SDS | 50 µl | 100 µl |
| TEMED | 5 µl | 10 µl |
| 10% APS | 25 µl | 50 µl | i) Glucose assay:

Glucose concentrations were determined using the Glucose-UV Hexokinase method without deproteinisation (DIPRO med Handels GmbH, Weigelsdorf, Austria, Prod. no. D590522). 50 µl of *Pichia* cultures were transferred in a PCR microplate and centrifuged at 4000 rpm for 5 minutes. 10 µl of supernatant were added to 190 µl hexokinase reagent in an UV-Star microplate and incubated at room temperature for 15 minutes. After incubation absorption at 340 nm was determined using a Spectramax Plus 384 plate reader.

j) Drop Tests:

*P. pastoris* strains were grown in BMD (1%) to a final OD595 of 1.5 and diluted in steps of 10 to a final dilution rate of $10^5$. Transfer on agar plates was done with a 48 pin replicator. The plates were incubated at 30° C. until colonies appeared (usually 2 days on MD plates).

k) Sequence Alignments:

All sequence alignments were done using MultAlin at the INRA homepage (Institut National de la Recherche Agronomique, Paris, France) (prodes.toulouse.inra.fr/multalin/multalin.html) [17] or with ClustalW at the European Bioinformatics Institute (EBI, www.ebi.ac.ch/clustalw) [18]. For sequence comparison with MultAlin always the DNA sequence similarity matrix was used for comparison.

Genes of the methanol utilisation pathway and most peroxisomal genes are regulated in a similar way in respect to glucose repression, derepression at carbon starvation and induction through methanol. A similar transcriptional regulation with a defined set of transcription factors (repressors as well as inducers) should be responsible for this regulation pattern. Transcription factor binding sites within these promoter regions should show some conserved regions. Multiple sequence alignment between promoter regions of coregulated genes should reveal the conserved binding sites of the transcription factors involved in regulation of the accordant genes. Several genes of the methylotrophic yeasts *P. pastoris*, *H. polymorpha* and *C. boidinii* were reported to be coregulated and their promoter sequences were isolated (Table 6).

TABLE 6

Coregulated genes of the methanol utilisation pathway or peroxisomal genes from the methylotrophic yeasts *P. pastoris*, *H. polymorpha* and *C. boidinii*.

| Yeast | Gene | Enzyme | Genbank Acc. No. | Literature |
| --- | --- | --- | --- | --- |
| *P. pastoris* | AOX1 | alcohol oxidase |  | www.invitrogen.com |
|  | AOX2 | alcohol oxidase | X79871 |  |
|  | ZZA1 | alcohol oxidase | S62281 |  |
|  | FLD1 | formaldehyde dehydrogenase | AF066054 |  |
| *H. polymorpha* | MOX | methanol oxidase | A11156 |  |
|  | DAS | dihydroxyacetone synthase | A11168 |  |
|  | CAT | catalase | X56501 |  |
| *C. boidinii* | AOD1 | alcohol oxidase | M81702 |  |
|  | FLD1 | formaldehyde dehydrogenase | AB085186 |  |
|  | FDH1 | formate dehydrogenase | AB035095 |  |
|  | DAS1 | dihydroxyacetone synthase | AB035094 |  |

TABLE 6-continued

Coregulated genes of the methanol utilisation pathway or peroxisomal genes from the methylotrophic yeasts *P. pastoris, H. polymorpha* and *C. boidinii*.

| Yeast | Gene | Enzyme | Genbank Acc. No. | Literature |
|---|---|---|---|---|
| | PMP20 | peroxisomal membrane protein | AB035096 | |
| | PMP47 | peroxisomal membrane protein | AB035097 | |
| | CTA1 | catalase | AB064338 | | l) Transcription Factor Analysis:

Transcription factor analysis was done with MatInspector Release professional 6.1 Jan. 2003 within the Genomatix-Suite 1.6.1 at Genomatix Software GmbH Servers [15]. PAOX1 sequence from pPICZ B was used to search for transcription factor binding sites using the Matrix Family Library Version 3.1.1 Apr. 2003 group ALL fungi.lib (www.genomatix.de).

m) Primers:

TABLE 7

List of primers used for the described examples (synthesised by MWG Biotech AG, Ebersberg, Germany)

| SEQ ID No. | Name | Sequence | Tm [° C.] |
|---|---|---|---|
| 2 | P(AOX1)forw | AAGGTACCAGATCTAACATCCAAAGACGAAAG | 70 |
| 3 | P(AOX1)rev | CTAGCCATGGTTGAATTCTTTCGAATAATTAGT-TGTTTTTTG | 67 |
| 4 | GFPZeo forw | GAAAGAATTCAACCATGGCTAGCAAAGGAG | 70 |
| 5 | GFPZeo rev | GATGATGGTCTAGAACGTGTCAGTCCTGCTCCTC | 70 |
| 6 | AOX1TT forw | GACACGTTCTAGACCATCATCATCATCATCATTG | 67 |
| 7 | AOX1TT rev | ATAGCGGCCGCACAAACGAAGGTCTC | 72 |
| 8 | AOX1Δ1forw | CAACACCCACTTTAGGCTACTAACACCAT-GACTTTATTAG | 71 |
| 9 | AOX1Δ1rev | GTTAGTAGCCTAAAGTGGGTGTTGAGGAGAAGAG | 70 |
| 10 | AOX1Δ2forw | GTTCATGTTTGTAGATGAGGGCTTTCTGAGTG | 67 |
| 11 | AOX1Δ2rev | GCCCTCATCTACAAACATGAACCTCGCCAG | 71 |
| 12 | AOX1Δ3forw | GAGGGCTTTCCCAAATGGCCCAAAACTG | 70 |
| 13 | AOX1Δ3rev | CCATTTGGGAAAGCCCTCATCTGGAGTG | 70 |
| 14 | AOX1Δ4forw | CGGCCAGTTGTTGGTATTGATTGACGAATGC | 69 |
| 15 | AOX1Δ4rev | CAATACCAACAACTGGCCGTTAGCATTTC | 71 |
| 16 | AOX1Δ5forw | GCTTCTGAACCTTGTCTCCACATTGTATGCTTC | 68 |
| 17 | AOX1Δ5rev | GTGGAGACAAGGTTCAGAAGCGATAGAGAGAC | 68 |
| 18 | AOX1Δ6forw | GTCTCCACACTGCTGATAGCCTAACGTTC | 66 |
| 19 | AOX1Δ6rev | GGCTATCAGCAGTGTGGAGACAATGCATAATCATC | 71 |
| 20 | AOX1Δ7forw | GGAATACTGCTCTAACCCCTACTTGACAGC | 65 |
| 21 | AOX1Δ7rev | GTAGGGGTTAGAGCAGTATTCCCACCAGAATC | 67 |
| 22 | AOX1Δ8forw | CTTGACAGCAAGCTGCCCTGTCTTAAACC | 66 |
| 23 | AOX1Δ8rev | GGGCAGCTTGCTGTCAAGTAGGGGTTAG | 68 |
| 24 | AOX1Δ9forw | CTGTCTTAAACCTTACTGGTTCCAATTGACAAGC | 68 |

TABLE 7-continued

List of primers used for the described examples
(synthesised by MWG Biotech AG, Ebersberg, Germany)

| SEQ ID No. | Name | Sequence | Tm [° C.] |
|---|---|---|---|
| 25 | AOX1Δ9rev | GGAACCAGTAAGGTTTAAGACAGGGCAGC | 69 |
| 26 | 423forw | GATACACTAGCAGCAGACCGTTGCAAACGCAG-GACCTCCACTCC | 87* |
| 27 | 1372forw | GTGAAGGTGATGCTACATACGGAAAGCTTACCCT-TAAATTTATTTGC | 81* |
| 28 | 2325forw | CGTGGCCGAGGAGCAGGACTGACACGTTCTAGACCAT-CATC | 86* |
| 29 | AOX1_col | TCCAAAGACGAAAGGTTGAATG | 72 |
| 30 | GFPrev | CCGTATGTAGCATCACCTTCACC | 74 |

*Tm calculated using Equation 2 (QuikChange ® multi site-directed mutagenesis kit)

Example 1.1

Cloning of the Reporter Construct

GFP-Zeo was used as a reporter for gene expression driven by AOX1 promoter variants. Sequences surrounding the ATG start codon were constructed to fulfil minimal requirements of Kozak consensus sequences for highly expressed genes in yeast. To change the promoter regions in front of the GFP-Zeo gene an EcoRI restriction site was inserted (Table 8) by overlap extension PCR.

TABLE 8

Comparison of translation initiation site and surrounding sequences between the AOX1 sequence used in this example (derived from pPICZ) and the AOX1 sequence of P. pastoris strain NRRL Y-11430 (Genbank AN: U96967, [2]).

```
                       -3   +1 +4
P(AOX1)-GFP   AAAACAACTA ATTATTgaAa gaattcAACc ATGGCTAgCa AOX1 (U96967) AAAACAACTA ATTATTcgA- ------AACg ATGGCTAtCc
```

EcoRI restriction site is underlined and minimal Kozak requirements at positions -3 and +4 are labelled in bold letters.

PCR-based production of reporter system components P(AOX1) was amplified using 10 ng of the vector pPICZ-B ARS1 as template. The reaction also contained 10 pmol of each primer (P(AOX1) forw and P(AOX1) rev, respectively), 200 μM of each dNTP and 2.5 U Synergy™ polymerase in appropriate buffer conditions in a final volume of 50 μl.

AOX1 TT was amplified similarly to the AOX1 promoter. AOX1TTforw and AOX1TTrev were used as primer in this reaction. Both PCR reactions were performed in a thermocycler for 30 cycles (95° C., 1 min; 55° C., 30 s; 68° C., 2 min 30 s) with an initial denaturation step of 5 min at 95° C. and a final extension step of 10 min at 68° C. 2 μl of first PCR round were used for amplification in a second round under the same conditions above. The only difference was an increase in extension temperature to 72° C.

GFP-Zeo [19] was amplified using 25 ng of the vector pTracer™-CMV2 as template. The reaction also contained 10 pmol of each primer (GFP-Zeo forw and GFP-Zeo rev, respectively), 200 μM of each dNTP and 2.5 U Synergy™ polymerase in appropriate buffer conditions in a final volume of 50 μl. PCR was performed in a thermocycler (see Table 8) for 30 cycles (95° C., 1 min; 55° C., 30 s; 72° C., 2 min 30 s) with an initial denaturation step of 5 min at 95° C. and a final extension step of 10 min at 72° C.

All PCR products were purified by agarose gel electrophoresis prior to overlap extension PCR. The reaction contained 10 ng P(AOX1), 5 ng AOX1 TT and 50 ng GFP-Zeo prepared as described above as templates, 200 μM of each dNTP and 2.5 U Synergy™ polymerase in appropriate buffer conditions in a final volume of 50 μl. PCR was performed in a thermocycler (see Table 8) for 30 cycles (95° C., 1 min; 53° C., 50 s; 68° C., 3 min 30 s) with an initial denaturation step of 5 min at 95° C. and a final extension step of 10 min at 68° C. After 10 cycles 10 μl of a mixture containing 10 pmol of the outer primers P(AOX1) forw and AOX1TTrev, again 200 μM of each dNTP and 2.5 U Synergy™ polymerase in appropriate buffer conditions were added. The PCR was continued as programmed after this addition. The obtained PCR product with the desired size of about 2.4 kb was purified on an agarose gel. The purified product was cloned into pCR®4Blunt-TOPO® vector and sequenced. Sequencing revealed 4 mutations and 1 deletion within the reporter construct.

The base pair deletion site was found at position −15 of the original promoter sequence. Since this position was within the multiple cloning site of all pPICZ vectors (A, B and C; inside the SfuI restriction site) the deletion should not influence the promoter activity and therefore was not corrected. The first mutation (T-->C) was found in the promoter region at position −828. The other 3 mutations were found within the GFP-Zeo coding sequence at positions +122, +507 and +1075, respectively.

The G-->A conversion at position +122 changes the GGA codon of Gly to a GAA codon which results in a G41A amino acid change. T-->C conversion at +507 is a silent mutation changing only a codon of R169. The last mutation (T-->C) at position +1075 changes the TGA stop codon to the Arginine codon CGA. The mutations −828, +122 and +1075 were repaired with the QuikChange® multi site-directed mutagenesis kit after constructing the pAOX vector. The silent mutation at position +507 and the mutation in the polylinker were not changed since it did not introduce a rare codon.

pAOX was constructed by excising the $P_{AOx1}$-GFP-Zeo-AOX1TT fragment from pCR®4Blunt-TOPO® vector with KpnI and NotI and inserting it into the pBlueScript® SK- vector between the KpnI and NotI site.

The mutations found in the AOX1 promoter and the GFP-Zeo sequence were corrected using the QuikChange® multi site-directed mutagenesis kit (Stratagene, Amsterdam, The Netherlands). The PCR reaction was performed according to the supplied manual containing 100 ng pAOX, 100 ng of mutagenic primers (423forw, 1372forw and 2325forw, respectively) and 1 µl QuikChange® multi enzyme blend in appropriate buffer conditions in a final volume of 25 µl in a thermocycler for 30 cycles (95° C., 1 min; 55° C., 1 min; 65° C., 10 min 30 s) with an initial denaturation step of 1 min at 95° C. DpnI digestion and chemical transformation into *E. coli* XL10-GOLD® (Invitrogen Corp.) cells was done according to the supplied manual. Correction of all 3 mutations was verified by sequencing.

Example 1.2

Construction of AOX1 Promoter Deletions

Left arms of the AOX1 promoter were synthesised using P(AOX1) forw as forward primer and AOX n rev (n=1 . . . 9) as reverse primers. Right arms were synthesised with 10 pmol of AOX n forw (n=1 . . . 9) as forward primers and P(AOX1) rev as reverse primer. All arms were synthesised using 12 ng of the vector pAOX as template and 10 µg of each primer. The reaction also contained 10 pmol of each primer, 200 µM of each dNTP and 0.6 U Pwo DNA polymerase in appropriate buffer conditions in a final volume of 50 µl. PCR was performed in a thermocycler for 30 cycles (95° C., 1 min; 55° C., 1 min; 68° C., 1 min 30 s) with an initial denaturation step of 5 min at 95° C. and a final extension step of 10 min at 68° C. All arms were agarose gel purified prior to the use as template for overlap extension PCR.

TABLE 9

Overlap primer pairs and arm length for promoter deletions

| | left arm | | right arm | |
|---|---|---|---|---|
| Construct | internal primer | arm length [bp] | internal primer | arm length [bp] |
| PAOX1Δ1 | AOXΔ1 rev | 184 | AOXΔ1 forw | 738 |
| PAOX1Δ2 | AOXΔ2 rev | 315 | AOXΔ2 forw | 624 |
| PAOX1Δ3 | AOXΔ3 rev | 374 | AOXΔ3 forw | 578 |
| PAOX1Δ4 | AOXΔ4 rev | 519 | AOXΔ4 forw | 421 |
| PAOX1Δ5 | AOXΔ5 rev | 636 | AOXΔ5 forw | 290 |
| PAOX1Δ6 | AOXΔ6 rev | 708 | AOXΔ6 forw | 247 |

TABLE 9-continued

Overlap primer pairs and arm length for promoter deletions

| | left arm | | right arm | |
|---|---|---|---|---|
| Construct | internal primer | arm length [bp] | internal primer | arm length [bp] |
| PAOX1Δ7 | AOXΔ7 rev | 742 | AOXΔ7 forw | 209 |
| PAOX1Δ8 | AOXΔ8 rev | 794 | AOXΔ8 forw | 171 |
| PAOX1Δ9 | AOXΔ9 rev | 833 | AOXΔ9 forw | 115 |

The reaction contained 10 ng of each arm prepared as described above as templates, 200 µM of each dNTP and 0.6 U Pwo DNA polymerase in appropriate buffer conditions in a final volume of 50 µl. PCR was performed in a thermocycler for 30 cycles (95° C., 45 s; 60° C., 45 s; 68° C., 2 min) with an initial denaturation step of 5 min at 95° C. and a final extension step of 10 min at 68° C. After 10 cycles 20 µl of a mixture containing 10 pmol of the outer primers P(AOX1) forw and P(AOX1) rev, again 200 µM of each dNTP and 0.6 U Pwo DNA polymerase in appropriate buffer conditions were added. The PCR was continued as programmed after addition of the mixture.

The obtained PCR products with the desired size of about 898-947 bp were purified on an agarose gel and cloned into pCR®4Blunt-TOPO® (Δ2, Δ4, Δ5, Δ7 and Δ8) or into pCR®-Blunt II-TOPO® vector (Δ1, Δ3, Δ6 and Δ9) and sequenced. pAOXΔ vectors were constructed by excising the $P_{AOX1}\Delta$ fragments from TOPO® vectors with BglII and EcoRI and inserting them into the pAOX vector between BglII and EcoRI site instead of the wild type AOX1 promoter. The resulting vectors were verified by sequencing.

Example 1.3

*Pichia Pastoris* Transformation and Analysis of Transformants

*Pichia pastoris* transformation was done as described earlier. Selection for Integration of PAOX1 (or $P_{AOX}1\Delta$)-GFP-Zeo-AOX1TT was done by spreading the transformed and regenerated *Pichia* cells in aliquots on MSM-Zeo agar plates.

*Pichia pastoris* strains were grown in deep well plates containing 300 µl BMD (1%) per well at 28° C., 320 rpm and 80% humidity for 60 hours at room temperature. After this time, 50 µl were taken for determination of the GFP-fluorescence. Induction was performed by adding 250 µl BMM2/well followed by a further incubation of 72 h. Methanol was refilled by adding 50 µl BMM10 after 10, 24 and 48 hours. Once more GFP fluorescence was measured after 72 h of methanol induction.

Analysis of reporter enzyme expression Expression of GFP-Zeo in *Pichia pastoris* was analysed by fluorescence detection of GFP in the Spectramax Gemini XS plate reader with excitation at 395 nm and emission at 507 nm. 50 µl of *P. pastoris* cultures cultivated in deep well plates as described above were diluted 1+3 with ddH$_2$O in FIA microtiter plates. Due to the limited sample amount only single measurements were performed. All means ± standard deviations given are calculated from at least 3 different cultures (wells).

If the integration cassette is integrated in the AOX1 locus without replacing the AOX1 gene, the recombinant *Pichia* strain is able to grow on methanol with a wild type rate, while replacement of the AOX1 gene by double crossover results in a much slower growth rate on methanol. These two growth phenotypes are called methanol utilisation plus (Mut$^+$) and methanol utilisation slow (Mut$^s$), respectively. For analysis of the methanol utilisation phenotype, *Pichia pastoris* microscale cultures were transferred on MM and MD agar plates using a 96-pin replicator and incubated at 30° C. for 2 days. After 2 days colonies appear on both plates if the *Pichia* strain possesses Mut$^+$ phenotype while with Mut$^s$ phenotypic strains only on MD plates colonies arise.

All *Pichia* strains which are derived from transformations of pAOX or one of the pAOXΔ plasmids were analysed by colony PCR and deletion constructs also by sequencing to assure the promoter sequence in front of the reporter gene (GFP-Zeo).

Example 1.4

Directed Evolution of the AOX1 Promoter

While PCR mutagenesis on coding regions of genes is well developed and established nothing is known about mutagenesis on promoter regions. Due to the lack of knowledge several mutagenesis conditions were performed: To minimise bias in mutational spectrum, two different polymerases were used, a Taq DNA polymerase and the Mutazyme® DNA polymerase (Stratagene Inc.). Due to the fact that knowledge on mutation frequency for evolution of promoter sequences is completely lacking, several mutation frequencies (theoretically 1 to ~14/kb) were tested.

Mutagenesis using Hot Star Taq® DNA polymerase: Mutagenic PCR was performed on the promoter sequence in a 100 μl reaction volume according to [20]. The reaction contained 12 ng pAOX, 40 pmol of each primer, (P(AOX1) forw and P(AOX1) rev), dNTPs (200 μM dGTP, 200 μM dATP, 1 mM dTTP, 1 mM dCTP) and 5 U Hot Star Taq® DNA polymerase in appropriate buffer conditions. MgCl$_2$ concentration was increased to 7 mM (usually 3 mM) to alter the error rate of the polymerase. PCR was performed in a thermocycler for 30 cycles (95° C., 45 s; 55° C., 45 s; 72° C., 1 min 30 s) with an initial denaturation step of 15 min at 95° C. and a final extension step of 10 min at 72° C.

The GeneMorph® random mutagenesis kit was performed on the promoter sequence in a final volume of 50 μl according to the supplied manual. Different amounts of the vector pAOX as template were used (see Table 10). 12.5 pmol of each primer, P(AOX1) forw and P(AOX1) rev were used. PCR reaction was performed in a thermocycler for 30 cycles (95° C., 30 s; 55° C., 30 s; 68° C., 1 min 30 s) with an initial denaturation step of 1 min at 95° C. and a final extension step of 10 min at 68° C.

TABLE 10

Amount of template used in the GeneMorph ® PCR reaction

| No. | mutation frequency | amount pAOX | expected mutations/kb |
|---|---|---|---|
| 1 | low-medium | 12 ng | ~3 or lower |
| 2 | medium | 1.2 ng | 3-7 |
| 3 | medium-high | 120 pg | ~7 or higher |

A first round of mutagenesis with conditions described above (Taq, 3× GeneMorph®) was performed. To get higher mutation frequency the GeneMorph® reaction #3 was used as template for a second PCR round. Taq and GeneMorph® #2 and #3 conditions were used.

Prior to the transformation into *Pichia pastoris* X-33 GFP-Zeo Mut$^S$ A9 cells, all PCR reactions were precipitated and desalted bas described earlier. The standard transformation and regeneration procedure was used. Selection for promoters induced in glucose medium was done by spreading 150 μl aliquots of transformed cell suspension on MD agar plates containing 100-500 μg/ml ZEOCIN™ and incubation on 30° C. for 2 days.

Example 1.5

Results and Discussion

I) Characterisation of the Reporter System

To date, a large variety of GFP variants are in use in molecular biology. Although differing only in a few point mutations, their characteristics differ enormously. Apart from improved folding properties their fluorescence spectra as well as their quantum yields and therefore intensities differ a lot. Green fluorescent proteins can be divided into two main groups, depending on their excitation maximum: wild type GFP variants with an excitation maximum at 395 nm and a minor maximum at 470 nm, and red-shifted GFP variants with an excitation maximum at 480-490 nm. According to its amino acid sequence, cycle-3-GFP belongs to the group of wild type GFP variant with an excitation maximum at 395 nm.

To control the spectral properties when expressed in *Pichia pastoris* fluorescence spectra were determined. The overall excitation maximum of the cycle-3-GFP in GFP-Zeo is 395 nm, while the second maximum at 478 nm is evanescent. The emission spectrum reveals an emission maximum of 510 nm. Of the two excitation wavelengths suggested by the manual 395 nm is preferred and was used for all further measurements.

Self-absorption is a very frequent phenomenon in fluorescence spectroscopy. At high concentrations of the fluorophor, photons emitted in a region overlapping the absorption (excitation) spectrum can be absorbed (radiative energy transfer). Lower fluorescence intensity will be observed if self-absorption (emission inner filter effect) will occur. This leads to an underestimation of promoter activities. With no inner filter effect fluorescence intensity increases in a linear way as the fluorophor increases. Thus increasing volumes of GFP-Zeo expressing *Pichia pastoris* cells were tested for their fluorescence activity.

Up to 3000 RFU no emission inner filter effect was detectable on the cell level. Self-absorption within the cells, caused by the accumulation of GFP, could not be evaluated. A linear increase in fluorescence over the whole 72 hours of induction phase was detected. For that reason an inner filter effect within the cells seems to be not likely. Thus the accumulation of GFP-Zeo within the nucleus is no problem for its quantitation. No inner filter effect occurs within the range of single copy promoter activities determined in this study. Due to the lack of self-absorption underestimation of promoter activities is not likely to occur. The inner filter effect observed by others is most probably caused by the usage of a different GFP variant with a much smaller Stokes shift and therefore overlapping excitation and emission spectra. One has to be careful when comparing results of GFP expression experiments. The usage of several GFP variants with distinct spectral properties, but also with optimised codon usages and therefore quite different expression levels in different expression hosts complicates the comparability of results of different labs.

II) AOX1 Promoter Activity in Microscale

Small scale cultivation of microbial cells (e.g. yeast, bacteria) is usually done in shake flask cultures. Inoculation and cultivation of large microbial libraries in shake flasks are labour and time intensive resulting in high costs. In recent years microscale cultivation systems using deep-well microtiter plates were developed as an alternative. Due to the parallel handling of e.g. 96 or 384 strains/cultures and the less material needed, microtiter systems are superior to shake flasks in terms of labour, time and therefore cost intensities. Due to several reasons, the major drawbacks of microtiter systems, small sample volume and low aeration efficiency, are less relevant: (1) technical advances in analytical systems lead to lower detection limits of a large number of compounds resulting in very low sample volumes needed; (2) methods and devices for growth in deep-well microtiter plates were also improved. It has been shown in a few studies that aeration rates and therefore growth conditions in microtiter plates are similar to shake flasks. It has also been demonstrated that real-time studies on the GAL1 promoter in *S. cerevisiae* using cycle-3-GFP as reporter protein are consistent with shake flask studies.

AOX1 promoter driven GFP-Zeo expression was studied in deep-well microtiter plates as described above. After cell growth on glucose an induction phase with methanol as carbon and energy source follows. Induction of the AOX1 promoter with methanol in *Pichia pastoris* cells possessing the PAOX1-GFP-Zeo-AOX1TT expression cassette led to a fast increase in GFP fluorescence. Until 72 h GFP fluorescence increased in a linear way. Expression of GFP-Zeo would continue if methanol is added. If not, methanol depletes through evaporation and consumption within 24 h and GFP-Zeo expression decreases to a derepressed level.

The increase in GFP-Zeo fluorescence was also in accordance with GFP-Zeo protein as was shown by SDS-PAGE. Upon methanol induction a protein band of about 42 kDa appeared which became more intensive as fluorescence increased. The strong band at 42 kDa was found in all GFP-Zeo clones while in the negative control (X-33 wild type) no band appeared. Also in the sample of X-33 d6*F10 after 72 hours of methanol induction a strong band was found (FIG. 1C, Lane 5). Although not normalized a clear correlation between the intensities of the 42 kDa bands and the appropriate fluorescence levels is assessable.

III) Transcription Factor Binding Sites

Figure 2:
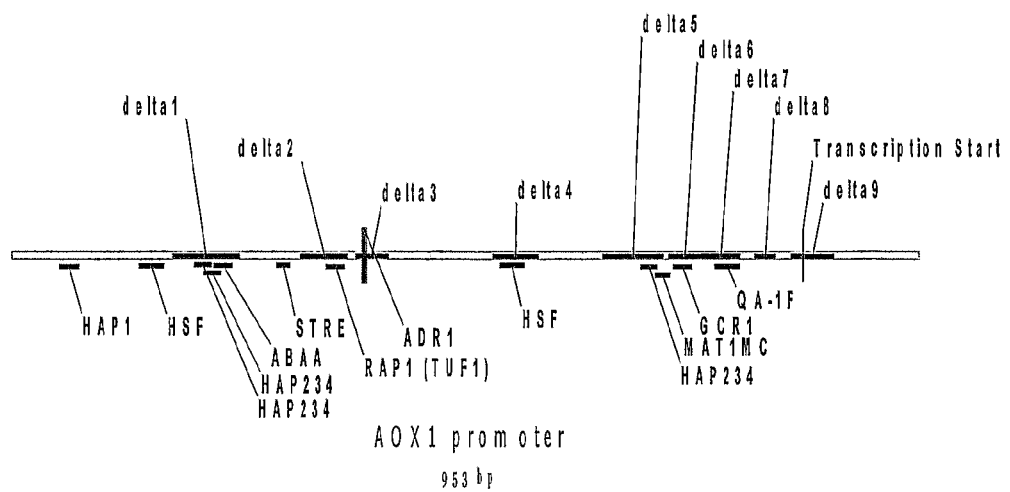

As described earlier, consensus sequences for binding sites of several transcription factors are known. Sequence analysis of the AOX1 promoter sequence revealed several putative transcription factor binding sites, with a few hits of special interest. Among heat shock factor and stress response element motif, binding sites of a few transcription factors generally known to be involved in glucose regulation were found. The most interesting binding sites were summarized in Table 11 and FIG. 2.

TABLE 11

Transcription factor (TF) binding sites found within the AOX1 promoter sequence. Base pairs in capital letters denote the core sequence (the 4 highest conserved, consecutive residues of the matrix), underlined base pairs show a high information content (Ci > 60 of a maximum of 100).

| TF Matrix | Position (5)* | Deletion variant | Core similarity | Matrix similarity | Sequence | Seq ID No. |
|---|---|---|---|---|---|---|
| HAP1.01 | 52-66 (-902 to -888) | | 1.000 | 0.802 | ctgtg-gat gtCGGAt | 31 |
| HSF.01 | 135 to 155 (-819 to -799) | | 1.000 | 0.784 | AGAAgag-gagtg-gag-gtcctg | 32 |
| HAP234.01 | 193 to 205 (-761 to -749) | Δ1 | 1.000 | 0.895 | caagc-CCAAtaac | 33 |
| HAP234.01 | 203 to 215 (-751 to -739) | Δ1 | 1.000 | 0.923 | gagctCCA Atcaa | 34 |
| ABAA.01 | 213 to 227 (-741 to -727) | Δ1 | 1.000 | 0.949 | ctcgct-CATTccaat | 35 |
| STRE.01 | 279 to 287 (-675 to -667) | | 1.000 | 1.000 | ccAGGGGggg | 36 |
| RAP1.01 | 332 to 346 (-622 to -608) | Δ2 | 1.000 | 0.845 | tacAC-CCgaa-catca | 37 |
| ADR1.01 | 371 to 377 (-583 to -577) | Δ3 | 1.000 | 1.000 | tGGGGtc | 38 |
| HSF.03 | 516 to 536 (-438 to -418) | Δ4 | 1.000 | 0.862 | AGAAactt ccaaaagt cggc | 39 |
| HAP234.01 | 665 to 677 (-289 to -277) | Δ5 | 1.000 | 0.883 | at-catCCAAa aag | 40 |
| MAT1MC.01 | 680 to 690 (-274 to -264) | | 1.000 | 0.901 | tgcaT-TGTctc | 41 |

TABLE 11-continued

Transcription factor (TF) binding sites found within the AOX1 promoter sequence. Base pairs in capital letters denote the core sequence (the 4 highest conserved, consecutive residues of the matrix), underlined base pairs show a high information content (Ci > 60 of a maximum of 100).

| TF Matrix | Position (5)* | Deletion variant | Core similarity | Matrix similarity | Sequence | Seq ID No. |
|---|---|---|---|---|---|---|
| GCR1.02 | 699 to 713 (−255 to −241) | Δ6 | 1.000 | 0.872 | at- gCTTCcaa gattc | 42 |
| QA-1F.01 | 743 to 763 (−211 to −191) | Δ7 | 0.785 | 0.775 | acagt- taaatttT GATcatga | 43 |

*The given position is marked in respect to the translation start point (ATG) of the GFP-Zeo gene; core sequences of putative transcription factor binding sites are shown in capital letters
c denotes homology to the complementary strand IV) Regulatory Sequences in Methanol Regulated Genes Several sequences are described in literature to be involved in regulation of methanol inducible genes. Based on deletion analysis of the *P. pastoris* AOX2 promoter three regulatory regions were described, two negative acting regions (URS1 and URS2, upstream repression sequences) and a positive acting domain (UAS, upstream activation sequence) [3]. For the *H. polymorpha* MOX promoter two upstream activating sequences (UAS1 and UAS2) and one repressor binding site (URS1) were also described [8].

V) Deletion Constructs of AOX1 Promoter

Based on the transcription factor analysis and the multiple sequence alignment 9 promoter regions were chosen for deletion by overlap extension PCR as described earlier. The AOX1 promoter deletion constructs were cloned into the pAOX vector to replace the "wild type AOX1" promoter 5 to the reporter gene GFP-Zeo. The plasmids were linearised and integrated into the *Pichia pastoris* genome.

TABLE 12

Sequences deleted in the AOX1 promoter constructs

| Construct | Position* 5′ end | Position* 3′ end | Sequence | Seq ID No. |
|---|---|---|---|---|
| PAOX1Δ1 | 170 (−784) | 235 (−719) | tttgccatcgaaaaaccagcccagt- tattgggcttgattggagctcgct- cattccaattccttcta | 44 |
| PAOX1Δ2 | 304 (−650) | 350 (−604) | ttatttccgaatgcaacaagctccgc- attacacccgaacatcactcc | 45 |
| PAOX1Δ3 | 364 (−590) | 393 (−561) | ctgagtgtggggtcaaatagtttcat- gttc | 46 |
| PAOX1Δ4 | 509 (−445) | 551 (−403) | gtcaaaaagaaacttccaaaagtcg- gcataccgtttgtcttgt | 47 |
| PAOX1Δ5 | 625 (−329) | 683 (−271) | ccggtgcacctgtgc- cgaaacgcaaatggggaaacac ccgcttttggatgattatgca | 48 |
| PAOX1Δ6 | 694 (−260) | 723 (−231) | attgtatgcttccaagattctggtgg- gaat | 49 |
| PAOX1Δ7 | 729 (−225) | 763 (−191) | tgatagcctaacgttcatgat- caaaatttaactgt | 50 |

TABLE 12-continued

Sequences deleted in the AOX1 promoter constructs

| | Position* | | | Seq ID |
|---|---|---|---|---|
| Construct | 5' end | 3' end | Sequence | No. |
| PAOX1Δ8 | 784 (−170) | 800 (−154) | aatatataaacagaagg | 51 |
| PAOX1Δ9 | 823 (−131) | 861 (−93) | ttttttatcatcattattagct-tactttcataattgcg | 52 |

*The given positions are marked in respect to Seq ID No. 1

Figure 3:
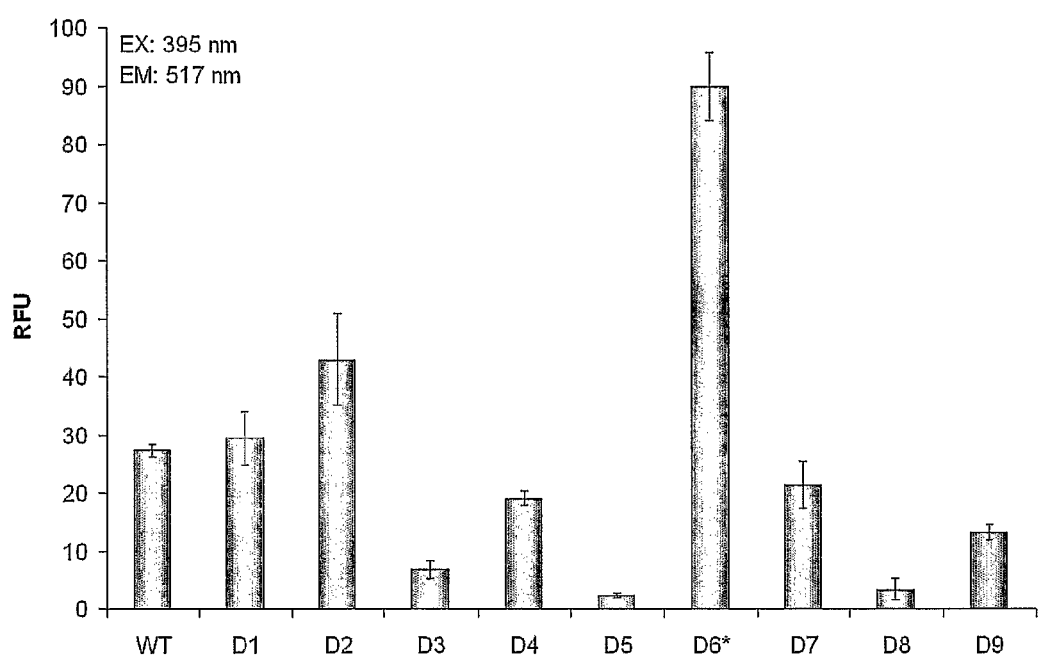

Integrants were analysed for GFP-Zeo expression and for integration of the correct promoter sequence in front of the GFP-Zeo gene as described above. Single copy integrants were analysed in further detail for their GFP-Zeo expression levels in different carbon sources in microscale. In all constructs (deletion and wild type) no GFP fluorescence could be detected as long as glucose or glycerol was present in the medium (with and without methanol). Upon carbon starvation, representing derepressing conditions, a slight increase in GFP fluorescence was detected. Compared to wild type some promoter variants showed remarkable differences (FIG. 3). A significant lower promoter activity was found in 6 constructs (Δ3, Δ4, Δ5, Δ7, Δ8 and Δ9, see FIG. 3) under derepressing conditions. Δ1 possessed wild type activity while the constructs Δ2 and Δ6* resulted in significantly higher GFP-Zeo expression. Expression level of the latter one was remarkably higher than the wild type level.

Figure 4:
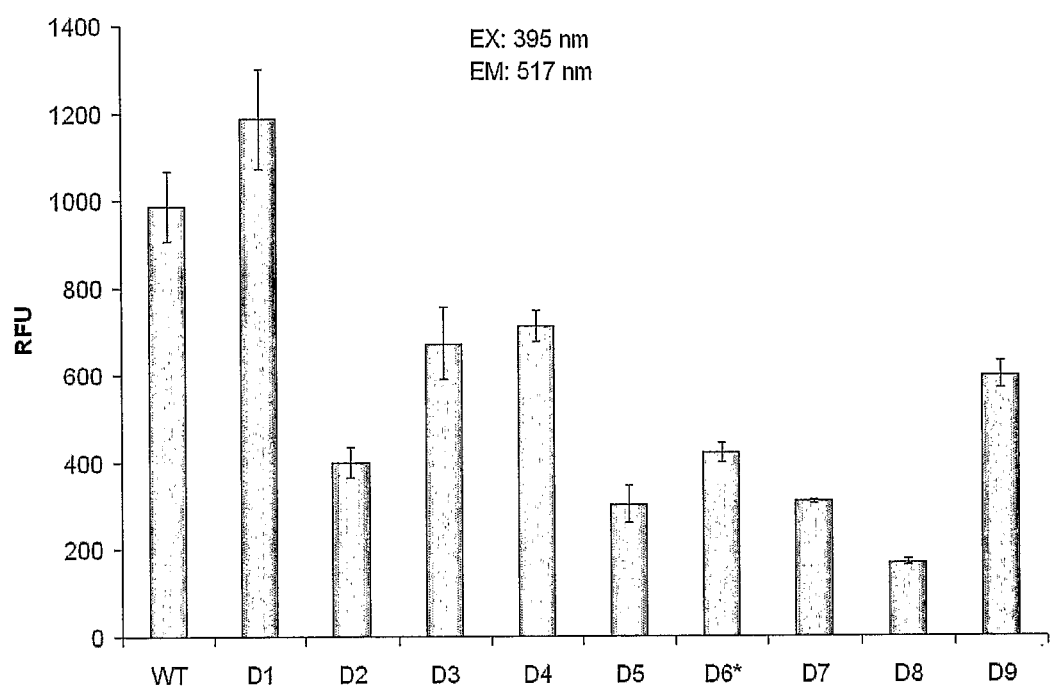

Upon methanol induction all variants showed significant decreased promoter activity with only one exception: Δ1 which resulted in around 20% higher activity compared to wild type. The decrease in activity of all other variants is quite significant as can be seen in FIG. 4.

Promoter activity of all variants and wild type constructs normalized on methanol-induced wild type activity is summarized in Table 13.

TABLE 13

Fluorescence intensity of AOX1 promoter variants in microscale. The data represents the mean SD of 4 independent measurements. Fluorescence intensity after 72 h methanol induction of WT promoter (100%) is 987 ± 81. No fluorescence was detectable as long as glucose is present in the medium.

| | relative fluorescence intensity [%] | |
|---|---|---|
| Construct | Derepression | Methanol |
| PAOX1 | 2.8 ± 0.1 | 100 |
| PAOX1Δ1 | 3.0 ± 0.5 | 120 ± 12 |
| PAOX1Δ2 | 4.4 ± 0.8 | 40 ± 3 |
| PAOX1Δ3 | 0.7 ± 0.2 | 68 ± 8 |
| PAOX1Δ4 | 1.9 ± 0.1 | 72 ± 4 |
| PAOX1Δ5 | 0.23 ± 0.04 | 30 ± 4 |
| PAOX1Δ6* | 9.1 ± 0.6 | 42 ± 2 |
| PAOX1Δ7 | 2.2 ± 0.4 | 31.3 ± 0.5 |
| PAOX1Δ8 | 0.3 ± 0.2 | 17.1 ± 0.7 |
| PAOX1Δ9 | 1.3 ± 0.1 | 61 ± 3 |

Deletion of the TATA box in construct Δ8 resulted in a massive destruction of the promoter with a severe decrease of activity at derepressing and inducing conditions of about 90% and 80%, respectively. By elimination of the experimentally determined (Ellis, S. B., et al., Mol. Cell. Biol. (1985) 5:1111-1121) transcription initiation start (Δ9) no such strong effect on the expression level was observed. It is one of the best deletion constructs after methanol induction. As expected, the TATA box has a severe impact on the transcription level. In contrast the transcription initiation start seems to be not as important as the TATA box. Another region in the defined distance to the TATA box may act as a transcription start after deletion of the original one. One can speculate on the effect of this deletion on several stages of the expression process (e.g. transcription initiation, mRNA stability, translation initiation) since the 5' end of the mRNA was changed by the deletion.

Only two constructs, Δ2 and Δ6*, show a significant higher expression level after derepression. Putative transcription factor binding sites of Rap1p and Gcr1p are included in the deleted sequences. In addition, the putative transcription factor binding site of QA-1F is very close to the deleted sequences of Δ6*. Noteworthy, Rap1p and Gcr1p binding sites are known to act in a synergistic manner when present in promoter sequences [21]. The general transcription factor Rap1p has diverse cellular functions (e.g. telomere structure, mating, translation, glycolysis) dependent on the sequence context of its binding site and the appropriate transcription factors [22-24]. As mentioned before, Gcr1p is the major item of regulation and coordination of glycolytic genes and is absolutely necessary for high level expression in S. cerevisiae. Binding sites of Rap1p and Gcr1p are found in close proximity in the core region of upstream activating sequence (UAS) of glycolytic genes and Gcr1p binding is alleviated by bending the DNA by Rap1p. On the other hand an adjacent Rap1p binding site is not an absolute requirement for Gcr1p dependent activation of genes. It seems that Gcr1p can facilitate the binding to its binding site when higher numbers of CT-boxes are present. Although a clear interaction of Rap1p with Gcr1p as well as Gcr1p with Gcr1p was described, some other factors are suggested to interact with Gcr1p and/or Rap1p modulating the activity of the complex. A broad knowledge on the induction mechanism was achieved during the last 3 decades.

The described essential close proximity of Gcr1p and Rap1p binding sites in functional UAS described above could not be found in the AOX1 promoter sequence. In contrast, the two binding sites are 367 bp apart. Among the putative Gcr1p binding site, its core sequence CTTCC is present 2 times in the AOX1 promoter sequence, but none of them immediately adjacent to the Rap1p binding site or another CTTCC motif. Therefore a synergistic action of these two binding sites as found in many glycolytic genes seems not to be likely. Due to the fact that the putative roles of Rap1p and Gcr1p are repressor proteins for AOX1 under derepression conditions, a new mode of (inter-) action of the two proteins for this putative novel cellular function is possible.

Figure 5:
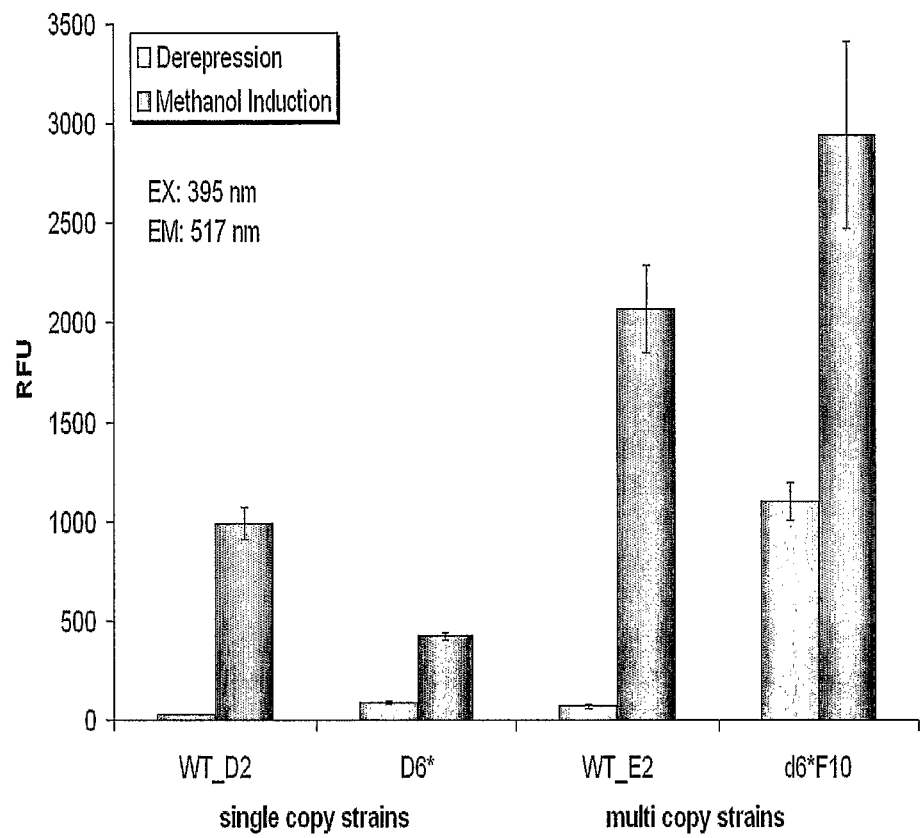

An involvement of the Δ6* deletion (including the putative Gcr1p binding site) in repression upon carbon starvation is emphasised by the observation of multicopy strains with very high GFP-Zeo expression without methanol induction. GFP-Zeo expression of the best clone of the Δ1-Δ9 series, called P. pastoris X-33 d6*F10, is shown in FIG. 5. GFP-Zeo expression is about 10% higher after derepression (60 h in microscale) in this Δ6* multicopy strain than in a single copy wild type promoter strain (X-33 GFP-Zeo D2) after methanol induction. Expression level of P. pastoris X-33 d6*F10 after methanol induction is also much higher than a multi copy strain with wild type promoter (X-33 GFP-Zeo E2).

P. pastoris AOX1 and DAS1 and H. polymorpha MOX promoter regions promote expression of the reporter enzyme beta-galactosidase (lacZ of E. coli) in S. cerevisiae [9]. Regulation pattern of these genes in S. cerevisiae is similar to their natural hosts: glucose represses gene expression. At carbon starvation conditions expression is slightly derepressed and glycerol as carbon source induces expression. Beta-galactosidase levels expressed under the control of AOX1 and DAS1 regulatory regions in S. cerevisiae are comparable to those obtained with the strong S. cerevisiae CYC1 (constitutive) and GAL2 (inducible) promoters [9]. It was demonstrated that expression driven by the MOX promoter is also induced by ethanol, methanol and oleic acid in S. cerevisiae. Another very important finding is the involvement of Adr1p in derepression/induction of the promoter. Adr1p, a positive effector of ADH2 (alcohol dehydrogenase 2) and some peroxisomal proteins in S. cerevisiae [25], is also a positive effect—or of the MOX promoter when glucose is lacking in the medium.

As mentioned before regulation pattern of the AOX1 and the MOX gene are significantly different in their natural hosts due to the derepression of MOX when glycerol is present. Using the AOX1 promoter region in H. polymorpha revealed that the AOX1 promoter is not repressed by glycerol in the heterologous host [26]. Thus, the heterologous AOX1 promoter seems to be regulated like the homologous MOX promoter. This results in the suggestion that the significant differences in regulation pattern between P. pastoris and H. polymorpha are due to the overall transcriptional response to different carbon sources in these two yeasts. Meaning, while the glycerol and glucose repression machinery are (partially) identical in P. pastoris, in H. polymorpha (like in S. cerevisiae) the situation is different and glycerol does not use the glucose repression machinery.

Two of the three putative HAP2/3/4/5 binding sites found in the AOX1 promoter sequence are within the Δ1 deletion construct and the third in Δ5. Sequence deletion of Δ1 results in an increase in promoter activity upon methanol induction while no effect on the derepression promoter level was observed. In contrast, deletion of Δ5 results in a severe decrease in promoter activity under derepression as well as induction conditions. In the Δ1 deletion a putative Aspergillus nidulans abaA binding site was found. The abaA gene product is a transcriptional activator which is involved in conidiophore (asexual reproductive apparatus) development in A. nidulans [27]. Since all putative binding sites are possible activator sequences [27], their deletion should have a negative effect on the expression level as found in the Δ5 construct. Due to the fact that both deletions are very long another binding site might be responsible for the observed effect. The fact that deletion of Δ1 has the opposite effect on the expression level indicates that one of the putative binding sites is a repressor motif, or another binding site is present which exceeds the effects of deletion of the putative HAP and abaA binding sites thereby increasing the expression level.

Nonetheless, the HAP complex is known to be responsible for upregulation of genes involved in respiratory and energy metabolism in S. cerevisiae. Regulation of respiration is controlled by oxygen level as well as the carbon source present in the medium, both mediated by the Hap complex. In the fermentative yeast S. cerevisiae, several genes and therefore functions of the respiratory chain as well as the citric acid cycle are repressed by glucose. Glucose repression of respiration is partially mediated by the Hap complex, namely by the absence of Hap4p as long as glucose is present. In contrast, oxygen-dependent regulation seems to be regulated by Hap1p [28]. Homologues of the Hap complex genes were isolated in the respiratory yeast K. lactis. Genes involved in respiration are constitutively expressed in respiratory yeasts, even in presence of glucose. To date, almost every respiratory chain gene has been shown to be regulated independently from the Hap complex [29]. The role of the Hap complex seems to be in coordinating carbon and nitrogen assimilation, as has also been found in S. cerevisiae [30] and Aspergillus nidulans [29].

The first step in the methanol utilisation pathway, mainly catalysed by the AOX1 gene product in P. pastoris, is oxygen-consuming. Most of the genes involved in energy metabolism and almost every gene encoding for oxygen-consuming enzymes is regulated by oxygen, mainly by Hap1p and/or Hap2/3/4/5p [28]. When grown on methanol as sole energy and carbon source, the methanol utilisation pathway results in carbon assimilation and energy production. An involvement of the Hap complex recognition motif TTCCAA in the regulation of the AOX1 promoter makes intuitive sense.

The Δ4 construct, which includes a second putative HSF binding site, resulted in a 30% decrease of promoter activity after derepression and induction. Therefore HSF is a general enhancer of AOX1 gene expression under derepressing as well as induction conditions. In S. cerevisiae several stress conditions like heat shock, oxidative stress and glucose starvation led to the activation of HSF. It has also been demonstrated that the protein kinase Snf1p, one of the "metabolic master switches", is involved in phosphorylation and therefore activation of HSF upon carbon starvation [31]. Thus an involvement of HSF in full activation of AOX1 upon glucose starvation (with or without induction) occurs.

Expression studies on the AOX1 promoter using truncated versions as well as variants with deleted sequences are disclosed in the prior art [32, 33].

TABLE 14

Results of the promoter studies by Inan et al. [32, 33]; Induction was performed with 0.5% methanol as carbon source, repression with 0.5% methanol and 0.5% ethanol; Start positions denote the 5' end of the sequence in the AOX1 promoter in respect to the translation start point (ATG)

| Promoter fragment | Deletion by referring to SEQ ID No. 1 | relative activity [%] | |
|---|---|---|---|
| | | induced | repressed |
| InanABCDEF | — | 100 | 3.1 ± 0.3 |
| Inan_BCDEF | 7 to 152 (−947 to −802) | 76 ± 5 | 1.9 ± 0.2 |
| Inan_CDEF | 1 to 292 (−947 to −661) | 49 ± 4 | 2.2 ± 0.5 |
| Inan_DEF | 1 to 432 (−947 to −521) | 14 ± 3 | 1.3 ± 0 |
| Inan_EF | 1 to 559 (−947 to −394) | 24 ± 7 | 1.8 ± 0 |

TABLE 14-continued

Results of the promoter studies by Inan et al. [32, 33]; Induction was performed with 0.5% methanol as carbon source, repression with 0.5% methanol and 0.5% ethanol; Start positions denote the 5' end of the sequence in the AOX1 promoter in respect to the translation start point (ATG)

| Promoter fragment | Deletion by referring to SEQ ID No. 1 | relative activity [%] induced | repressed |
|---|---|---|---|
| Inan_F | 1 to 798 (−947 to −245) | 7 ± 2 | 1.8 ± 0.2 |
| InanA_CDEF | 153 to 292 (−801 to −661) | 63 ± 3 | 2.1 ± 0.2 |
| InanAB_DEF | 293 to 432 (−660 to −521) | 109 ± 12 | 3.8 ± 0.4 |
| InanABC_EF | 433 to 559 (−520 to −394) | 128 ± 6 | 5.0 ± 0.6 |
| InanABCD_F | 560 to 798 (−393 to −245) | 16 ± 1 | 0.8 ± 0.2 |

The construct Inan_BCDEF, which starts at 153 (−801) (Table 14) revealed a binding site of at least one activator protein upstream of 153 (−801). Candidates for this activator binding site are the binding sites of Hap1p (52 to 66, −902 to −888) and HSF (135 and 155, −819 to −799) on the complementary strand found with MatInspector. Truncation at the SacI restriction site (210-215 (−744 to −739)) resulted in a promoter reaching nearly wild type promoter activity (Geoff Lin Cereghino, Poster, Sixth Meeting on "Current Topics in Gene expression and Proteomics", San Diego, Oct. 19-22, 2003). To reach the wild type promoter level with the SacI truncated promoter construct (pHWG0, Geoff Lin Cereghino, poster), a second binding site for a repressor protein may be present upstream of 210 (−744) whose deletion has the same impact, but in the opposite direction, on the promoter activity. The location of the repressor protein is between 169 (−784) and 210 (−744) because the Δ1 construct (Δ 169 (−784) to 234 (−719)) contains a repressor binding site. Deletion of Δ1 results in a 20% increase of promoter activity (Table 14) which is in the range of the decrease by deletion of the activator protein binding site.

By comparison with Δ4 (Δ 508 (−445) to 550 (−403)) the location of the repressor binding site can be further refined to a sequence between 433 (−520) and 508 (−445) because the Δ4 deletion includes a positively acting transcription factor, HSF at 516 to 536 (−438 to −418). If the positively acting HSF (if it is HSF) is located within the proposed region, a stronger effect of the repressor binding site between 433 and 508 (−520 and −445) can be suggested. If the binding site for HSF is located in the region between 508 and 536 (−445 and −418) another activator binding site is located between 536 and 560 (−418 and −393). If not, it is likely to be the same binding site. As the InanABCD_F (Δ 560 to 709 (−393 to −245)) variant with only 16% wild type activity also the Δ5 construct (624 to 682 (−329 to −271)) results in a decrease of about 70% of the wild type level. As expected, deletion of the Inan B fragment from the full length promoter (results in InanA_CDEF) as well as from Inan_BCDEF (results in Inan_CDEF) results in a decrease to 63 and 64% of the longer fragment, respectively. In contrast, while deletion of the C fragment from the full length promoter results in an increase of about 10% in promoter activity, deletion from the truncated Inan_CDEF fragment leads to a decrease from 49 to 14% (Table 14). The explanation is a synergistic binding of transcription factors dependent on the context of their binding sites. Between 713 and 760 (−241 to −194) a last activator protein binding site is located (Geoff Lin Cereghino, Poster San Diego). Again, by the Δ7 construct (Δ 729 to 763, −225 to −191) the location of the activator could be refined downstream to 729 (−225).

To conclude, several regions were found which had a strong impact on the expression level of the AOX1 promoter. Combining all known regulatory sites from the example provided herein and from other authors, excluding the regions containing the TATA box and the transcription initiation site, at least 10 regulatory sites exist on the $P_{AOX1}$ promoter sequence.

The data provided revealed the orchestral regulation of the AOX1 promoter: several factors are necessary to bind to the DNA for maximum expression level. Under inducing conditions several positive acting transcription factors (activators) bind to the DNA while most repressor proteins did not bind resulting in high level expression. While derepressed, the promoter activity reached only a small percentage (~3%) of the induced level. This is most likely due to less activator and more repressor proteins binding to the promoter region. Under repressing conditions one can assume that no activators and several repressors bind to the DNA with a further increase of the repressor/activator ratio under repressing conditions.

It has been demonstrated for the glucose repressed ADH2 (alcohol dehydrogenase 2) promoter of *S. cerevisiae* that binding of activator proteins (e.g. Adr1p) immediately adjacent to nucleosomes lead to destabilisation and therefore rearrangement of the chromatin upon derepression. The rearrangement takes place in the region of the TATA box and the transcription initiation site therefore increasing their accessibility. Due to the higher accessibility formation of a stable pre-initiation complex takes place therefore increasing the promoter activity to a basal level. Among the binding of several transcription factors to enhance the PAOX1 driven expression, a similar mechanism, at least for derepression is assumable. Taken all the data and assumptions together, regulation of the AOX1 promoter is highly complex and the putative binding sites of several (positively and negatively acting) transcription factors reveals highly coordinated machinery which is able to integrate a wide variety of signals for the regulation of the AOX1 promoter.

VI) PCR Mutagenesis of AOX1 Promoter

Here it has been demonstrated that specific mutations within core sequences of transcription factor binding sites result in significant alterations of their effector force. Assembly a few activator and repressor proteins act on the AOX1 promoter to result in its very strong regulation (almost no activity under glucose, very high activity in methanol). Therefore random mutagenesis of the AOX1 promoter should result in several promoter variants with destroyed or reduced repressor binding site activities. A set of PCR reactions with different mutation rates was performed. The resulting promoter variants were transformed into *P. pastoris* GFP-Zeo Mut$^s$ A9 strain where the AOX1 gene was replaced by the GFP-Zeo strain. Replacement of the wild type AOX1 promoter by mutagenized promoter variants should occur to a particular rate. Screening for promoter variants with higher expression rate when glucose is present in the medium was done on MD-Zeo agar plates.

Spreading on MD agar plates containing 100 µg/ml ZEO-CIN™ resulted in plates blotched with *Pichia pastoris* cells and no single colonies are apparent. It seems that selection pressure was not enough to repress growth of the wild type strain. Although no fluorescence could be detected in the *P. pastoris* GFP-Zeo Mut$^s$ A9 strain when glucose is present, a few GFP-Zeo proteins might be expressed in the cell conferring ZEOCIN™ resistance. To test higher Zeocin™ concentrations for growth inhibition of the GFP-Zeo Mut$^S$ A9 strain drop tests as described earlier were performed.

Figure 6:
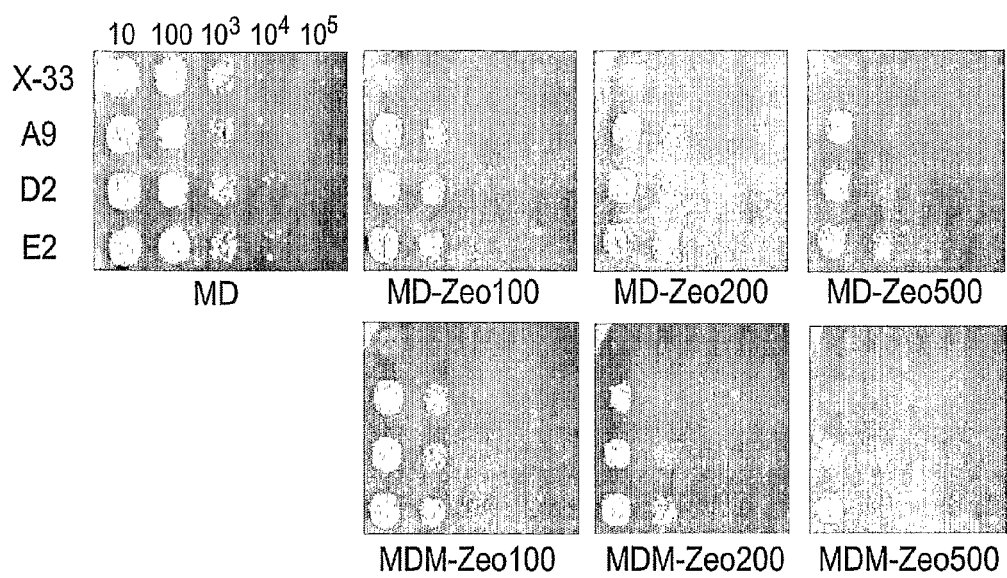

As one can clearly see in FIG. 6 increase to 200 μg/ml did not decrease cell viability (compared to 100 μg/ml) of *P. pastoris* strains bearing a GFP-Zeo gene under the control of the AOX1 promoter, but increase to 500 μg/ml did. It was expected that mutagenesis of the promoter should result in only slightly increased expression levels therefore a selection pressure of 500 μg/ml ZEOCIN™ seems to be too high. Finally 350 μg/ml were chosen for all further screenings of mutagenesis promoter variants.

Due to the very complex transcriptional regulation with many promoter regions involved a random mutagenesis approach using a high mutagenesis rate is advantageous.

Example 2

Generation of Promoter Deletions

Based on the results of example 1a second generation of deletion variants was generated. In contrast to the first series in these new deletion constructs only small and specific sequence stretches of the putative transcription factor binding sites (5-15 bp) were deleted (Table 15).

TABLE 15

Effects of deletion of specific transcription factor binding sites on the expression level upon derepression (glucose starvation) and methanol induction. Mutations Δ1-Δ9 as well as combinations of single mutations are also quoted. All numbers are relative promoter activities compared to the wild type promoter activity under the same conditions.

| Deletion | Bereich von Seq ID No. 1 | Region | Deletion (marked bold, underlined) and adjacent 5 nucleotides (5' and 3') | positive Effect |
|---|---|---|---|---|
| ΔHap1 | -900 to -896 | Inan A | GCCATCCGACATCCA | increased expression under under induction conditions |
| ΔHsf_1 | -812 to -805 | Inan A | GGACCTCCACTCCTCTTC | generation of multi-copy strains, increased expression under under induction conditions |
| Δ1 | -784 to -719 | Inan B | CCACTTTTGCCATCGAAAAACCAGCCCAGTTATTGGGCTTGATTG-GAGCTCGCTCATTCCAATTCCTTCTATTAGG | increased expression under under induction conditions |
| ΔHap2345_1 | -758 to -754 | Inan B, Δ1 | CAGTTATTGGGCTTG | generation of multi-copy strains |
| ΔHap2345_2 | -748 to -744 | Inan B, Δ1 | GCTTGATTGGAGCTC | generation of multi-copy strains |
| ΔabaA | -735 to -730 | Inan B, Δ1 | TCGCTCATTCCAATTC | generation of multi-copy strains |
| ΔStre | -673 to -669 | Inan B | TGGCCCCCCTGGCGA | increased expression under under induction conditions |
| Δ2 | -650 to -604 | Inan C | TTTGTTTATTTCCGAATGCAACAAGCTCCGCATTACACCCGAACAT-CACTCCAGATG | higher expression under derepressing condtions |
| ΔRap1 | -619 to -615 | Inan C, Δ1 | ATTACACCCGAACAT | generation of multi-copy strains |
| Δ3 | -590 to -561 | Inan C | GCTTTCTGAGTGTGGGGTCAAATAGTTTCATGTTCCCCAA | |
| ΔAdr1 | -583 to -577 | Inan C, | GAGTGTGGGGTCAAATA | generation of multi-copy strains |
| Δ4 | -445 to -403 | Inan D | AGTTGACAAGACAAACGGTATGCCGACTTTTG-GAAGTTTCTTTTTGACTTGGT | |
| ΔHsf_2 | -437 to -430 | Inan D, Δ4 | AAAAAGAAACTTCCAAAA | |
| Δ5 | -329 to -271 | Inan E | GAACCCCGGTGCACCTGTGCCGAAACGCAAATGGGGAAACAC-CCGCTTTTTGGATGATTATGCATTGTC | |
| ΔHap2345_3 | -286 to -282 | Inan E, Δ5 | CGCTTTTTGGATGAT | generation of multi-copy strains |
| ΔMat1MC | -271 to -267 | Inan E, Δ5° | TATGCATTGTCTCCA | |

TABLE 15-continued

Effects of deletion of specific transcription factor binding sites on the expression level upon derepression (glucose starvation) and methanol induction. Mutations Δ1-Δ9 as well as combinations of single mutations are also quoted. All numbers are relative promoter activities compared to the wild type promoter activity under the same conditions.

| Deletion | Bereich von Seq ID No. 1 | Region | Deletion (marked bold, underlined) and adjacent 5 nucleotides (5' and 3') | positive Effect |
|---|---|---|---|---|
| Δ6 | −260 to −231 | Inan E & F | TCCACATTGTATGCTTCCAAGATTCTGGTGGGAATACTGC | higher expression under derepressing conditions, |
| Δ6* | −260 to −231<br>−217 to −216 | Inan E & F<br>Inan F | TCCACATTGTATGCTTCCAAGATTCTGGTGGGAATACTGC<br>TAGCCTAACGTT | generation of super-clones with high expression under derepressing conditions |
| ΔGcr1 | −252 to −248 | Inan E<br>Δ6 | GTATGCTTCCAAGAT | generation of multi-copy strains |
| Δ7 | −225 to −191 | Inan F | ACTGCTGATAGCCTAACGTTCATGATCAAAATTTAACTGTTCTAA | |
| ΔQA-1F | −207 to −193 | Inan F,<br>Δ7 | TTCATGATCAAAATTTAACTGTTCT | generation of multi-copy strains, increased activity under derepression conditions |
| ΔQA-1Fzus | −218 to −213<br>−207 to −193 | Inan F,<br>Δ7 | ATAGCCTAACGTTCATGATCAAAATTTAACTGTTCT | increased activity under derepression conditions |
| ΔHsf_2_dHap2345_1 | −758 to −754<br>−437 to −430 | Inan B<br>Δ1<br>Inan D,<br>Δ4 | CAGTTATTGGGCTTG<br>AAAAGAAACTTCCAAAA | generation of multi-copy strains |
| ΔHsf_2_dHap2345_1zus | −758 to −754<br>−747 to −745 | Inan B<br>Δ1<br>Inan B,<br>Δ1 | CAGTTATTGGGCTTGATTGGAGCT<br>AAAAGAAACTTCCAAAA | |
| ΔHsf_2_Mat1MC | −437 to −430<br>−437 to −430<br>−271 to −267 | Inan D,<br>Δ4<br>Inan D,<br>Δ4<br>Inan E,<br>Δ5° | AAAAGAAACTTCCAAAA<br>TATGCATTGTCTCCA | generation of multi-copy strains |
| Δ8 | −170 to −154 | Inan F | ACAGCAATATATAAACAGAAGGAAGCT | |
| Δ9 | −131 to −93 | Inan F | ACCTTTTTTTTTATCATCATTATTAGCTTACTTTCATAAT-TGCGACTGG | |
| Δ2Δ6 | −650 to −604<br>−260 to −231 | Inan C<br>Inan E & F | TTTGTTTATTTCCGAATGCAACAAGCTCCGCATTACACCCGAACAT-CACTCCAGATG<br>TCCACATTGTATGCTTCCAAGATTCTGGTGGGAATACTGC | generation of multi-copy strains |
| Δ736-41 | −218 to −213 | Inan F,<br>Δ7 | ATAGCCTAACGTTCAT | |
| Δ737-38 | −217 to −216 | Inan F,<br>Δ7 | TAGCCTAACGTT | |
| ΔInD-d4m | −402 to −394 | Inan D | CTTGTTTGGTATTGATTGA | |
| ΔD-d4 | −520 to −446 | Inan D | CTTGGAACCTAATATGACAAAAGCGTGATCTCATCCAAGAT-GAACTAAGTTTGGTTCGTTGAAATGCTAACGGCCAGTTGCTTGG | |
| Δ1-1 | −784 to −763 | Inan B,<br>Δ1 | CCACTTTTGCCATCGAAAAACCAGCCCAGTTA | |
| Δ1-1 | −762 to −741 | Inan B,<br>Δ1 | AGCCCAGTTATTGGGCTTGATTGGAGCTCGCT | |
| Δ1-3 | −740 to −719 | Inan B,<br>Δ1 | GGAGCTCGCTCATTCCAATTCCTTCTATTAGG | |

TABLE 15-continued

Effects of deletion of specific transcription factor binding sites on the expression level upon derepression (glucose starvation) and methanol induction. Mutations Δ1-Δ9 as well as combinations of single mutations are also quoted. All numbers are relative promoter activities compared to the wild type promoter activity under the same conditions.

| Deletion | Bereich von Seq ID No. 1 | Region | Deletion (marked bold, underlined) and adjacent 5 nucleotides (5' and 3') | positive Effect |
|---|---|---|---|---|
| Δ1-SacI | -762 to -744 | Inan B, Δ1 | CCACTTTTGCCATCGAAAAACCAGCCCAGTTATTGGGCTTGAT-TGGAGCTC | |
| Ohi, et al, AOX2 UAS | -228 to -199 | Inan F, Δ7 | AATACTGCTGATAGCCTAACGTTCATGATCAAAATAATAC | |
| Ohi, et al, AOX2, UAS | -369 to -337 | Inan E | TAATCTCATTAATGCTTAGCGCAGTCTCTCTATCGCTTTAATC | |
| Ohi, et al, AOX2, URS2 | -333 to -294 | Inan E | TTCTGAACCCCGGTGCACCTGTGCCGAAACGCAAATGGGGAAACACCCGC | |

Materials and Methods:

a) Mutagenesis:

All deletions were introduced using the two-stage site-directed mutagenesis-protocol according to Wang et al. [34]. In a first step two separate reactions (one for a forward and one for a reverse primer) were assessed (100 ng pAOX template, 15 pmol primer, 200 μM of each dATP, dTTP, dCTP and dGTP, 2.5 U PfuUltra™ polymerase in a total volume of 50 μl in appropriate buffer conditions). 25 μl of these 2 PCR reactions were combined and a second PCR reaction step was performed.

1 μl of DpnI restriction enzyme (10 u/μl) was added to 30 μl of the second PCR reaction step and incubated for 1 h at 37° C. 1-5 μl of DpnI digested PCR reaction were transformed into electrocompetent E. coli cells [16] and plated on LB-Amp plates after a 1 h regeneration time in SOC medium.

TABLE 16

Primers for site-directed mutagenesis of transcription factor binding site deletions

| Deletion | Name | Sequenz (5' --> 3') | SEQ ID No. |
|---|---|---|---|
| Hap1 | Hap1fw | GAATGAAACCTTTTTGCCATA-TCCACAGGTCCATTCTCAC | 53 |
| | Hap1rv | GAATGGACCTGTGGATATGGCAAAAAG-GTTTCATTCAACC | 54 |
| Hsf_1 | Hsf_1fw | CCGTTGCAAACGCAG-GACCTCTTCTCCTCAACACCCAC | 55 |
| | Hsf_1rv | GTGTTGAGGAGAAGAGGTCCT-GCGTTTGCAACGGTCTG | 56 |
| Hap2345_1 | Hap2345_1fw | CGAAAAACCAGCCCAGTTGCTTGATTG-GAGCTCGCTCATTCC | 57 |
| | Hap2345_1rv | GAGCGAGCTCCAATCAAGCAACTGG-GCTGGTTTTTCGATG | 58 |
| Hap2345_2 | Hap2345_2fw | CAGCCCAGTTATTGGGCT-TGAGCTCGCTCATTCCAATTCC | 59 |
| | Hap2345_2rv | GGAATTGGAATGAGCGAGCTCAAGC-CCAATAACTGGGCTG | 60 |
| ABAA | ABAAfw | GGCTTGATTG-GAGCTCGCTAATTCCTTCTATTAGGC-TAC | 61 |
| | ABAArv | GTAGCCTAATAGAAGGAATTAGC-GAGCTCCAATCAAGCC | 62 |
| Stre_1 | Stre_1fw | GCCTGTCTATCCTGGCCGGCGAG-GTTCATGTTTGTTTATTTC | 63 |
| | Stre_1rv | CAAACATGAACCTCGCCGGCCAG-GATAGACAGGCTAATAAAG | 64 |
| Rap1 | Rap1fw | GCAACAAGCTCCGCATTACAACAT-CACTCCAGATGAGG | 65 |

TABLE 16-continued

Primers for site-directed mutagenesis of transcription factor binding site deletions

| Deletion | Name | Sequenz (5' --> 3') | SEQ ID No. |
|---|---|---|---|
|  | Rap1rv | CCTCATCTGGAGTGATGTTGTAATGCG-GAGCTTGTTGC | 66 |
| Adr1 | Adr1fw | CCAGATGAGGGCTTTCTGAGT-GAAATAGTTTCATGTTCCC | 67 |
|  | Adr1rv | GGGAACATGAAACTATTTCACT-CAGAAAGCCCTCATCTGG | 68 |
| Hsf_2 | Hsf_2fw | GCCAGTTGGTCAAAAACAAAAGTCG-GCATACCGTTTGTC | 69 |
|  | Hsf_2rv | CGGTATGCCGACTTTTGTTTTTGAC-CAACTGGCCGTTAGC | 70 |
| Hap2345_3 | Hap2345_3fw | CAAATGGGGAAACACCCGCTTATGAT-TATGCATTGTCTCCAC | 71 |
|  | Hap2345_3rv | GAGACAATGCATAATCATAAGCGGGT-GTTTCCCCATTTGCG | 72 |
| Mat1MC | Mat1MCfw | GCTTTTTGGATGATTATGCCTCCACAT-TGTATGCTTCCAAG | 73 |
|  | Mat1MCrv | CTTGGAAGCATACAATGTGGAG-GCATAATCATCCAAAAAGC | 74 |
| Gcr1 | Gcr1fw | CATTGTCTCCACATTGTAT-GAAGATTCTGGTGGGAATACTGC | 75 |
|  | Gcr1rv | GTATTCCCACCAGAATCTTCATACAAT-GTGGAGACAATGC | 76 |
| QA-1F | QA-1Ffw | GCTGATAGCCTAACGTTCAT-GTTCTAACCCCTACTTGACAGC | 77 |
|  | QA-1Frv | GTCAAGTAGGGGTTAGAACATGAACGT-TAGGCTATCAGCAG | 78 |
| 736-741 | d736-41fw | GGAATACTGCTGATAGCTTCATGAT-CAAAATTTAACTGTTC | 79 |
|  | d736-41rv | GTTAAATTTTGATCATGAAGCTAT-CAGCAGTATTCCCACC | 80 |
| 737-738 | d737-38fw | GGAATACTGCTGATAGCCACGTTCATG-ATCAAAATTTAACTG | 81 |
|  | d737-38rv | GTTAAATTTTGATCATGAACGTG-GCTATCAGCAGTATTCC | 82 | b) *Pichia Pastoris* Transformation and Characterisation of Clones:

Plasmids constructed as described above were prepared and transformed into *Pichia pastoris* as described in example 1.

Results and Discussion:

A strong effect on the expression level is observed with the short mutations of example 2 as already described for the larger deletions of example 1 where all mutations have a significant either positive or negative effect on the promoter activity. Short deletions of specific transcription factor binding sites have strong effects on the promoter activity and give a more precise information about the regulatory properties of individual regulatory sites (e.g transcription factor binding sites). Gcr1 is of special interest since its binding site is included in the Δ6 deletion. Sequencing of the promoter region of a PAOXΔ6 deletion mutant and a colony PCR products of genomic DNA of *Pichia pastoris* clones revealed an additional deletion in the promoter region (Deletion of the nucleotides 737 to 738 (−217 to −216) of SEQ ID No. 1). Due to the fact that this promoter variant leads to an increased promoter activity resulting consequently in a higher expression rate under derepressing conditions the additional mutation can be introduced into a promoter according to the present invention to increase protein expression under these conditions.

Promoter activity of QA-1F clones with an additional deletion (Deletion of nucleotides 736 to 741 (−218 to −213) of SEQ ID No. 1) is significantly different compared to the ΔQA-1F promoter without this additional deletion: The activity changes from ~30% (derepression) and ~100% (Induction) of wild type activity (AOX1ΔQA-1F, see table 15) to ~140% and ~70%, respectively (AOX1ΔQA-1Fzus, see table 15). The additional deletion of these 6 nucleotides seems to have a dramatic influence on the promoter activity. Thus a new promoter variant bearing this mutation (Δ736-741) was introduced by the site-directed mutagenesis protocol as described above. Both mutations which came up two times accidentally and independently in this region resulted in an increase of the promoter activity under derepressing conditions. It is notable that there is an increase in promoter activity although there is a second and most probably negatively influencing mutation in both constructs.

A combination of Δ2 and Δ6 (Δ2Δ6) was generated similar to single deletions by overlap extension PCR. It is clearly shown in table 17 that a deletion of both fragments results in a very strong decrease of promoter activity under derepression as well as induction conditions. Since there is no additional TA deletion in this construct compared to the Δ6* construct as aforementioned also this result supports the speculation that the accidentally arised additional mutation (Δ737-38) is responsible for the increase in promoter activity upon carbon starvation.

Several deletions result in a dramatic decrease of promoter activity (e.g. Hsf, but also Hap1 and Hap2345_1). These putative binding sites are brilliant targets for a sequence duplication which should result in an increase of promoter activity.

Interestingly, in 2 out of 4 clones of the Δ736-741 variant generated by site-directed mutagenesis a new deletion of 9 nucleotides (TTGGTATTG) at position 552 to 560 (−402 to −394) was found. The effect that deletions were found in a distinct region was also found in ΔHsf_2 constructs. Such an effect is expected to be due to local sequence homology. Thus such additionally deleted regions (Δ552-560, Δ737-38 and Δ736-41) and the sequences in close proximity (5 bp up- and downstream) are also putative transcription factor binding sites and therefore highly interesting targets for deletions and duplications. The deletion variant Δ736-41 results in an enhanced reduction of the expression level under methanol inducing conditions.

Figure 7:
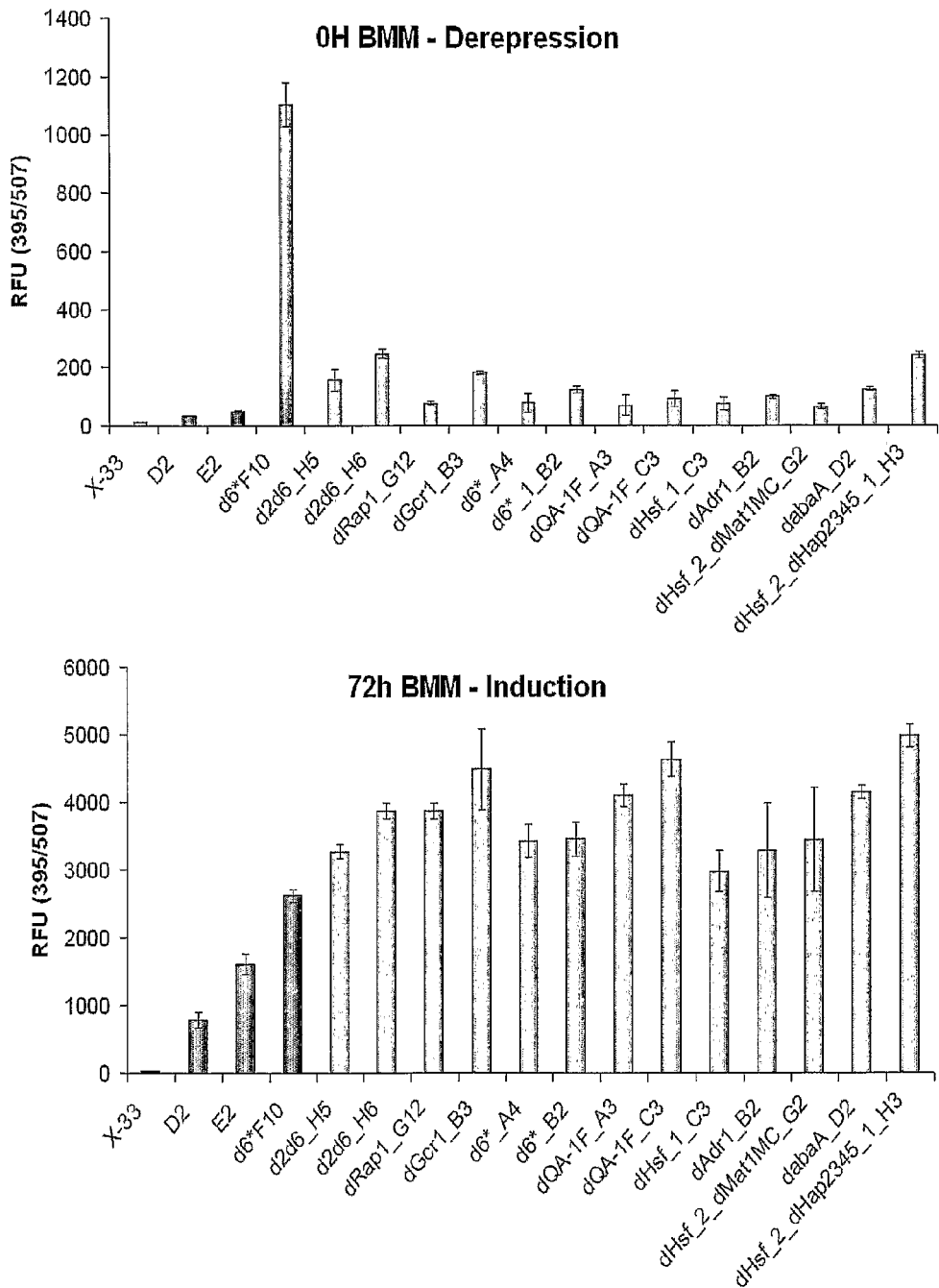
FIG. 7 shows the expression level of several multicopy strains in comparison to reference strains; a) activity under derepressing conditions; b) activity after methanol induction.
Figure 8:
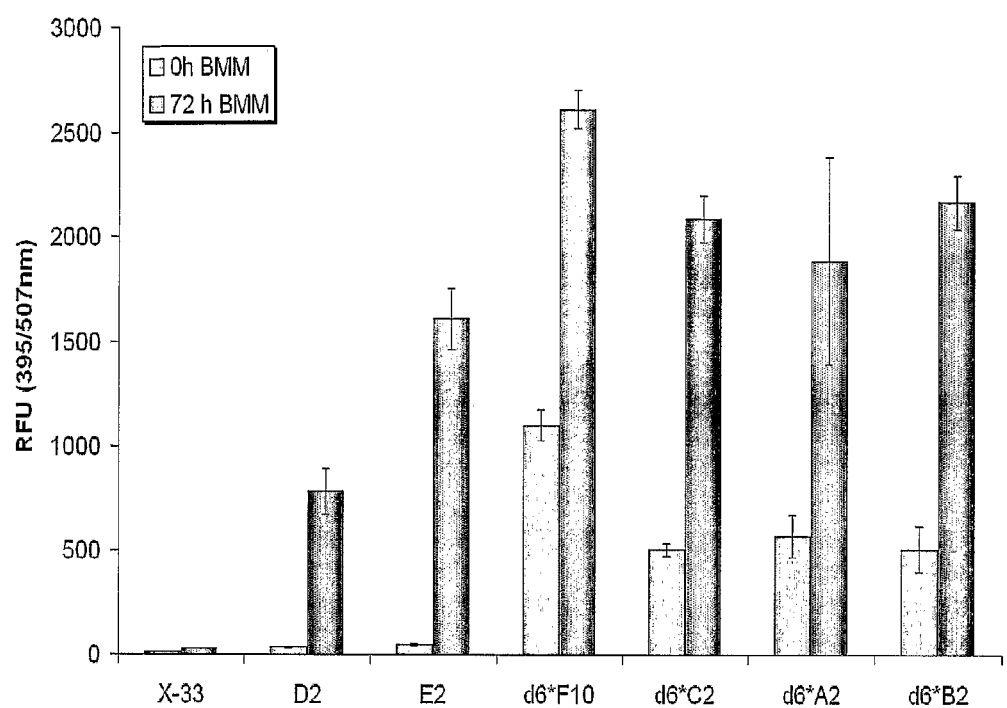
FIG. 8 shows the expression level of Δ6* multicopy strains under derepressing and induced conditions compared to reference strains.

Multicopy-Strains:

In most cases generation of multicopy strains results in GFP-Zeo super expressing strains. In many cases these strains have higher expression levels than the d6*F10 strains, mainly under methanol inducing conditions. The generation of multicopy strains was achievable with several constructs, especially with the Δ6* construct, the double deletion d2d6, constructs including Δ1, Δ2 and Δ6* deletions as well as e.g. Gcr1, Rap1, abaA, Hap2345_1, but also e.g. QA-1F, Adr1, Hsf_2_Mat1MC and Hsf_2_Hap2345_1 (see FIG. 7). In these strains a higher expression rate under inducing conditions is found compared to the d6*F10 strain. In contrast the d6*F10 strain was able to produce more GFP-Zeo than any other strain generated up to know under derepressing conditions. Repeated transformation of Δ6* construct into *Pichia pastoris* results in a high number of multicopy strains with comparable activity to the d6*F10 strain, especially under derepressing conditions (FIG. 8).

Using wild-type promoter constructs, a much lower frequency of multicopy-strains (e.g. E2 strain) was observed than using promoter variants. Although 2-4 times more transformants were analysed, the expression level of the best transformant E2 is only twice as high as single copy transformants. In conclusion transformation of promoter variants result in a higher frequency of multicopy strains and these strains are multiple more productive than multicopy wild-type promoter strains.

Example 3

Alternative Reporter Proteins

To test the practicability of all the GFP-Zeo results for other, basically well expressed and industrially relevant proteins (e.g. enzymes) some promoter variants were cloned in front of such reporter enzymes (e.g. PaHNL5α and HRP).

Cloning:

Promoter variants were cloned into vectors pPICZαB-HRP-WT [35] und pGAPZ A-PaHNL5α. For the promoter exchange in pPICZαB-HRP-WT a NdeI restriction site was inserted at the 5' end of the promoter by site-directed mutagenesis (100 ng vector as template, primer Nde1PICZfor and Nde1PICZrev—see table 18). The resulting vector was called pPICZαB-NdeI-HRP-WT.

TABLE 18

Primer for site-directed mutagenesis for introduction of a NdeI restriction site in pPICZαB-HRP-WT and for promoter exchange

| Name | Sequence (5' --> 3') | Seq ID No. |
|---|---|---|
| Nde1PICZfor | GAGATCAGATCTAACATATGCCAAAGACGAAAG-GTTG | 83 |
| Nde1PICZrev | CAACCTTTCGTCTTTGGCATATGTTAGATCTG-ATCTC | 84 |
| AOX1NDE1 | AAACATATGAGATCTAACATCCAAAGACGAAAGG | 85 |
| AOX1rev | TGGTTGAATTCTTTCAATAATTAGTTG | 86 |

For the pGAPZ A-PaHNL5α expression clone the PaHNL5α gene was first cloned from a pHIL-D2 vector (Glieder, A., et al. Angew. Chemie Int. Ed. 2003) into a pGAPZ A vector, resulting in plasmid pGAPZA-PaHNL5α. Cloning of promoter variants into pGAPZ A-PaHNL5α could be done directly after EcoRI/BglII digestion of pGAPZ A-PaHNL5α and pAOXΔ plasmids. For an exchange in pPICZαB-NdeI-HRP-WT the promoter variants were amplified by PCR using primers AOX1NDE1 and AOX1rev (see table 18, 10 ng pAOXΔ, 10 pmol primer AOX1NDE1 and AOX1rev, 200 μM each dNTP, 0.6 u Phusion™ Polymerase in appropriate buffer conditions and a total volume of 50 μl). The PCR products and the pPICZαB-NdeI-HRP-WT plasmid were cloned employing NdeI/HindIII restriction sites.

Transformation, Growth and Enzyme Assays:

For *Pichia pastoris* transformation all HRP vectors were linearised by NdeI and all PaHNL5α plasmids by BglII. Transformation was performed as described in example 1. Growth of *P. pastoris* strains was also done as described in example 1 with only a few exceptions. The amount of initial BMD (1%) was increased to 350 μl and after 60 hours 100 μl of culture were taken for centrifugation (4000 rpm, 4° C., 10 min). Methanol induction was done exactly as described in example 1.

50 μl (derepression or 10 μl (induction) of supernatant from centrifugation were taken HNL assay and 15 μl at both conditions for HRP assay.

HRP assay (according to [35]):

15 μl supernatant were added to 150 μl 1 mM ABTS/2, 9 mM $H_2O_2$ in 50 mM NaOAc buffer pH 4.5 in PS microtiter plates. The absorption was followed for 5 minutes at 405 nm in a Spectramax Plus384 platereader (Molecular Devices, Sunnyvale, Calif., USA).

HNL assay (according to [36]):

50 μl or 10 μl of supernatant were added to 100 or 140 μl 0.05M phosphate-citrate buffer pH 5.0 in an UV-Star microtiter plate. The reaction was started by adding 50 μl 0.06 M mandelonitrile solution (in 0.003 M phosphate-citrate buffer pH 3.5) and followed for 5 minutes at 280 nm in a Spectramax Plus384 platereader (Molecular Devices, Sunnyvale, Calif., USA).

Results and Discussion:

The results using the alternative reporter proteins PaHNL5α and HRP clearly show the transferability of promoter activity detected using GFP-Zeo (Table 17).

Due to the lower sensitivity of the HRP assay the expression level at derepressing conditions was below the detection limit. Thus HRP expression could not be determined under derepressing conditions.

TABLE 17

Promoter activity of several AOX1 promoter variants with alternative reporter enzymes (in brackets the relative activity compared to the wild type promoter under the same conditions is quoted (derepression and induction, respectively))

| Promoter | GFP-Zeo Derepr. | GFP-Zeo Methanol | PaHNL5α Derepr. [mU/min] | PaHNL5α Methanol [mU/min] | HRP Derepr. [mU/min] | HRP Methanol [mU/min] |
| --- | --- | --- | --- | --- | --- | --- |
| P(AOX1) | 27.3 (100%) | 987 (100%) | 2.58 (100%) | 69.5 (100%) | n.d. | 20.3 (100%) |
| P(AOX1)Δ1 | 29.5 (108%) | 1188 (120%) | 2.37 (92%) | 100 (144%) | n.d. | 26.9 (132%) |
| P(AOX1)Δ2 | 43.0 (157%) | 399 (40%) | n.d. | 91.7 (132%) | n.d. | 9.6 (47%) |
| P(AOX1)Δ6* | 89.9 (329%) | 422 (42%) | 8.65 (335%) | 51.7 (74%) | n.d. | 17.5 (86%) |
| P(AOX1)Δ2Δ6 | 9.9 (36%) | 336 (34%) | 1.29 (50%) | 37.5 (54%) | n.d. | 9.9 (49%) | n.d. not detectable

To transfer the multicopy selection to the alternative reporter systems, AOX1 promoter variants were cloned in the appropriate HRP and PaHNL5α plasmids in front of the ZEOCIN™ resistance gene thus replacing the TEF1 promoter.

Example 4

Alternative Reporter Protein GFP

To test the promoter variants with GFP, promoter variants described in examples 1 and 2 were cloned in front of a cycle-3 GFP gene.

Cloning:

Internal BamHI and XhoI restriction sites in the cycle-3 GFP in vector pAOX were deleted by site-directed mutagenesis employing primers Bam-del-f and Xho-del-f (Table 19) and 100 ng vector as template. The GFP Fragment was amplified by PCR from the resulting plasmid (10 ng) employing primers GFP-Zeo forw (Seq. ID No. 4, Table 7, 10 pmol) and wtGFP-XhoI-r (Table 19, 10 pmol) and Phusion™ polymerase under appropriate conditions. The resulting PCR product could be cloned into vector pPICZ B employing EcoRI/XhoI restriction cut and ligation using T4 DNA Ligase. The resulting plasmid was named pPICZ-GFP.

Cloning of all promoter variants into pPICZ-GFP could be done directly after BglII/EcoRI digestion of pPICZ-GFP and pAOX☐ plasmids.

TABLE 19

Primer for site-directed mutagenesis of the cycle 3-GFP in vector pAOX and amplification of the GFP Fragment thereof.

| Name | Sequence (5'→3') | Seq. ID No. |
| --- | --- | --- |
| Bamdel-f | cgccacaacattgaagatggttccgttcaactagcagaccattatc | 87 |
| Xho-del-f | ggaaacattctcggacacaaacttgagtacaactataactcacacaatg | 88 |

TABLE 19-continued

Primer for site-directed mutagenesis of the
cycle 3-GFP in vector pAOX and amplification
of the GFP Fragment thereof.

| Name | Sequence (5'→3') | Seq. ID No. |
|---|---|---|
| wtGFP-XhoI-r | atctcgagttacttgtacaattcatccatgccatgt-gtaatccc | 89 |

Transformation, Growth and GFP Detection:

For *Pichia pastoris* transformation all plasmids were linearized by BglII. Transformation was performed as described in example 1. After transformation and a 2 h regeneration phase cells were plated on YPD-Zeo agar plates containing 100 µg/ml ZEOCIN™.

Growth of *Pichia pastoris*, methanol induction and measurement of GFP fluorescence was done exactly as described in example 1.

Results and Discussion:

Again, the results using GFP as reporter system show the transferability of promoter activity detected using GFP-Zeo (Table 20).

Multicopy-Strains:

As described in example 1 and 2, the occurrence of multicopy-strains using ZEOCIN™ as selection marker is very common. The frequency of multicopy-strains could be increased enormously by increasing the concentration of ZEOCIN™ on the selection plates to 500 and 1000 µg/ml, respectively.

TABLE 20

Relative promoter activity of several AOX1 promoter variants with GFP and GFP-Zeo as reporter gene compared to the wild type promoter under the same conditions (derepression and induction, respectively)

| | GFP | | GFP-Zeo | |
|---|---|---|---|---|
| | Strain No. | Methanol RFU | Strain No. | Methanol RFU |
| Promoter variant | | | | |
| WT | E1 | 100% | D2 | 100% |
| ΔHap1 | C9 | 89% | A2 | 84% |
| Δ1 | 4E6 | 79% | A9 | 134% |
| Δ1-3 | 8-F12 | 75% | D5 | 67% |
| Δ2 | G12 | 37% | F2 | 40% |
| ΔRap1 | D6 | 27% | B9 | 34% |
| Δ3 | H3 | 26% | H2 | 70% |
| ΔAdr1 | A9 | 50% | A2 | 56% |

TABLE 20-continued

Relative promoter activity of several AOX1 promoter variants with GFP and GFP-Zeo as reporter gene compared to the wild type promoter under the same conditions (derepression and induction, respectively)

| | GFP | | GFP-Zeo | |
|---|---|---|---|---|
| | Strain No. | Methanol RFU | Strain No. | Methanol RFU |
| Δ4 | C7 | 66% | H9 | 71% |
| Δ5 | 38E6 | 28% | D4 | 31% |
| ΔMat1MC | 6C2 | 31% | F6 | 32% |
| Δ6 | 37F5 | 79% | H3 | 91% |
| Δ6* | E11 | 23% | A5 | 40% |
| ΔGcr1 | A9 | 60% | A2 | 55% |
| Δ7 | D12 | 38% | A7 | 25% |
| ΔQA-1F | 7A3 | 61% | E2 | 61% |
| ΔQA-1Fzus | 7A6 | 15% | H7 | 25% |
| Δ8 | E1 | 11% | H1 | 17% |
| Δ9 | 3E5 | 23% | A12 | 61% |
| Δ2Δ6 | 4B10 | 22% | F3 | 21% |
| Δ736-41 | 5A7 | 8.8% | C6 | 6% |
| Δ737-38 | 1G11 | 5.0% | A3 | 8% |
| Multicopy-Strains | | | | |
| Δ1-3 | 8B10 | 400% | | |
| Δ6 | 37A3 | 650% | | |

Example 5

Sufficiency Series Using GFP

To test small parts of the AOX1 promoter in a system free of almost all the transcription factor binding sites, the AOX1 promoter was cut a few base pairs in front of the TATA box at positions −176 and −194 which results in basal promoter elements AOX176 and AOX194 (Table 21). To allow subsequent cloning of promoter elements in front of the basal promoter fragments as well as cloning of the basal promoter a BspTI and an EcoRI restriction site were inserted at the 5' and the 3' end, respectively.

TABLE 21

Sequence of basal AOX1 promoter elements AOX176 and AOX194 and promoter fragments 737 and 201-214 which will be added in front of basal promoter variants. Restriction sites BspTI and EcoRI are underlined.

| Name | Sequence (5'→3') | Seq. ID No. |
|---|---|---|
| AOX176 | CTTAAGGACAGCAATATATAAACAGAAGGAAGCTGCCCT-GTCTTAAACCTTTTTTTTATCATCATTATTAGCT-TACTTTCATAATTGCGACTGGTTCCAAT-TGACAAGCTTTTGATTTTAACGACTTTTAACGACAACT- | 90 |

TABLE 21-continued

Sequence of basal AOX1 promoter elements AOX176 and AOX194 and promoter fragments 737 and 201-214 which will be added in front of basal promoter variants. Restriction sites BspTI and EcoRI are underlined.

| Name | Sequence (5'→3') | Seq. ID No. |
|---|---|---|
| AOX194 | TGAGAAGATCAAAAAACAACTAATTATTGAAAGAATTC <br><br>CTTAAGTGTTCTAACCCCTACTTGACAGCAATATA-<br>TAAACAGAAGGAAGCTGCCCTGTCT-<br>TAAACCTTTTTTTTATCATCATTATTAGCT-<br>TACTTTCATAATTGCGACTGGTTCCAAT-<br>TGACAAGCTTTTGATTTTAACGACTTTTAACGACAACT-<br>TGAGAAGATCAAAAAACAACTAATTATTGAAAGAATTC | 91 |
| 737 | TAGCCTAACGTT | 92 |
| 201-214 | CATGATCAAAATTT | 93 |

Cloning:
Basal AOX1 elements were amplified from pAOX (10 ng) using primers AOX1basalrv (Table 21, 10 pmol) and AOX-basalfwn (10 pmol, AOX194) and AOX176fw (10 pmol, AOX176), respectively. PCR was performed using Phusion™ polymerase (0.6 u) at appropriate conditions in a total volume of 50 µl.

Promoter variant AOX176-737 was amplified by PCR using primers AOX1basalrv and 737-38AOX176 as described above. Promoter variant AOX176-201-214 was amplified by PCR using primers AOX1basalrv and 201-214AOX176 as described above.

The resulting PCR products could be cloned into vector pPICZ-GFP employing BglII/EcoRI restriction cut and ligation using T4 DNA Ligase thereby replacing the wild type AOX1 promoter.

```
          BglII     BspTI                                                                              EcoRI
          ~~~~~     ~~~~~~                                                                             ~~~~~~~
          AGATCTCGAC TTAAGCAATC GTCTTACTTT CTAACTTTTC TTACCTTTTA CATTTCAGCA ATATATATAT ATATTTCAAG GATATACCGA ATTC

TCTAGAGCTG AATTCGTTAG CAGAATGAAA GATTGAAAAG AATGGAAAAT GTAAAGTCGT TATATATATA TATAAAGTTC CTATATGGCT TAAG
```

The 4 oligonucleotides Leu2basal1f, Leu2basal2f, Leu2basal1r and Leu2basal2r (25 pmol each) were mixed in a total volume of 20 µl, heated to 95° C. for 2 minutes and cooled down to room temperature slowly. 3 µl of the mixture were ligated with 159 ng of a pPICZ-GFP BglII/EcoRI fragment for 6 h at 16° C. After transformation into E. coli the resulting vector was called pLeu2basal-GFP.

Promoter variant Leu2-737 was amplified by PCR using primers LEU2basalrv and 737-38Leu2 and pLeu2basal-GFP as template as described above. The resulting PCR product could be cloned into vector pPICZ-GFP employing BglII/EcoRI restriction cut and ligation using T4 DNA Ligase thereby replacing the wild type AOX1 promoter. The resulting plasmid was called pLeu2-GFP-737.

TABLE 22

Primer for generation of basal promoter elements and sufficiency constructs.

| Name | Sequence (5'→3') | Seq ID No. |
|---|---|---|
| AOX1basalrv | TTTGAATTCTTTCAATAATTAGTTGTTTTTG | 94 |
| AOX176fw | TTAGATCTCGACTTAAGGACAGCAATATATAAACAGAAG-GAAG | 95 |

TABLE 22-continued

Primer for generation of basal promoter elements and sufficiency constructs.

| Name | Sequence (5'→3') | Seq ID No. |
|---|---|---|
| AOX1basalfwn | TTAGATCTCGACTTAAGTGTTCTAACCCCTACTTGACAG | 96 |
| 737-38AOX176 | AAAGATCTTAGCCTAACGTTCTTAAGGACAGCAATATA-TAAACAGAAGGAAG | 97 |
| 201-214AOX176 | AAAGATCTCATGATCAAAATTTCTTAAGGACAGCAATA-TATAAACAGAAGGAAG | 98 |
| LEU2basal1f | GATCTCGACTTAAGCAATCGTCT-TACTTTCTAACTTTTCTTACCTTTTACATTTCAG | 99 |
| LEU2basal2f | CAATATATATATATATTTCAAGGATATACCG | 100 |
| LEU2basal1r | AATTCGGTATATCCTTGAAATATATATATATATTGCT-GAAATGTAAAAG | 101 |
| LEU2basal2r | GTAAGAAAAGTTAGAAAGTAAGACGATTGCTTAAGTCGA | 102 |
| LEU2basalrv | GGTTGAATTCGGTATATCCTTG | 103 |
| 737-38Leu2 | AAAGATCTTAGCCTAACGTTCTTAAGCAATCGTCT-TACTTTCTAAC | 104 |

Transformation, Growth and GFP Detection:

For *Pichia pastoris* transformation all plasmids were linearized by BamHI. Transformation was performed as described in example 1. After transformation and a 2 h regeneration phase cells were plated on YPD-Zeo agar plates containing 100 µg/ml ZEOCIN™.

Growth of *Pichia pastoris*, methanol induction and measurement of GFP fluorescence was done exactly as described in example 1.

Results and Discussion:

This experiment shows that addition of small elements identified in examples 1 and 2 could be used to increase the promoter strength of basal promoter elements derived from the AOX1 promoter or from the *Saccharomyces cerevisiae* LEU2 promoter.

Multicopy-Strains:

The occurrence and frequency of multicopy strains found after transformation is exactly the same as described in Example 4. The different site of linearization within the plasmid didn't have any influence on the generation of multicopy-strains.

TABLE 23

Promoter activity of basal promoter elements without and after addition of small AOX1 promoter fragments supposed to act as regulator binding sites. GFP has been used as reporter protein. Singlecopy strains as well as multicopy strains are shown.

| | Singlecopy | | Multicopy | |
|---|---|---|---|---|
| | Derepr. RFU | Methanol RFU | Derepr. RFU | Methanol RFU |
| pAOX176-GFP | n.d. | 22.1 ± 0.2 | — | — |
| pAOX194-GFP | n.d. | 16.9 ± 2.9 | — | — |
| pAOX176-GFP-737 | n.d. | 21.2 ± 1.1 | 59 ± 6 | 265 ± 38 |
| pAOX176-GFP-201-214 | 69.6 ± 6.0 | 44.9 ± 4.8 | — | — |

TABLE 23-continued

Promoter activity of basal promoter elements without and after addition of small AOX1 promoter fragments supposed to act as regulator binding sites. GFP has been used as reporter protein. Singlecopy strains as well as multicopy strains are shown.

| | Singlecopy | | Multicopy | |
|---|---|---|---|---|
| | Derepr. RFU | Methanol RFU | Derepr. RFU | Methanol RFU |
| pLeu2basal-GFP | n.d. | 11.3 ± 3.6 | — | — |
| pLeu2-GFP-737 | n.d. | 19.2 ± 1.9 | 55 ± 5 | 138 ± 11 |

References:

[1] Nakagawa, T., et al. (1999) Yeast 15(12), 1223-30.
[2] Koutz, P., et al. (1989) Yeast 5(3), 167-77.
[3] Ohi, H., et al. (1994) Mol. Gen. Genet. 243(5), 489-99.
[4] Cregg, J. M., et al. (1989) Mol. Cell. Biol. 9(3), 1316-23.
[5] Nakagawa, T., et al. (2002) Yeast 19(12), 1067-73.
[6] Sakai, Y., et al. (1998) J. Bacteriol. 180(22), 5885-5890.
[7] Genu, V., et al. (2003) Eur. J. Biochem. 270(11), 2467-2475.
[8] Goedecke, S., et al. (1994) Gene 139(1), 35-42.
[9] Tschopp, J. F., et al. (1987) Nucleic Acids Res. 15(9), 3859-76.
[10] Parpinello, G., et al. (1998) J. Bacteriol. 180(11), 2958-67.
[11] Alamae, T. et al. (1994) Yeast 10(11), 1459-66.
[12] Inan, M. et al. (2001) J. Biosci. Bioeng. 92(6), 585-589.
[13] Sreekrishna, K., et al. (1997) Gene 190(1), 55-62.
[14] Romanos, M., et al. (1998) Methods Mol. Biol. 103(55-72.
[15] Quandt, K., et al. (1995) Nucleic Acids Res. 23(23), 4878-84.
[16] Ausubel, F. M., et al., Current Protocols in Molecular Biology, John Wiley and Sons, New York, 2003.
[17] Corpet, F. (1988) Nucleic Acids Res. 16(22), 10881-90.

[18] Chema, R., et al. (2003) Nucleic Acids Res. 31(13), 3497-500.
[19] Bennett, R. P., et al. (1998) BioTechniques 24(3), 478-82.
[20] Farinas, E. T., et al. (2001) Adv. Synth. Catal. 343(6), 601-606.
[21] Huie, M. A. et al. (1996) Yeast 12(4), 307-17.
[22] Lopez, M. C., et al. (1998) PNAS U.S.A. 95(24), 14112-7.
[23] Zeng, X., et al. (1997) Genetics 147(2), 493-505.
[24] Del Vescovo, V., et al. (2004) J. Mol. Biol. 338(5), 877-93.
[25] Simon, M., et al. (1992) Yeast 8(4), 303-9.
[26] Raschke, W. C., et al. (1996) Gene 177(1-2), 163-7.
[27] Andrianopoulos, A. et al. (1994) Mol. Cell. Biol. 14(4), 2503-15.
[28] Kwast, K. E., et al. (1998) J. Exp. Biol. 201 (Pt 8)(1177-95.
[29] Bourgarel, D., et al. (1999) Mol. Microbiol. 31(4), 1205-15.
[30] Dang, V. D., et al. (1996) J. Bacteriol. 178(7), 1842-9.
[31] Hahn, J. S. et al. (2004) J. Biol. Chem. 279(7), 5169-76.
[32] WO 02/081650
[33] U.S. Pat. No. 6,699,691
[34] Wang, W. et al. (1999) Biotechniques 26(4), 680-2.
[35] Morawski, B., et al. (2000) Protein Eng 13(5), 377-84.
[36] Weis, R., et al. (2004) FEMS Yeast Res. 5, 179-189.

Sequence Listing:

Seq ID No. 1: AOX1 promoter of *Pichia pastoris*
ggtaccagatctaacatccaaagacgaaaggttgaatgaaaccttttgc
catccgacatccacaggtccattctcacacataagtgccaaacgcaacag
gaggggatacactagcagcagaccgttgcaaacgcaggacctccactcct
cttctcctcaacacccacttttgccatcgaaaaaccagcccagttattgg
gcttgattggagctcgctcattccaattccttctattaggctactaacac
catgactttattagcctgtctatcctggcccccctggcgaggttcatgtt
tgtttatttccgaatgcaacaagctccgcattacacccgaacatcactcc
agatgagggctttctgagtgtggggtcaaatagtttcatgttccccaaat
ggcccaaaactgacagtttaaacgctgtcttggaacctaatatgacaaaa
gcgtgatctcatccaagatgaactaagtttggttcgttgaaatgctaacg
gccagttggtcaaaaagaaacttccaaaagtcggcataccgtttgtcttg
tttggtattgattgacgaatgctcaaaaataatctcattaatgcttagcg
cagtctctctatcgcttctgaaccccggtgcacctgtgccgaaacgcaaa
tggggaaacacccgcttttggatgattatgcattgtctccacattgtat
gcttccaagattctggtgggaatactgctgatagcctaacgttcatgatc
aaaatttaactgttctaaccccctacttgacagcaatatataaacagaagg
aagctgccctgtcttaaaccttttttttatcatcattattagcttactt
tcataattgcgactggttccaattgacaagcttttgattttaacgactttt
taacgacaacttgagaagatcaaaaaacaactaattattgaaagaattca
acc

The invention claimed is:

1. An isolated *Pichia pastoris* alcohol oxidase 1 (AOX1) promoter comprising the wild type AOX1 promoter sequence as set forth in SEQ ID NO: 1, wherein nucleotides 170 to 235 are deleted;
wherein the deletion causes increased expression activity compared to the wild-type promoter, under methanol-induced conditions.

2. The isolated promoter of claim 1, further comprising a mutation of a transcription factor binding site (TFBS) within SEQ ID NO:1, and/or further comprising at least one mutation selected from the group consisting: a mutation within nucleotides 694 to 723, a mutation within nucleotides 729-763 a mutation within nucleotides 304 to 350, a mutation within nucleotides 364 to 393, a mutation within nucleotides 434 to 508, a mutation within nucleotides 509 to 551, a mutation within nucleotides 552 to 560, a mutation within nucleotides 585 to 617, a mutation within nucleotides 621 to 660, a mutation within nucleotides 625 to 683, a mutation within nucleotides 736 to 741, a mutation within nucleotides 737 to 738, a mutation within nucleotides 726 to 755, a mutation within nucleotides 784 to 800, a mutation within nucleotides 823 to 861 of SEQ ID NO: 1, and a combination thereof.

3. The isolated promoter of claim 2, wherein the at least one mutation comprises a deletion, a substitution, an insertion, an inversion, a multiplication or a combination thereof.

4. The isolated promoter of claim 2, wherein the transcription factor binding site (TFBS) comprises Hap1.

5. The isolated promoter of claim 2, wherein the transcription factor binding site (TFBS) comprises Hap1 nucleotides 54 to 58 of SEQ ID NO: 1, Hsf nucleotides 142 to 149 and 517 to 524 of SEQ ID NO: 1, Hap234 nucleotides 668 to 672 of SEQ ID NO: 1, Stre nucleotides 281 to 285 of SEQ ID NO: 1, Rap 1 nucleotides 335 to 339 of SEQ ID NO: 1, Adr1 nucleotides 371 to 377 of SEQ ID NO: 1, Mat1MC nucleotides 683 to 687 of SEQ ID NO: 1, Ger1 nucleotides 702 to 706 of SEQ ID NO: 1, QA- IF nucleotides 747 to 761 of SEQ ID NO: 1 or a combination thereof.

6. An isolated nucleic acid molecule comprising:
at least one mutant *Pichia pastoris* alcohol oxidase 1 (AOX1) promoter according to claim 1; and
at least one nucleic acid that encodes a protein, a peptide or a functional nucleic acid, wherein the at least one mutant *Pichia pastoris* alcohol oxidase 1 (AOX1) promoter and the at least one nucleic acid are operably linked together forming a single- or multi-copy expression cassette.

7. An isolated mutant *Pichia pastoris* alcohol oxidase 1 (AOX1) vector comprising:
at least one mutant *Pichia pastoris* alcohol oxidase 1 (AOX1) promoter according to claim 1.

8. An isolated cell comprising:
at least one mutant *Pichia pastoris* alcohol oxidase 1 (AOX1) promoter according to claim 1; or
at least one nucleic acid molecule comprising at least one mutant *Pichia pastoris* alcohol oxidase 1 (AOX1) promoter according to claim 1 and at least one nucleic acid that encodes a protein, a peptide or a functional nucleic acid, wherein the at least one mutant *Pichia pastoris* alcohol oxidase 1 (AOX I) promoter and the at least one nucleic acid are operably linked together forming a single- or multi-copy expression cassette.

9. The isolated cell of claim 8, wherein the cell is a eukaryotic cell.

10. The isolated cell of claim 9, wherein the *eukaryotic* cell is a methylotrophic yeast cell selected from the group consisting of *Candida*, *Hansenula*, *Pichia* and *Toruplosis*.

11. The isolated cell of claim 8 wherein the cell is a *Pichia pastoris* cell.

12. A kit for the expression of a selected protein comprising:
- a vector comprising at least one mutant *Pichia pastoris* alcohol oxidase 1 (AOX1) promoter according to claim 1; or
- a nucleic acid molecule comprising at least one mutant *Pichia pastoris* alcohol oxidase 1 (AOX1) promoter according to claim 1 and at least one nucleic acid that encodes a protein, a peptide or a functional nucleic acid, wherein the at least one mutant *Pichia pastoris* alcohol oxidase 1 (AOX1) promoter and the at least one nucleic acid are operably linked together forming a single- or multi-copy expression cassette; and
- a cell capable to express said protein under the control of the promoter.

13. The kit according to claim 12, wherein the cell is a yeast cell.

14. The kit according to claim 13, wherein the cell is a methylotrophic yeast cell selected from the group *Candida, Hansenula, Pichia* and *Toruplosis*.

15. The kit according to claim 12 wherein the cell is a *Pichia pastoris* cell.

16. A method for the expression of a recombinant protein, peptide or functional nucleic acid in a cell comprising the following steps:
   providing a nucleic acid molecule comprising at least one mutant *Pichia pastoris* alcohol oxidase 1 (AOX1) promoter according to claim 1 and at least one nucleic acid that encodes a protein, a peptide or a functional nucleic acid, wherein the at least one mutant *Pichia pastoris* alcohol oxidase 1 (AOX1) promoter and the at least one nucleic acid are operably linked together forming a single- or multi-copy expression cassette;
   transforming said cell with said nucleic acid molecule, and culting the transformed cell in a suitable culture medium, wherein the recombinant protein is expressed.

17. The method according to claim 16, wherein said cell is a methylotrophic yeast cell.

18. The method according to claim 17, wherein the methylotrophic yeast cell is selected from the group consisting of *Candida, Hansenula, Pichia* and *Toruplosis*.

19. The method according to claim 16, wherein the cell is a *Pichia pastoris* cell.

20. A method of expressing a nucleic acid molecule for the expression of a protein, peptide or functional nucleic acid comprising the steps of:
   transforming an isolated cell with a nucleic acid molecule comprising at least one mutant *Pichia pastoris* alcohol oxidase 1 (AOX1) promoter according to claim 1 and at least one nucleic acid that encodes a protein, a peptide or a functional nucleic acid, wherein the at least one mutant *Pichia pastoris* alcohol oxidase 1 (AOX1) promoter and the at least one nucleic acid are operably linked together forming a single- or multi-copy expression cassette; or
   providing an isolated cell comprising at least one mutant *Pichia pastoris* alcohol oxidase 1 (AOX1) promoter according to claim 1; at least one nucleic acid molecule comprising at least one mutant *Pichia pastoris* alcohol oxidase 1 (AOX1) promoter according to claim 1 and at least one nucleic acid that encodes a protein, a peptide or a functional nucleic acid, wherein the at least one mutant *Pichia pastoris* alcohol oxidase 1 (AOX1) promoter and the at least one nucleic acid are operably linked together forming a single- or multi-copy expression cassette;
   culturing the isolated cell in a suitable culture medium; and
   inducing expression of said protein, peptide or functional nucleic acid.

21. A method for the isolation of super expression clones comprising the steps:
   a) introducing a nucleic acid molecule comprising a mutated methanol inducible promoter of claim 1 operably linked to a nucleic acid encoding for va protein or to a functional nucleic acid and to a selective marker gene to form a single- or multi-copy expression vector comprising said nucleic acid molecule into a cell;
   b) transferring the cell to a medium comprising an appropriate selective marker, a non-repressing carbon source and methanol for the selective growth of super expression clones under inducing conditions;
   c) incubating the cell on said medium;
   d) isolating a colony of the cell; and
   e) detecting super expressing clones by determining the expression rate of said cell.

22. The method according to claim 21, wherein the selective marker comprises an antibiotic.

23. The method according to claim 21 wherein the cell is a methylotrophic yeast cell.

24. The method according to claim 23, wherein the yeast cell is selected from the group consisting of *Candida, Hansenula, Pichia* and *Toruplosis*.

25. The method according to claim 21 wherein the cell is a *Pichia pastoris* cell.

26. The method according to claim 21 wherein the non-repressing carbon source is selected from the group consisting of alanine, mannitol, sorbitol, threhalose, lactose and combinations thereof.

27. The method according to claim 21 wherein the nucleic acid molecule is introduced into the cell by transformation, electroporation, chemical transformation, protoplast fusion, particle bombardment or a combination thereof.

28. The vector of claim 7, further comprising at least one nucleic acid that encodes a protein, a peptide or a functional nucleic acid, wherein the at least one mutant *Pichia pastoris* alcohol oxidase 1 (AOX1) promoter and the at least one nucleic acid are operably linked together forming a single- or multi-copy expression cassette.

29. The method of claim 16, further comprising inducing expression of said protein, peptide or functional nucleic acid; and isolating said expressed protein, peptide or functional nucleic acid.

* * * * *